US009663770B2

(12) United States Patent
Rogers et al.

(10) Patent No.: US 9,663,770 B2
(45) Date of Patent: May 30, 2017

(54) REVERSE TRANSCRIPTASES FOR USE IN HIGH TEMPERATURE NUCLEIC ACID SYNTHESIS

(71) Applicant: LIFE TECHNOLOGIES CORPORATION, Carlsbad, CA (US)

(72) Inventors: Jeffrey Rogers, Escondido, CA (US); Jason Potter, San Marcos, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 14/603,256

(22) Filed: Jan. 22, 2015

(65) Prior Publication Data

US 2015/0210989 A1  Jul. 30, 2015

Related U.S. Application Data

(60) Provisional application No. 61/930,395, filed on Jan. 22, 2014.

(51) Int. Cl.
*C12N 9/12* (2006.01)
*C12N 15/10* (2006.01)
*C12P 19/34* (2006.01)

(52) U.S. Cl.
CPC ....... *C12N 9/1276* (2013.01); *C12N 15/1096* (2013.01); *C12P 19/34* (2013.01); *C12Y 207/07049* (2013.01)

(58) Field of Classification Search
None
See application file for complete search history.

(56) References Cited

U.S. PATENT DOCUMENTS

| | | | |
|---|---|---|---|
| 5,405,776 A | 4/1995 | Kotewicz et al. | |
| 5,561,058 A | 10/1996 | Gelfand et al. | |
| 5,618,711 A | 4/1997 | Gelfand et al. | |
| 5,693,517 A | 12/1997 | Gelfand et al. | |
| 6,013,488 A | 1/2000 | Hayashizaki | |
| 7,056,716 B2 | 6/2006 | Potter et al. | |
| 7,078,208 B2 | 7/2006 | Smith et al. | |
| 8,580,548 B2 | 11/2013 | Janulaitis et al. | |
| 8,835,148 B2 | 9/2014 | Janulaitis et al. | |
| 2001/0092500 | * 12/2001 | Smith et al. ............. | C12N 9/12 435/194 |
| 2007/0020622 A1 | 1/2007 | Lee et al. | |

(Continued)

FOREIGN PATENT DOCUMENTS

| | | |
|---|---|---|
| EP | 0962526 | 12/1999 |
| EP | 1931772 | 11/2011 |

(Continued)

OTHER PUBLICATIONS

GeneSeq Accession No. AAU74999, published Aug. 7, 2009.*

(Continued)

*Primary Examiner* — Richard Ekstrom

(57) ABSTRACT

The invention provides novel reverse transcriptases (RTs) with desirable properties such as increased thermostability, increased thermoreactivity and/or increased resistance to inhibitors. In certain embodiments, the invention provides methods of producing, amplifying and/or sequencing nucleic acid molecules (particularly cDNA molecules) using kits, compositions and/or reactions mixtures containing such novel reverse transcriptase enzymes.

20 Claims, 16 Drawing Sheets

(56) References Cited

U.S. PATENT DOCUMENTS

2011/0065606 A1 3/2011 Janulaitis et al.
2011/0081704 A1 4/2011 Smith et al.

FOREIGN PATENT DOCUMENTS

| EP | 2604688 | 6/2013 |
|---|---|---|
| JP | 2000139457 | 5/2000 |
| WO | 98/23733 | 6/1998 |
| WO | 98/47912 | 10/1998 |
| WO | 2004/024749 | 3/2004 |
| WO | 2007/022045 | 2/2007 |
| WO | 2009/125006 | 10/2009 |

OTHER PUBLICATIONS

Cadwell, et al., "Randomization of Genes by PCR Mutagenesis", *PCR Methods Applications*, vol. 2, No. 1, Aug. 1992, pp. 28-33.

EBI, "MMLV RT Mutant Protein", Accession No. AEX83173, Jun. 14, 2007, 4 Pages.

EBI, "Reverse Transcriptase Mutant", Accession No. AZT62682, Apr. 12, 2012.

Gerard, et al., "Reverse Transcriptase. The Use of Cloned Moloney Murine Leukemia Virus Reverse Transcriptase to Synthesize DNA from RNA", *Molecular Biotechnology*, vol. 8, No. 1, Aug. 1997, pp. 61-77.

Halvas, et al., "Development of an In Vivo Assay to Identify Structural Deteminants in Murine Leukemia Virus Reverse Transcriptase Important for Fidelity", *Journal of Virology*, vol. 74, No. 1, Jan. 2000, pp. 312-319.

Kaushik, et al., "Tyrosine 222, a Member of the YXDD Motif of MuLV RT, Is Catalytically Essential and Is a Major Component of the Fidelity Center", *Biochemistry*, vol. 38, No. 9, Mar. 2, 1999, pp. 2617-2627.

PCT/US2015/012534; International Search Report and Written Opinion mailed Sep. 2, 2015, 19 pages.

* cited by examiner

SEQ ID NO:1 wild type M-MLV DNA

Figure 8A

SEQ ID NO:1 – cont'd
wild type M-MLV DNA

```
1601 GTAAGCCGGG AGCTGGGGTG ACCACCGAAA CCGAGGTAAT CTGGGCTAAA GCCCTGGCAG CCGGGACATC CGCTCAGCCG GCTGGAACTGA TAGGACTCAC
     CATTCGGCCC TCGACCCCAC TGGTGGCTTC TGGTCGCATT AGACCCGATTT CGGGACCGTC GGCCCTGTAG CGAGTCGGCC CGACTTGACT ATCGTGAGTG
1701 CCAGGCCCTA GAGATGCCAG AAGGTAAGAA GCTAAAAGTT TATACTGAAA GCAGTTACTA TGCCCATATCC ATGGAGAAAT ATACAGAAAG
     GGTCCGGGAT TTCTACGGTC TTCCATTCTT CGATTTGCAA ATATGACTAT CGGCAACTACG AAAACGATGA CGGGTATAGG TACCTTTTA TATGTCTTCC
1801 CGTGGGTTGC TCAATCAGA AGGCAAAGAG ATCAAAATA AAGACGAGAT CTTGGCCCTA CTAAAAGCCC TCTTTCTGCC CAAAAGACTT AGCATAATCC
     GCACCCAACG AGGTAGTCT TCCGTTTCTC TAGTTTTTAT TCTGTCTA GAACCGAGAT GATTTTCGGG AGAAAGACGG GTTTTCTGAA TCGTATTAGG
1901 ATTGTCGAG ACATCAAAAG GGACACAGCG AGGCAACCGG ATGGCTGACC AAGCGCGG TTCCGTCGG TAGTGTCT GAGTGTCGTG
     TAACAGTCG TGTAGTTTTC CCTGTGTCGC GGCTCCGATC TCCGTTGGCC TACCGACTGG TCCGCCGGC TTGCCGGAC ATCAGAGA CTCAGACAC
2001 CTCTACCCTC CTCATAGAAA ATTCATCACC C
     GAGATGGGAG GAGTATCTTT TAAGTAGTGG G
```

Figure 8B

SEQ ID NO:2 wild type M-MLV

```
  1  TLNIEDEHRL HETSKEPDVS LGSTWLSDFP QAMAETGGMG LAVRQAPLII
 51  PLKATSTPVS IKQYPMSQEA RLGIKPHIQR LLDQGILVPC QSPWNTPLLP
101  VKKPGTNDYR PVQDLREVNK RVEDIHPTVP NPYNLLSGLP PSHQWYTVLD
151  LKDAFFCLRL HPTSQPLFAF EWRDPEMGIS GQLTWTRLPQ GFKNSPTLFD
201  EALHRDLADF RIQHPDLILL QYVDDLLLAA TSELDCQQGT RALLQTLGNL
251  GYRASAKKAQ ICQKQVKYLG YLLKEGQRWL TEARKETVMG QPTPKTPRQL
301  REFLGTAGFC RLWIPGFAEM AAPLYPLTKT GTLFNWGPDQ QKAYQEIKQA
351  LLTAPALGLP DLTKPFELFV DEKQGYAKGV LTQKLGPWRR PVAYLSKKLD
401  PVAAGWPPCL RMVAAIAVLT KDAGKLTMGQ PLVILAPHAV EALVKQPPDR
451  WLSNARMTHY QALLLDTDRV QFGPVVALNP ATLLPLPEEG LQHNCLDILA
501  EAHGTRPDLT DQPLPDADHT WYTDGSSLLQ EGQRKAGAAV TTETEVIWAK
551  ALPAGTSAQR AELIALTQAL KMAESKKLNV YTDSRYAFAT AHIHGEIYRR
601  RGLLTSEGKE IKNKDEILAL LKALFLPKRL SIIHCPGHQK GHSAEARGNR
651  MADQAARKAA ITETPDTSTL LIENSSP
```

Figure 9

SEQ ID NO:3

Mut PS M-MLV DNA

```
   1 ACCCTGAACA TCGAAGATGA ATATCGTCTG CATGAACAAC GTAAGAAAAC GGATTAGC CTGGGTAGCA CTGCCTGAG CGATTTCCG CAGCCATGG
     TCGGACTTGT AGCTTCTACT TATAGCAGAC GTACTTGTTG CATTCTTCG CCTACAATCC GACCCATCT GACCGACTGT GACTGGACTC GTCGGTACTT
 101 CAGRAACCGG TGCTATAGGC GACCATACCA CTGAGGCACG CCGTCCGTGG CCGATAATAA GACGACTTC GTGGTCCTG GAACCAGCAC ATCCGATGAG
     GTCTTTGGCC ACGATATCCG CTGGTATGGT GACTCGTGC GGCTAGCACC GGCTATTATT CTGCTGAAAG GCACCAGGAC GCACCAGGTG TAGGCTACTC
 201 GCAGAACCG CGTCTGGGTA TCAAACCCA TATTCAGGT CTCCTGGATG AGGGTATTCT CAGAGCCGT CGAGAGCCCT GTACTGTGGG CGACTACCGC
     CGTCTTTGGC GCAGAGCCAT AATTTGCGGT ATAATTCGA GAGGACCTAG TCCATATGA AGTTCGCTA GCTCCCTAA GCTGATCAGCA CGACTGCCGC
 301 GTTAAAAAAC CGGTTACAAA TTAATATCGT CCGGTTCAGC AATTGGGTGA AGTTAATTAAA CGCGTGGAAG ACGTTCATCC GACCCTCGG AATCCGTATA
     CAATTTTTTC GCCAATGTTT ACTATAGCA GCCCAAGTCG TAGCAACTC TCAATTAITT GCGCACGTTC TGCAAGTAGG CTGGAGCC TTAGCATAT
 401 ATCTGCTGAG GGTCTGTGCT CGGACCATC AGTGTATAC CTGAAAGATG CGTTTTTTG TCTCGTCG CATGCGACCA GCCAGGCGT
     TAGACGACTC GCCAGACGGA GCCTGGTAG TGACATATG GACTTCCTAC GRAAAAAC AGAGCAGAC GTARGCTGGT CGGTCGGCGA
 501 GTTCGATTT GAATGGCTG ATCGGCRAAT GGGTATTAGC GCTCAACTGA CCTGGACCG TCTGGGCTAG GTTTTAAAA ATGACCGGC CCTGTTTGAT
     CAAGCTAAA CTTACGGAC TAGCCTTTA CCCATAATC CGATTCGACT GGACCTGGCT AGACCCGGTC CCAAATTTTT TATCGGCTGG GGACAATTA
 601 GAGCCCTGC GTCGTGATCT GGGAATTCT CGTATTCAG ATCGGAATCT CATTCGCTG CAGTAGTTG ATGATCGTT GCTGAGTAGA ACCACGTAAC
     CTCGGGACG CAGCACTAGA CGTCACTAGA GCATAGTCG TAGCCCTAAA CTAAGAGAC GTCATAGAAC TACTAGACGA GACTCATCA TGGTCGCTG
 701 TGGATTGTCA GCAGGGCACC CCTGCACTGC CGGTGCACT GGTTACGGT CGGTGATCCG GGTATCCGTG CGAGCAGAA ATTCGTCGAGG ARCAGTGAA
     ACCTACAGT CGTCCGTGG GGACGGACG ACCTCGGA GGCCACCTCGG CCATACGCAC GTTCCGGTT TTTCGTGTC TTAAAGTCT TTGTCATT
 801 ATATTGGC TATCCTGA AAGAAGGCA TTCTTCCAGT CGCAACCGAC TGGCTTCGGTS CATTCTTTG GCAATACCGA COGAAACACC GCTGCAGCGG
     TATAACGG ATAGACCACT TTCTTCCAGT AAGAAGGTCA AGGCTTGGC ACCGAAGCCAG GTAAGAAAC CGTTATCGGT CAGCCGACC GCTGCAGCTG
 901 CGTAAATTC TCGGTACAGC AGGTAATTGC CGTCGTTCA TTCCGGGTTT TGCAGAAATG GCAGCCACGC TGTATCGGCT GACCAAACCC GGGACCTGT
     GCATTGAAGA ACCAAGTGG TGATTAACG GCAGACAAGT AAGGCCCAAA AGTCTTTAC CGTCGGCAGG ACATGCCCAG CTGGTTGCGG CCTGGGACA
1001 TTAATTGGGG TGGGATTAAG CAGAAAACGT ATCGAAGCA TAAAGAGCGA CTGCTGAGCG AACGGGTCC GTGGCGTCT CGGTTGCAT ACGGGCAA AAAACGGAT
     AATTACCCC AGCCTAGTC TGTTTCGGA TAGTTTCTT ATTGTCGT GACGACTGC CACCAGG GCCCGCAGGA CACCAGAAGTA TAGACTGTT TTTGACTTA
1101 ACTGTTGT GATGAAAAC AGGTAATGC AAAAGCTCTT GTCATCCAA GAGTCGTTT TTGACCCAGG GATTCGACTCG AATGGTGAG ACCCTTGTA
     TGACAAGTAC CTACTTTTG TCCAAATACG TTTTCACGA GAATTCGAGAA CAGTGGGTTT TTGACCCAAG GGCAAGGTA TTACCAGTC GGCACCAAT
1201 COGGTAGCAG CAGTTGCC TCCTGCTG CGTATGCTG GCGCACAGC CATACCAAC GTCATCGGTG CAGCAATGC AGTGTGAC AAAGATGAC GTAACTGAC AATGGTCAG CCGCTGTTA TTACCAGTC GGCACCAAT
     GGCCAACGTC CAGTGGCT GCCACACGAT AGGCACAGAA ACAGACTCGG GCATAGCCAAG GCAGACTCGT TCACACACTG GTAACTGACAC CATTGACTG GACCGTAT GCCGACGCAT
1301 TTGGCACC GCATCCAGTT GAACCAGTG CTCCTGCACT TCGGATCGT TGGTGAGCA ACGAGGCA TGGTGAGCT AGGCCCTGAT TGGTGGAT AGGCCCTGC TGTCTCGGAT ACGACCATATC
     AACCCGTGG CGTACGTAA CTTCTGACG AATTCGCG AGCCTRAGCCA ACCACTCCA TCCGGGATA CTCGATATA GACCCGTCT GTCCGGACG ACGACCATCT
1401 CGATCGTGTT CAGTTGTC ACTGAATGCC CGGTTGTGC ACTGAAGTCG GCAACCTGCC TGCGCTGCC GGAAGAAGT GTTCTTCA GCGCGATA ATTGCGGATA TATTCTGCC
     GCTACACA GTCAAACAG TGACACTCA GCCAACAGG TGACTTAGG ACGGGGACGG CCTTCTTGGAA AGAAGAGT CGCTAGACCT TAACAGACCT ATAAGACGG
1501 GAAGAGCAAG GCACCCGCC GGATTGCAA GATTAGCGT TGCCTGATC CAGAGCGG GCCATGCGG ACCGAATACG TGGTAAGGGG AGTATAACC CCTAGTAGCC GAGGCACGC CTTGGCTGC
     CTTCGCTGTAC CGTGGGCAGG CCTAACGTT GGATCACTTG TCGGACTGC CAGAGCGGG GCCATGCGG ACCGAATACG TGGTAAGGGG AGTATAACC CCTAGTAGCC GAGGCACGC CTTGGCTGC
```

Figure 10A

SEQ ID NO:3 – cont'd

MLF D9 M-MLV DNA

```
1601 GTAAAGTCGG TGGAGCAGTT ACCACCGAAA CCGAAGTTAT TTGGGCAAAA GCAATGGCTG CTGGACCAG CGCACAGCGT GCAGAGCTGA TTGCACTGAC
     CATTCTGCCC AGTTCGTCAA TGGTGGCTTT GGCTTCAATA ACCCGGTTTT CGTGACCGAC GACGTGGTC GCGTGTCGA CGTCTCGACT AACTGGACTG
1701 CCAGACACTG CGTATGGCCG GCATACCGGC TTCCATTTTT TGACTTACAC ATGAAGTGTC GCCGTATGC ATTGCAACC GCACATATC AGGCGAAAT TATCGCTGT
     CGTGGTTGCG GCATACCGGC GCATACCGGC TTCCATTTTT TGACTTACAC ATGAAGTGTC GCCGTATGC ATTGCAACC GCACATATC AGGCGAAAT TATCGCTGT
1801 CGTGGTTGCC TGACAGCGA AGTCAGCGCT TCCATTTTT TAATTTTAT TTCTACTTTA AGACCGGAC GCTTCGTG ACAAGACGG CTTGCGGAC TGTAATAAAG
     GCACCGAAACG ACTGGTCGCT TCCATTTCGG CAGAGCACG CGTAATGCG CAGAAACG ATGGCAAACC AGGCAGCACA TAAAGCAGGA ATTACCGAAA ACCGGATAC
1901 ATTGTCCGGG TGATCAGAAA CGTCATAGCG CAGAACACG CGTAATGCG CAGAAACG ATGGCAAACC AGGCAGCACA TAAAGCAGGA ATTACCGAAA ACCGGATAC
     TAACAGCCC AGTAGTCTTT GCAGTATGC GTCTTCGGCG GCCATTGGCA TCCGGTTTGG TCCGTGGTGC ATTTCGTTGT TAATCGTTT TAAGCCTTG
2001 CAGCAGCCTG CGGATTGAAA ATAGCAGCCC G
     GTCGTCGGAC GCCTAACTTT TATCGTCGGG C
```

Figure 10B

SEQ ID NO:4

Mutant D9 M-MLV

```
  1  TLNIEDEYRL HETSKEPDVS LGSTWLSDFP QAWAETGGMG LAVRQAPLII
 51  LLKATSTPVS IKQYPMRQKA RLGIKPHIQR LLDQGILVPC QSPWNTPLLP
101  VKKPGTNDYR PVQDLREVNK RVEDIHPTVP NPYNLLSGLP PSHQWYTVLD
151  LKDAFFCLRL HPTSQPLFAF EWRDPEMGIS GQLTWTRLPQ GFKNSPALFD
201  EALHRDLADF RIQHPDLILL QYVDDLLLAA TSELDCQQGT RALLQTLGDL
251  GYRASAKKAQ ICQKQVKYLG YLLKEGQRWL TEARKETVMG QPTPKTPRQL
301  RKFLGTAGFC RLFIPGFAEM AAPLYPLTKP GTLFNWGPDQ QKAYQEIKQA
351  LLTAPALGLP DLIKPFELFV DEKQGYAKGV LTQKLGPWRR PVAYLSKKLD
401  PVAAGWPPCL RMVAAIAVLT KDAGKLTMGQ PIVIGAPHAV EALVKQPPDR
451  WLSKARMTHY QALLLDTDRV QFGPVVALNP ATLLPLPEEG LQHNCLDILA
501  EAHGTRPDLT DQPLPDADHT WYTGGSSLLQ EGQRKAGAAV TTETEVIWAK
551  ALPAGTSAQR ABLIALTQAL RMAEGKKLNV YTNSRYAFAT AHIHGEIYRR
601  RGLLTSEGKE IKNKDEILAL LKALFLPKRL SIIHCPGHQK GHSAEARGNR
651  MANQAARKAA TTENPDTSTL PIENSSP
```

Figure 11

REVERSE TRANSCRIPTASES FOR USE IN HIGH TEMPERATURE NUCLEIC ACID SYNTHESIS

CROSS-REFERENCE TO RELATED APPLICATIONS

This application claims priority benefit of U.S. application No. 61/930,395 filed Jan. 22, 2014, which disclosures are herein incorporated by reference in their entirety.

SEQUENCE LISTING

The instant application contains a Sequence Listing which has been submitted electronically in ASCII format and is hereby incorporated by reference in its entirety. Said ASCII copy, created on Mar. 17, 2015, is named LT00877_SL.txt and is 49,402 bytes in size.

FIELD OF THE INVENTION

The present invention provides reverse transcriptase (RT) enzymes and compositions, methods and kits that include novel enzymes, for the reverse transcription of nucleic acid molecules.

BACKGROUND

Reverse transcriptases are foundational enzymes in biotechnology that convert RNA into DNA. These enzymes form the basis of valuable research tools that have been used to uncover many of the fundamental processes of living organisms. With respect to molecular diagnostics, these enzymes are critical components of such diagnostics, thus facilitating new tools for the diagnosis and management of the vast majority of diseases, including cancer for example. As such, improved reverse transcriptases with improved properties, such as improved efficiency, are desirable, since such improved enzymes will lead to improved molecular diagnostics.

A factor that influences the efficiency of reverse transcription is the ability of RNA to form secondary structures. Such secondary structures can form, for example, when regions of RNA molecules have sufficient complementarity to hybridize and form double stranded RNA. Generally, the formation of RNA secondary structures can be reduced by raising the temperature of solutions which contain the RNA molecules. Thus, in many instances, it is desirable to reverse transcribe RNA at temperatures above 37° C. However, reverse transcriptases generally lose activity when incubated at temperatures much above 37° C. (e.g., 50° C.).

The accuracy of methods utilizing reverse transcriptases, including molecular diagnostics methods using such enzymes, would be improved by the discovery of reverse transcriptases with improved thermostability and/or thermoreactivity. If such enzymes were available, then methods employed for other thermostable enzymes to improve accuracy, could be used to conceive new methods utilizing thermostable reverse transcriptases. For instance, 'hot start' approaches have been employed with thermostable polymerases to improve the accuracy of polymerase chain reaction (PCR) methods. In one example, U.S. Pat. No. 5,338,671 describes the use of antibodies specific for a thermostable DNA polymerase to inhibit the DNA polymerase activity at low temperatures (e.g. <70° C.). Chemical treatment with citraconic anhydride is another way hot start PCR has been achieved (see, e.g., U.S. Pat. No. 5,773,258 and U.S. Pat. No. 5,677,152). The application of such hot start approaches to reverse transcription has proven to be challenging. This is because, for example, many reverse transcriptases are not heat-stable.

Moreover, biological samples from which nucleic acids are extracted often contain additional compounds that are inhibitory to reverse transcription. Humic acid in soil, plants and feces, hematin in blood, immunoglobin G in serum, and various blood anticoagulants, like heparin and citrate, are all examples of such inhibitors. Such inhibitors may not be completely removed during the nucleic acid extraction and purification process, thus negatively impacting downstream nucleic acid synthesis, as reflected by a decrease in cDNA product produced as a result of reverse transcription.

Thus, improved reverse transcriptases, and compositions, kits and methods that include such reverse transcriptases which overcome some of the drawbacks mentioned above are met by the present invention.

BRIEF SUMMARY OF THE INVENTION

The present invention provides mutant reverse transcriptase enzymes with improved properties, and compositions, kits, and methods that include such novel enzymes. Accordingly, the present invention provides, in certain embodiments, mutant reverse transcriptase enzymes that exhibit increased thermostability, increased thermoreactivity, and/or increased speed, as well as additional beneficial properties such as improved inhibitor resistance, for example resistance to polyphenol-like compounds, improved cDNA generation with difficult RNA templates, and increased specificity; and to methods of producing, such as by reverse transcribing, amplifying or sequencing nucleic acid molecules, for example mRNA molecules, using such reverse transcriptase enzymes. In illustrative embodiments, mutant reverse transcriptases of the present invention include two or more of the aforementioned properties. Mutant reverse transcriptases with other beneficial properties are provided herein, some of which include one or more of the additional aforementioned properties. In certain embodiments, the invention provides kits and compositions, such as storage compositions and reaction mixtures, which include the mutant reverse transcriptases provided herein.

In certain illustrative embodiments, the mutant reverse transcriptases provide increased efficiency in reverse transcription, especially with regard to reverse transcription carried out at elevated temperatures. Accordingly, in certain illustrative embodiments, the present invention provides mutant reverse transcriptases wherein one or more amino acid changes have been made which renders the enzyme more thermostable and/or thermoreactive during nucleic acid synthesis reactions.

In some embodiments, the present invention is directed to mutant reverse transcriptases derived from Maloney Murine Leukemia Virus (M-MLV) reverse transcriptase. In particular, the present invention provides reverse transcriptases having improved thermostability by substituting one or more amino acid residues of the wild type amino acid sequence of M-MLV reverse transcriptase represented by SEQ. ID. NO: 2 with other amino acid residues. In some embodiments, the amino acid positions targeted for mutation or modification to produce higher thermostability and/or thermoreactivity (as well as other properties disclosed herein) are listed in Table 1. For example, the present invention includes M-MLV reverse transcriptases having specific mutations (or combinations thereof) at amino acid positions corresponding to wild type M-MLV selected from the group consisting of: P51, S67, E69, T197, H204, E302, F309, W313, T330, L435, N454, D524, D583, H594, D653, and/or L671. In a preferred embodiment of the present invention, M-MLV reverse transcriptases are provided having all of the following mutations P51L, S67R, E69K, T197A, H204R, E302K, F309N, W313F, T330P, L435G, N454K, D524G, D583N, H594Q, D653N, and L671P. In some embodiments, reverse transcriptases of the invention also preferably have reduced or substantially reduced RNase H activity.

Similar or equivalent sites of corresponding amino acid positions in reverse transcriptases from other species can be mutated to produce thermostable and/or thermoreactive reverse transcriptases as disclosed herein. For example, in some embodiments the present invention provides reverse transcriptases having at least 50% (e.g., 50%, 55%, 60%, 65%, 70%, 75%, 80%, 85%, 90%, 91%, 92%, 93%, 94%, 95%, 96%, etc.) amino acid sequence identity to SEQ ID NO:4.

In some embodiments, the mutant M-MLV reverse transcriptases of the present invention exhibit increased reverse transcriptases activity at a reaction temperature of at least 50° C. (e.g., 50° C., 55° C., 60° C., 65° C., 70° C., and 75° C.) when compared to wild type M-MLV. For example, in some embodiments, the increased reverse transcriptase activity at 50° C. to 60° C. is at least 10%, 25%, 50%, 75%, 100%, or 200% more compared to wild type M-MLV at an even lower reaction temperature (e.g., 37° C.). Likewise, in some embodiments, reverse transcriptases of the present invention retain at least 50% (e.g., 50%, 70%, 80%, 90%, etc.) reverse transcriptase activity at 50° C. to 60° C. for at least 5 minutes. In other embodiments, the reverse transcriptases retain at least 50% activity after heating to at least 50° C.) for at least 5 minutes. Similarly, in other embodiments, the reverse transcriptases as described herein retain at least 50% (e.g., 50%, 70%, 80%, 90%, etc.) activity after heating to at least 50° C. for at least 10 minutes (e.g., 10 minutes, 15 minutes, 60 minutes, etc.) at a pH ranging from about 7.3 to 8.3 when compared to wild type M-MLV at an even lower reaction temperature (e.g., 37° C.) under similar pH conditions.

In some embodiments, the reverse transcriptases of the present invention are able to produce a cDNA that is at least 7.5 kb within 5 minutes at a reaction temperature of about 60° C. In other embodiments, reverse transcriptases of the present invention are able to produce a cDNA that is at least 9.5 kb within 15 minutes at a reaction temperature of about 60° C.

The present invention is also directed to DNA molecules (preferably vectors) containing a gene or nucleic acid molecule encoding the mutant reverse transcriptases of the present invention and to host cells containing such DNA molecules. Any number of hosts may be used to express the gene or nucleic acid molecule of interest, including prokaryotic and eukaryotic cells. Preferably, prokaryotic cells are used to express the polymerases of the invention. The preferred prokaryotic host according to the present invention is *E. coli*.

The invention also provides compositions and reaction mixtures for use in reverse transcription of nucleic acid molecules, comprising one or more mutant or modified reverse transcriptase enzymes or polypeptides as disclosed herein. Such compositions may further comprise one or more nucleotides, a suitable buffer, and/or one or more DNA polymerases. The compositions of the invention may also comprise one or more oligonucleotide primers or terminating agents (e.g., dideoxynucleotides). Such compositions may also comprise a stabilizing agent, such as glycerol or a surfactant. Such compositions may further comprise the use of hot start mechanisms to prevent or reduce unwanted polymerization products during nucleic acid synthesis.

The invention provides in certain embodiments, compositions that include one or more reverse transcriptases of the invention and one or more DNA polymerases for use in amplification reactions. Such compositions may further comprise one or more nucleotides and/or a buffer suitable for amplification. The compositions of the invention may also comprise one or more oligonucleotide primers. Such compositions may also comprise a stabilizing agent, such as glycerol or a surfactant. Such compositions may further comprise the use of one or more hot start mechanisms to prevent or reduce unwanted polymerization products during nucleic acid synthesis.

The invention further provides methods for synthesis of nucleic acid molecules using one or more mutant reverse transcriptase enzymes or polypeptides as disclosed herein. In particular, the invention is directed to methods for making one or more nucleic acid molecules, comprising mixing one or more nucleic acid templates (preferably one or more RNA templates and most preferably one or more messenger RNA templates) with one or more reverse transcriptases of the invention and incubating the mixture under conditions sufficient to make a first nucleic acid molecule or molecules complementary to all or a portion of the one or more nucleic acid templates. In some embodiments, the first nucleic acid molecule is a single-stranded cDNA. Nucleic acid templates suitable for reverse transcription according to this aspect of the invention include any nucleic acid molecule or population of nucleic acid molecules (preferably RNA and most preferably mRNA), particularly those derived from a cell or tissue. In some embodiments, cellular sources of nucleic acid templates include, but are not limited to, bacterial cells, fungal cells, plant cells and animal cells.

In certain embodiments, the invention provides methods for making one or more double-stranded nucleic acid molecules. Such methods comprise (a) mixing one or more nucleic acid templates (preferably RNA or mRNA, and more preferably a population of mRNA templates) with one or more reverse transcriptases of the invention; (b) incubating the mixture under conditions sufficient to make a first nucleic acid molecule or molecules complementary to all or a portion of the one or more templates; and (c) incubating the first nucleic acid molecule or molecules under conditions sufficient to make a second nucleic acid molecule or molecules complementary to all or a portion of the first nucleic acid molecule or molecules, thereby forming one or more double-stranded nucleic acid molecules comprising the first and second nucleic acid molecules. Such methods may include the use of one or more DNA polymerases as part of the process of making the one or more double-stranded nucleic acid molecules. The invention also concerns compositions useful for making such double-stranded nucleic acid molecules. Such compositions comprise one or more reverse transcriptases of the invention and optionally one or more DNA polymerases, a suitable buffer, one or more primers, and/or one or more nucleotides.

The invention also provides methods for amplifying a nucleic acid molecule. Such amplification methods comprise mixing the double-stranded nucleic acid molecule or molecules produced as described above with one or more DNA polymerases and incubating the mixture under conditions sufficient to amplify the double-stranded nucleic acid molecule. In a first preferred embodiment, the invention concerns a method for amplifying a nucleic acid molecule, the method comprising (a) mixing one or more nucleic acid templates (preferably one or more RNA or mRNA templates and more preferably a population of mRNA templates) with one or more reverse transcriptases of the invention and with one or more DNA polymerases and (b) incubating the mixture under conditions sufficient to amplify nucleic acid molecules complementary to all or a portion of the one or more templates.

The invention is also directed to methods for reverse transcription of one or more nucleic acid molecules comprising mixing one or more nucleic acid templates, which are preferably RNA or messenger RNA (mRNA) and more preferably a population of mRNA molecules, with one or more reverse transcriptase of the present invention and incubating the mixture under conditions sufficient to make a nucleic acid molecule or molecules complementary to all or a portion of the one or more templates. To make the nucleic acid molecule or molecules complementary to the one or more templates, a primer (e.g., an oligo(dT) primer) and one or more nucleotides are preferably used for nucleic acid synthesis in the 5 to 3 direction. Nucleic acid molecules suitable for reverse transcription according to this aspect of the invention include any nucleic acid molecule, particularly those derived from a prokaryotic or eukaryotic cell. Such cells may include normal cells, diseased cells, transformed cells, established cells, progenitor cells, precursor cells, fetal cells, embryonic cells, bacterial cells, yeast cells, animal cells (including human cells), avian cells, plant cells and the like, or tissue isolated from a plant or an animal (e.g., human, cow, pig, mouse, sheep, horse, monkey, canine, feline, rat, rabbit, bird, fish, insect, etc.). Nucleic acid molecules suitable for reverse transcription may also be isolated and/or obtained from viruses and/or virally infected cells.

The invention further provides methods for amplifying or sequencing a nucleic acid molecule comprising contacting the nucleic acid molecule with a reverse transcriptase of the present invention. In some embodiments, such methods comprise one or more polymerase chain reactions (PCRs). In some embodiments, a reverse transcription reaction is coupled to a PCR, such as in RT-PCR.

The present invention also provides kits for reverse transcription comprising the reverse transcriptase of the present invention in a packaged format. The kit for reverse transcription of the present invention can include, for example, the reverse transcriptase, any conventional constituent necessary for reverse transcription such as a nucleotide primer, at least one dNTP, and a reaction buffer, and optionally a DNA polymerase.

The invention is also directed to kits for use in the methods of the invention. Such kits can be used for making, sequencing or amplifying nucleic acid molecules (single- or double-stranded). The kits of the invention comprise a carrier, such as a box or carton, having in close confinement therein one or more containers, such as vials, tubes, bottles and the like. In certain embodiments of the kits of the invention, a first container contains one or more of the reverse transcriptase enzymes of the present invention. The kits of the invention may also comprise, in the same or different containers, one or more DNA polymerase (preferably thermostable DNA polymerases), one or more suitable buffers for nucleic acid synthesis and one or more nucleotides. Alternatively, the components of the kit may be divided into separate containers (e.g., one container for each enzyme and/or component). The kits of the invention also may comprise instructions or protocols for carrying out the methods of the invention. In preferred kits of the invention, the reverse transcriptases are mutated such that the temperature at which cDNA synthesis occurs is increased. In additional preferred kits of the invention, the enzymes (reverse transcriptases and/or DNA polymerases) in the containers are present at working concentrations.

Thus, as described in detail above, in one aspect, mutant M-MLV reverse transcriptases are provided. Such reverse transcriptases comprise at least one mutation at an amino acid position corresponding to the sequence for wild type M-MLV reverse transcriptase (SEQ ID NO:2), wherein at least one amino acid position is selected from: S67, T197, and E302. In some embodiments, the at least one mutation is selected from the following amino acid substitution mutations: (S67R, S67N, or S67K), (T197A, T197S, or T197G), and (E302K, E302R, or E302G). In some embodiments, the mutant reverse transcriptases further comprises at least one additional mutation at an amino acid position selected from: P51, E69, P196, D200, H204, M289, T306, F309, W313, T330, L435, N454, D524, E562, D583, H594, L603, D653, and L671. In some embodiments, the at least one additional mutation is selected from the following amino acid substitution mutations: P51L, E69K, P196S, D200N, H204R, M289L, T306K, (F309N, F309Y, or F309I), (W313F, W313L, or W313C), T330P, (L435G, L435V, or L435R), N454K, D524G, E562Q, D583N, H594Q, L603W, (D653N or D653H), and L671P.

In another aspect, mutant M-MLV reverse transcriptases are provided that comprise at least six mutations at an amino acid position corresponding to the sequence for wild type M-MLV reverse transcriptase (SEQ ID NO:2), wherein at least six amino acid positions are selected from: P51, E69, P196, D200, H204, M289, T306, F309, W313, T330, L435, N454, D524, E562, D583, H594, L603, D653, and L671. In some embodiments, the at least six mutations are selected from the following amino acid substitutions: P51L, E69K, P196S, D200N, H204R, M289L, T306K, (F309N, F309Y, or F309I), (W313F, W313L, or W313C), T330P, (L435G, L435V, or L435R), N454K, D524G, E562Q, D583N, H594Q, L603W, (D653N or D653H), and L671P. In some embodiments, the mutant M-MLV reverse transcriptases further comprise at least one additional mutation at an amino acid position selected from: S67, T197, and E302. In some embodiments, the at least one additional mutation is selected from the following amino acid substitutions: (S67R, S67N, or S67K), (T197A, T197S, or T197G), and (E302K, E302R, or E302G).

In some embodiments, mutant M-MLV reverse transcriptases are provided that have a mutation at each of the amino acid positions: P51, S67, E69, T197, H204, E302, F309, W313, T330, L435, N454, D524, D583, H594, D653, and L671. In some embodiments, the mutant M-MLV reverse transcriptase comprises each of the following amino acid substitution mutations: P51L, S67R, E69K, T197A, H204R, E302K, F309N, W313F, T330P, L435G, N454K, D524G, D583N, H594Q, D653N, and L671P.

In some embodiments, the mutant M-MLV reverse transcriptases lack RNase H activity. In yet other embodiments, the mutant M-MLV reverse transcriptases demonstrate increased reverse transcriptase activity at a reaction temperature of at least 50° C. compared to reverse transcriptase activity of the corresponding wild type M-MLV reverse transcriptase. In some embodiments, the mutant M-MLV reverse transcriptases demonstrate increased reverse transcriptase activity that is at least 10% (e.g., 10%, 25%, 50%, 75%, 80%, 90%, 100%, 200%, etc.) more than wild type M-MLV reverse transcriptase activity. In some embodiments, the mutant M-MLV reverse transcriptases possess reverse transcriptase activity after 5 minutes at 60° C. that is at least 25% (e.g., 50%, 100%, 200%, etc.) of the reverse transcriptase activity of wild type M-MLV reverse transcriptase after 5 minutes at 37° C. In some embodiments, the mutant M-MLV reverse transcriptases, demonstrate one or more of the following properties: increased thermostability; increased thermoreactivity; increased resistance to reverse transcriptase inhibitors; increased ability to reverse transcribe difficult templates, increased speed/processivity; and increased specificity (e.g., decreased primer-less reverse transcription).

In another aspect, mutant reverse transcriptases are provided that comprise at least 50% (e.g., 50%, 60%, 705, 80%, 90%, 95%, etc.) amino acid sequence identity to SEQ ID NO:4. In some embodiments, the mutant reverse transcriptases comprise SEQ ID NO:4. In some embodiments, the mutant reverse transcriptases consist of SEQ ID NO:4.

In some embodiments, the mutant reverse transcriptases are thermostable at temperatures between 50° C. to 65° C. (e.g. 50° C., 52° C., 55° C., 58° C., 60° C., and 62° C.). In some embodiments, they are thermostable for at least 1 minute (e.g., 1 minute, 5 minutes, 15 minutes, 60 minutes, 120 minutes, etc.) at a temperature between 50° C. to 65° C. (e.g., 55° C., 60° C., etc.). In some embodiments, the mutant reverse transcriptases are thermoreactive at temperatures between 50° C. to 65° C. (e.g. 50° C., 52° C., 55° C., 58° C., 60° C., and 62° C.). In some embodiments, the mutant reverse transcriptase are thermoreactive for at least 1 minute (e.g., 1 minute, 5 minutes, 15 minutes, 60 minutes, 120 minutes, etc.) at temperatures between 50° C. to 65° C. (e.g., 55° C., 60° C., etc.). In some embodiments, the mutant reverse transcriptases retain at least 10% (e.g., 10%, 20%, 30%, 40%, 50%, 60%, 70%, 80%, 90%, and 100%) reverse transcriptase activity after heating to at least 50° C. (e.g., 50° C., 55° C., 60° C., 62° C., 65° C., etc.) for at least 1 minute (e.g., 1 minute, 2 minutes, 5 minutes, 10 minutes, 15 minutes, etc.). In some embodiments, the reverse transcriptases retain at least 10% (e.g., 10%, 20%, 30%, 40%, 50%, 60%, 70%, 80%, 90%, and 100%) reverse transcriptase activity after heating to at least 60° C. (e.g., 60° C., 62° C., 65° C., etc.) for at least 1 minute (e.g., 1 minute, 2 minutes, 5 minutes, 10 minutes, 15 minutes, etc.). In some embodiments, the reverse transcriptases retain at least 50% (e.g., 50%, 60%, 70%, 80%, 90%, and 100%) reverse transcriptase activity after heating to at least 50° C. (e.g., 50° C., 55° C., 60° C., 62° C., 65° C., etc.) for at least 1 minute (e.g., 1 minute, 2 minutes, 5 minutes, 10 minutes, 15 minutes, etc.). In some embodiments, the reverse transcriptases retain at least 10% (e.g., 10%, 20%, 30%, 40%, 50%, 60%, 70%, 80%, 90%, and 100%) reverse transcriptase activity after heating to at least 50° C. (e.g., 50° C., 55° C., 60° C., 62° C., 65° C.) for at least 5 minutes (e.g., 5 minutes, 10 minutes, 15 minutes, 30 minutes, etc.).

In some embodiments, the mutant reverse transcriptases are mutant M-MLV reverse transcriptases. In other embodiments, the mutant reverse transcriptases are mutant reverse transcriptases obtained from other species, including for example, fowl pox, wild boar, koala and baboon. In some embodiments, the mutant reverse transcriptases comprise regions of amino acid homology and identity, such as that depicted by the consensus sequence listed in FIGS. 1A through 1D.

In another aspect, compositions for nucleic acid synthesis are provided. Such compositions can comprise a buffer and any of the mutant reverse transcriptases described herein. In some embodiments, the compositions further comprise one or more components useful for nucleic acid synthesis, such as one or more nucleotides, one or more DNA polymerases, one or more detergents, one or more primers, one or more hot start components, and/or one or more terminating agents. In some embodiments, the termination agent is a dideoxynucleotide.

In another aspect, methods for nucleic acid synthesis (such as reverse transcription and amplification) are provided. Such methods can comprise the use of any of the mutant reverse transcriptases described herein. In some embodiments, the methods comprise: (a) preparing a mixture comprising one or more nucleic acid templates with one or more reverse transcriptases as described herein; and (b) incubating the mixture under conditions sufficient to make one or more first nucleic acid molecules complementary to all or a portion of the one or more nucleic acid templates.

In other embodiments, the methods comprise: (a) mixing one or more nucleic acid templates with one or more reverse transcriptases as described herein and one or more DNA polymerases; and (b) incubating the mixture under conditions sufficient to amplify one or more nucleic acid molecules complementary to all or a portion of the one or more templates.

In some embodiments, the nucleic acid template is a messenger RNA molecule or a population of mRNA molecules. In some embodiments, the methods comprise a step of incubating one or more first nucleic acid molecules under conditions sufficient to make one or more second nucleic acid molecules complementary to all or a portion of the one or more first nucleic acid molecules. In other embodiments, the methods further comprise a step of determining the nucleotide sequence of all or a portion of the amplified nucleic acid molecules that are complementary to all or a portion of the one or more templates. In some embodiments of the described methods, incubating is performed at a temperature of about 60° C.

In another aspect, kits comprising mutant M-MLV reverse transcriptases as described herein in one or more packaged containers are provided.

In yet another aspect, isolated nucleic acids encoding mutant reverse transcriptases as described herein are provided.

In another aspect, vectors comprising nucleic acids encoding mutant reverse transcriptases as described herein are provided. In one embodiment, expression vectors comprising a promoter operably linked to nucleic acids encoding mutant reverse transcriptases as described herein are provided.

In another aspect, host cells comprising nucleic acids encoding mutant reverse transcriptases as described herein are provided. In another aspect, host cells comprising mutant reverse transcriptases or polypeptides having reverse transcriptase activity as described herein are provided.

Other preferred embodiments of the present invention will be apparent to one of ordinary skill in light of the following drawings and description of the invention, and of the claims.

BRIEF DESCRIPTION OF THE DRAWINGS

These and other features, aspects, and advantages of the present invention will become better understood with reference to the following description and appended claims, and accompanying drawings where:

Figure 1A:
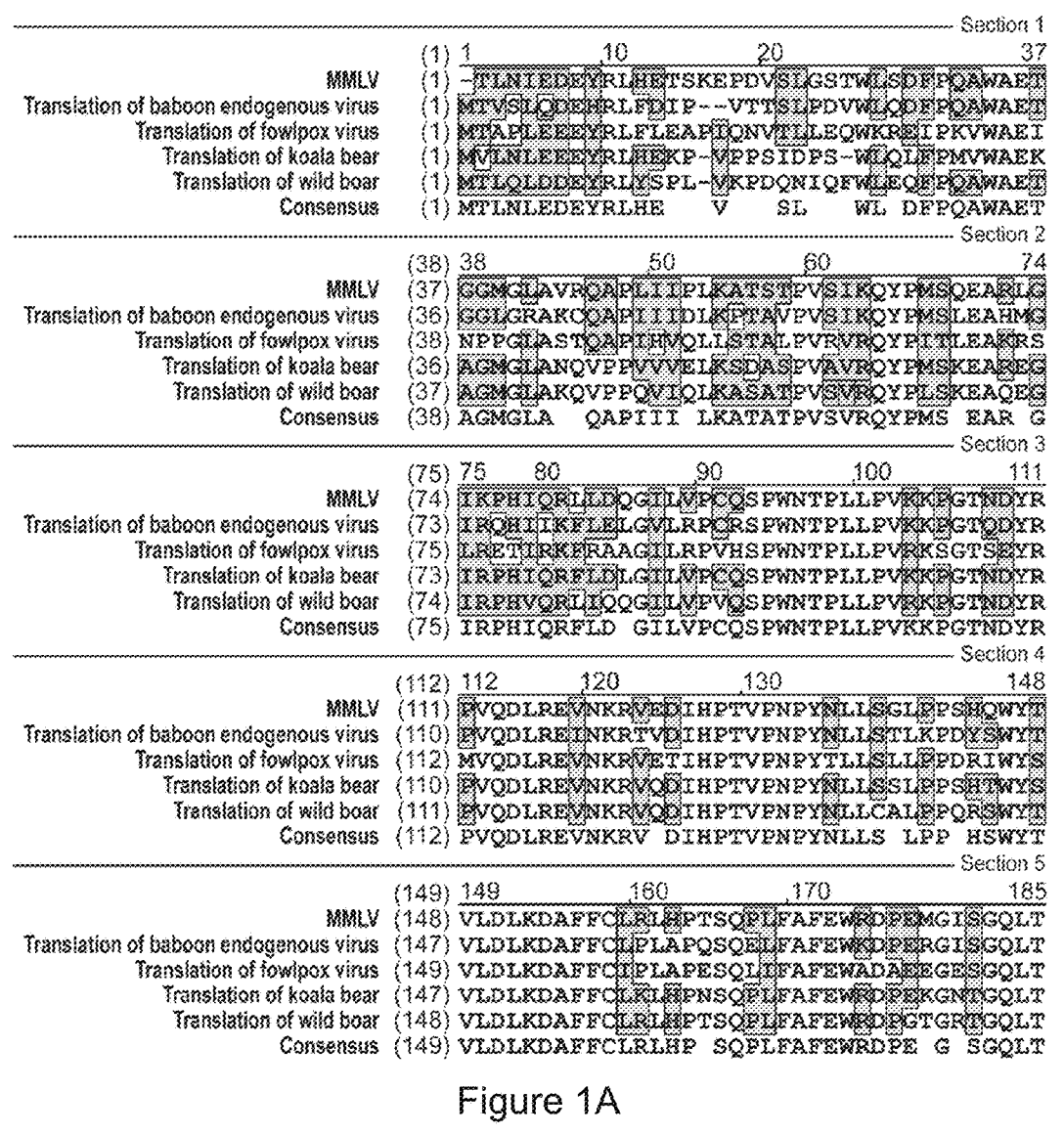
Figure 1B:
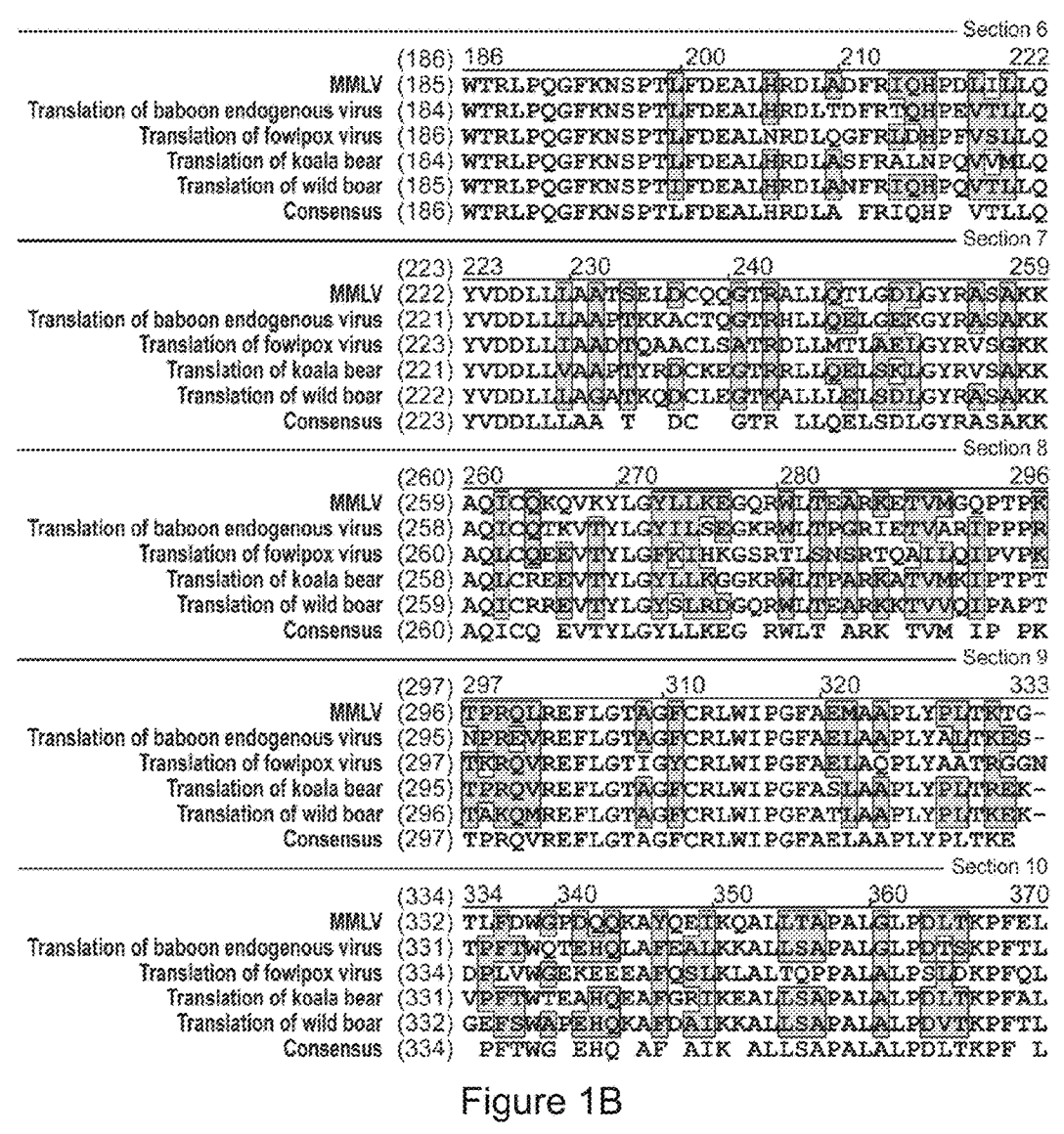
Figure 1C:
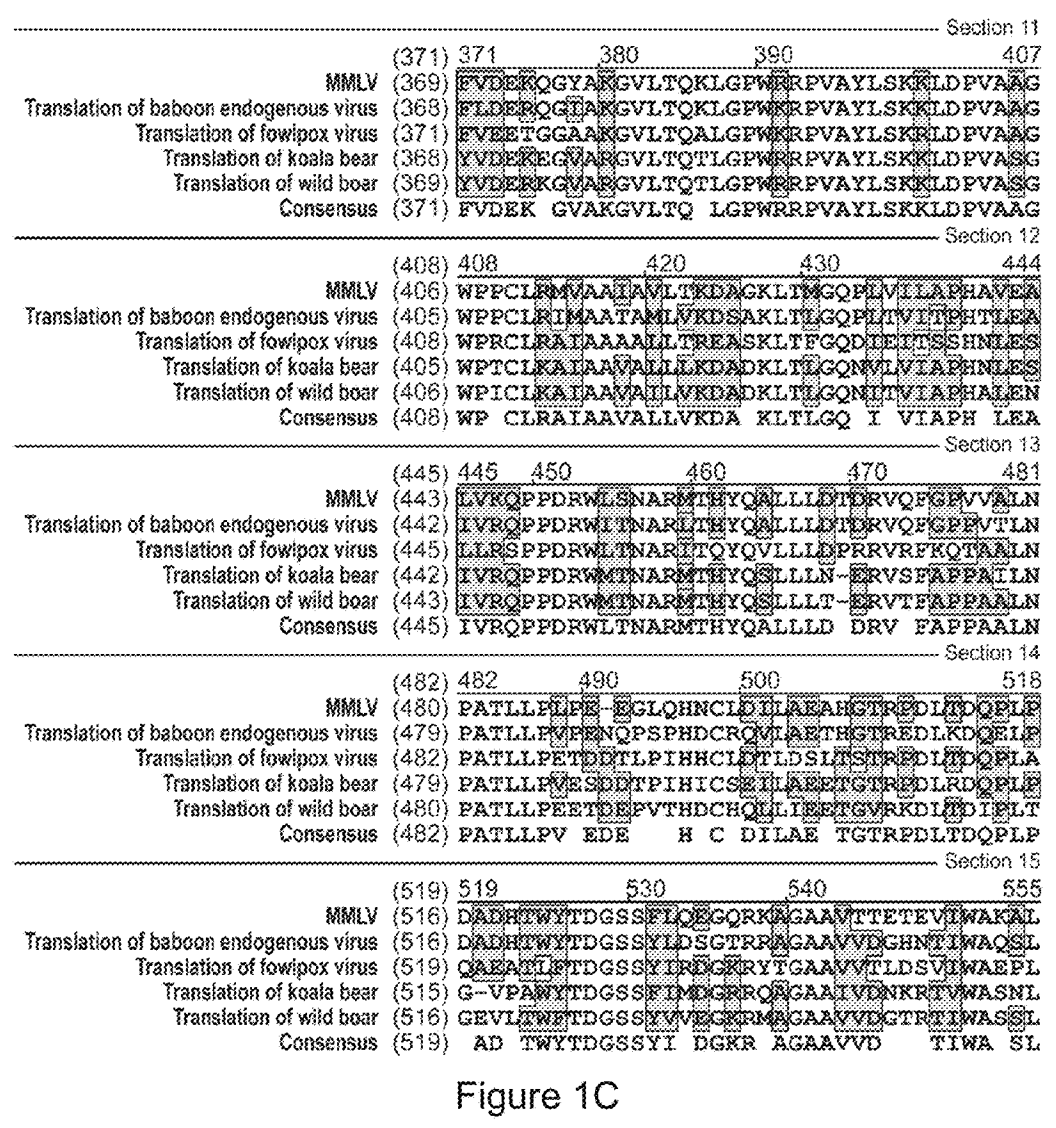

FIGS. 1A through 1D show a table comprising the amino acid sequence alignment between wild type M-MLV reverse transcriptase (MMLV) (SEQ ID NO: 16) and viral reverse transcriptases specific to other species of animals (i.e., baboon (SEQ ID NO: 17), fowl pox (SEQ ID NO: 18), koala (SEQ ID NO: 19), and wild boar (SEQ ID NO: 20)). Regions of amino acid similarity and identity are seen throughout the various RTs. A consensus sequence among the various RTs is also shown.

Figure 8A:
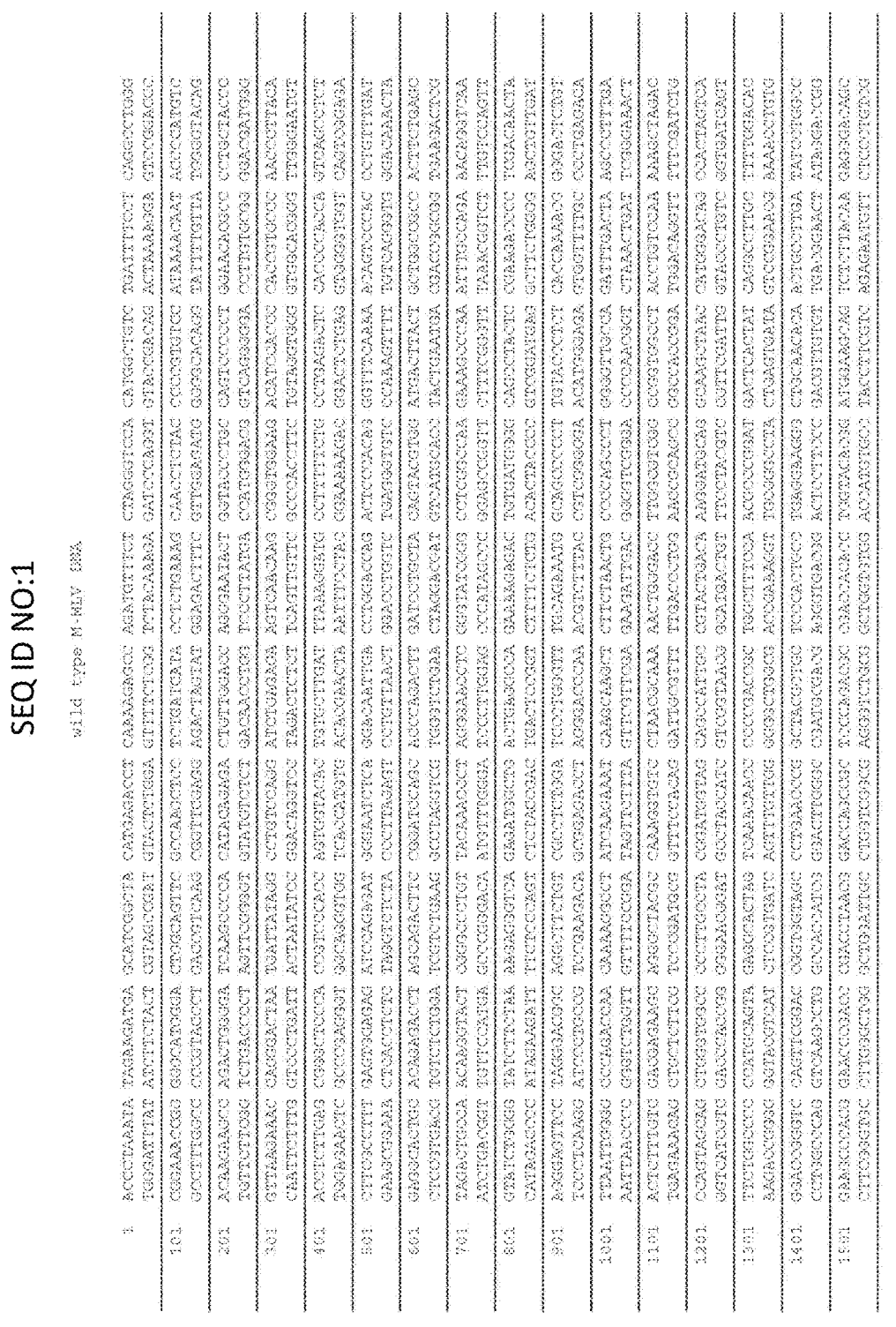

FIGS. 8A and 8B list the nucleic acid sequence for wild type M-MLV reverse transcriptase (SEQ ID NO:1)

FIG. 9 lists the amino acid sequence for wild type M-MLV reverse transcriptase (SEQ ID NO:2)

FIGS. 10A and 10B list the nucleic acid sequence for an exemplary mutant ("Mut D9") M-MLV reverse transcriptase (SEQ ID NO:3) of the invention.

FIG. 11 lists the amino acid sequence for an exemplary mutant ("Mut D9") M-MLV reverse transcriptase (SEQ ID NO:4) of the invention.

DETAILED DESCRIPTION

Figure 2:
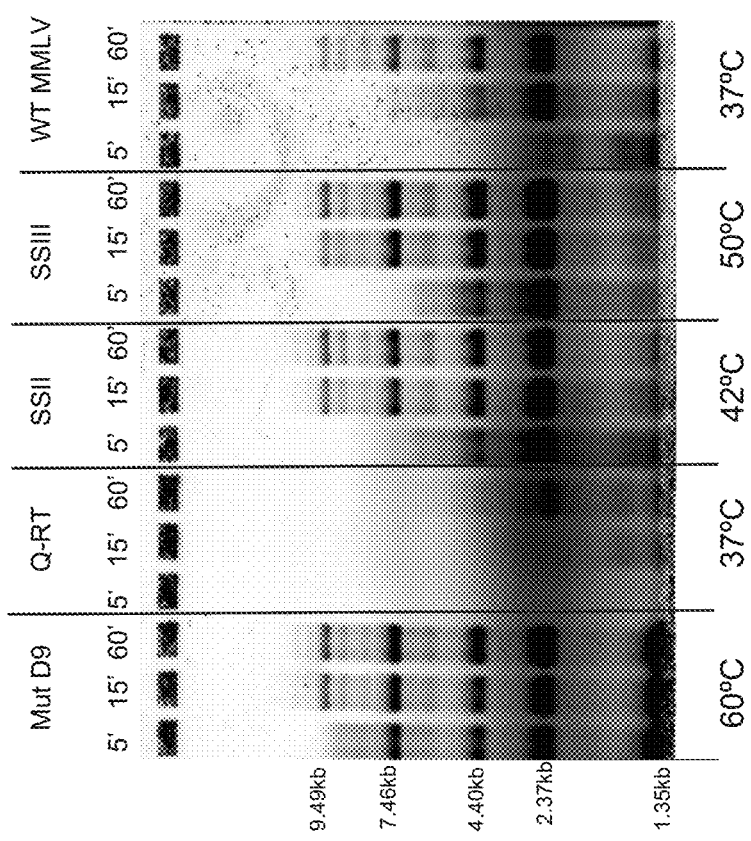
FIG. 2 is a fluorescent image showing RT activity of an exemplary mutant M-MLV reverse transcriptase as disclosed herein ("Mut D9"; SEQ ID NO:4) compared to wild type M-MLV reverse transcriptase ("WT MMLV"; SEQ ID NO:2) as well as other commercially available ("conventional") mutant M-MLV reverse transcriptases ("SSII", "SSW", and "Q-RT"). Each lane shows the cDNA products obtained from RT reactions carried out for varying lengths of time (i.e., 5 minutes, 15 minutes or 60 minutes) and under varying reaction temperatures (i.e., 37° C., 42° C., 50° C. or 60° C.), as indicated. A 0.24 to 9.5 kb RNA ladder was used as the template nucleic acid for each reaction.

Provided herein are reverse transcriptases that have been mutated to increase thermostability and/or thermoreactivity, reverse transcriptase inhibitor resistance, cDNA generation with difficult RNA templates, and specificity. In certain embodiments, the invention provides methods of making such reverse transcriptases by mutating or modifying specific amino acids of the corresponding wild type reverse transcriptases. In other embodiments, the invention provides methods of producing, amplifying and/or sequencing nucleic acid molecules, in illustrative embodiments, cDNA molecules, using compositions and/or reactions mixtures containing such mutant reverse transcriptase enzymes. For example, the reverse transcriptases of the invention are well-suited for nucleic acid synthesis methods including, but not limited to, RNA sequencing and reverse transcription of crude samples, difficult RNA templates and gene specific sequences.

DEFINITIONS

In the description that follows, a number of terms are used that have the following meaning:

Operably linked. As used herein "operably linked" means that a nucleic acid element is positioned so as to influence the initiation of expression of the polypeptide encoded by the structural gene or other nucleic acid molecule.

Substantially Pure. As used herein "substantially pure" means that the desired material is essentially free from contaminating cellular components which are associated with the desired material in nature. In a preferred aspect, a reverse transcriptase of the invention has 25% or less, preferably 15% or less, more preferably 10% or less, more preferably 5% or less, and still more preferably 1% or less contaminating cellular components. In another aspect, the reverse transcriptases of the invention have no detectable protein contaminants when 200 units of reverse transcriptase are run on a protein gel (e.g., SDS-PAGE) and stained with Coomassie blue. Contaminating cellular components may include, but are not limited to, enzymatic activities such as phosphatases, exonucleases, endonucleases or undesirable DNA polymerase enzymes. Preferably, reverse transcriptases of the invention are substantially pure.

Substantially isolated. As used herein "substantially isolated" means that the polypeptide of the invention is essentially free from contaminating proteins, which may be associated with the polypeptide of the invention in nature and/or in a recombinant host. In one aspect, a substantially isolated reverse transcriptase of the invention has 25% or less, preferably 15% or less, more preferably 10% or less, more preferably 5% or less, and still more preferably 1% or less contaminating proteins. In another aspect, in a sample of a substantially isolated polypeptide of the invention, 75% or greater (preferably 80%, 85%, 90%, 95%, 98%, or 99% or greater) of the protein in the sample is the desired reverse transcriptase of the invention. The percentage of contaminating protein and/or protein of interest in a sample may be determined using techniques known in the art, for example, by using a protein gel (e.g., SDS-PAGE) and staining the gel with a protein dye (e.g., Coomassie blue, silver stain, amido black, etc.). In another aspect, the reverse transcriptases of the invention have no detectable protein contaminants when 200 units of reverse transcriptase are run on a protein gel (e.g., SDS-PAGE) and stained with Coomassie blue.

Terminating agent. The term "terminating agent" which is sometimes used interchangeably with "terminator base" refers to a nucleotide which is incapable of being extended by a DNA or RNA polymerase. Such nucleotides can include, for example, dideoxynucleotides (ddNTPs) or various sugar-modified nucleotides.

Reverse Transcriptase. As used herein, the term "reverse transcriptase" refers to a protein, polypeptide, or polypeptide fragment that exhibits reverse transcriptase activity.

Reverse Transcriptase Activity. As used herein, the term "reverse transcriptase activity," "reverse transcription activity," or "reverse transcription" indicates the capability of an enzyme to synthesize DNA strand (that is, complementary DNA or cDNA) using RNA as a template.

Mutation. As used herein, the term "mutation" or "mutant" indicates a change or changes introduced in a wild type DNA sequence or a wild type amino acid sequence. Examples of mutations include, but are not limited to, substitutions, insertions, deletions, and point mutations. Mutations can be made either at the nucleic acid level or at the amino acid level.

Thermostable. For the purposes of this disclosure, "thermostable" generally refers to an enzyme, such as a reverse transcriptase ("thermostable reverse transcriptase"), which retains a greater percentage or amount of its activity after a heat treatment than is retained by the same enzyme having wild type thermostability, after an identical treatment. Thus, a reverse transcriptase having increased/enhanced thermostability may be defined as a reverse transcriptase having any increase in thermostability, preferably from about 1.2 to about 10,000 fold, from about 1.5 to about 10,000 fold, from about 2 to about 5,000 fold, or from about 2 to about 2000 fold (preferably greater than about 5 fold, more preferably greater than about 10 fold, still more preferably greater than about 50 fold, still more preferably greater than about 100 fold still more preferably greater than about 500 fold, and most preferably greater than about 1000 fold) retention of activity after a heat treatment sufficient to cause a reduction in the activity of a reverse transcriptase that is wild type for thermostability. Preferably, the mutant reverse transcriptase of the invention is compared to the corresponding un-mutated or wild type reverse transcriptase to determine the relative enhancement or increase in thermostability. For example, after a heat treatment at 60° C. for 5 minutes, a thermostable reverse transcriptase may retain approximately 90% of the activity present before the heat treatment, whereas a reverse transcriptase that is wild type for thermostability may retain 10% of its original activity. Likewise, after a heat treatment at 60° C. for 15 minutes, a thermostable reverse transcriptase may retain approximately 80% of its original activity, whereas a reverse transcriptase that is wild type for thermostability may have no measurable activity. Similarly, after a heat treatment at 60° C. for 15 minutes, a thermostable reverse transcriptase may retain approximately 50%, approximately 55%, approximately 60%, approximately 65%, approximately 70%, approximately 75%, approximately 80%, approximately 85%, approximately 90%, or approximately 95% of its original activity, whereas a reverse transcriptase that is wild type for thermostability may have no measurable activity or may retain 20%, 15%, 10%, or none of its original activity. In the first instance (i.e., after heat treatment at 60° C. for 5 minutes), the thermostable reverse transcriptase would be said to be 9-fold more thermostable than the wild type reverse transcriptase (90% compared to 10%). Examples of conditions which may be used to measure thermostability of an enzyme such as reverse transcriptases are set out in further detail below and in the Examples.

The thermostability of a reverse transcriptase can be determined, for example, by comparing the residual activity of a reverse transcriptase that has been subjected to a heat treatment, e.g., incubated at 60° C. for a given period of time, for example, five minutes, to a control sample of the same reverse transcriptase that has been incubated at room temperature for the same length of time as the heat treatment. Typically the residual activity may be measured by following the incorporation of a radiolabeled deoxyribonucleotide into an oligodeoxyribonucleotide primer using a complementary oligoribonucleotide template. For example, the ability of the reverse transcriptase to incorporate $[\alpha\text{-}^{32}P]$-dGTP into an oligo-dG primer using a poly(riboC) template may be assayed to determine the residual activity of the reverse transcriptase. Other methods for measuring residual activity are known by those of skill in the art, such as by incorporation of unlabeled nucleotides into a fluorescently-labeled primer. See, for example, Nikiforov, T. T., Anal Biochem., 2011, 412(2): 229-36, which is hereby incorporated by reference.

In another aspect, thermostable reverse transcriptases of the invention may include any reverse transcriptase which is inactivated at a higher temperature compared to the corresponding wild type, un-mutated reverse transcriptase. Preferably, the inactivation temperature for the thermostable reverse transcriptases of the invention is from about 2° C. to about 50° C. (e.g., about 2° C., about 4° C., about 6° C., about 8° C., about 10° C., about 12° C., about 14° C., about 16° C., about 18° C., about 19° C., about 20° C., about 21° C., about 22° C., about 23° C., about 24° C., about 26° C., about 28° C., about 30° C., about 32° C., about 34° C., about 36° C., about 38° C., 40° C., about 42° C., about 44° C., about 46° C., about 48° C., or about 50° C.) higher than the inactivation temperature for the corresponding wild type, un-mutated reverse transcriptase. More preferably, the inactivation temperature for the reverse transcriptases of the invention is from about 5° C. to about 50° C., from about 5° C. to about 40° C., from about 5° C. to about 30° C., or from about 5° C. to about 25° C. greater than the inactivation temperature for the corresponding wild type, un-mutated reverse transcriptase, when compared under the same conditions. In some embodiments, mutant reverse transcriptases of the invention possess reverse transcriptase activity after at least one minute (e.g., 1 minute, 2 minutes, 5 minutes, 10 minutes, 15 minutes, 30 minutes, etc. at an elevated temperature (e.g., 50° C., 55° C., 60° C., 65° C.) that is at least 10% (e.g., 10%, 25%, 50%, 75%, 100%, 150%, 200%, 300%, etc.) of the reverse transcriptase activity of wild type reverse transcriptase after 5 minutes at a lower temperature (e.g., 50° C., 45° C., 42° C., 40° C., 37° C.).

The difference in inactivation temperature for the reverse transcriptase of the invention compared to its corresponding wild type, un-mutated reverse transcriptase can be determined by treating samples of such reverse transcriptases at different temperatures for a defined time period and then measuring residual reverse transcriptase activity, if any, after the samples have been heat treated. Determination of the difference or delta in the inactivation temperature between the test reverse transcriptase compared to the wild type, un-mutated control is determined by comparing the difference in temperature at which each reverse transcriptase is inactivated (i.e., no residual reverse transcriptase activity is measurable in the particular assay used). As will be recognized, any number of reverse transcriptase assays may be used to determine the different or delta of inactivation temperatures for any reverse transcriptases tested.

In another aspect, thermostability of a reverse transcriptase of the invention is determined by measuring the half-life of the reverse transcriptase activity of a reverse transcriptase of interest, Such half-life may be compared to a control or wild type reverse transcriptase to determine the difference (or delta) in half-life. Half-life of the reverse transcriptases of the invention are preferably determined at elevated temperatures (e.g., greater than 37° C.) and preferably at temperatures ranging from 40° C. to 80° C., more preferably at temperatures ranging from 45° C. to 75° C., 50° C. to 70° C., 55° C. to 65° C., and 58° C. to 62° C. Preferred half-lives of the reverse transcriptases of the invention may range from 4 minutes to 10 hours, 4 minutes to 7.5 hours, 4 minutes to 5 hours, 4 minutes to 2.5 hours, or 4 minutes to 2 hours, depending upon the temperature used. For example, the reverse transcriptase activity of the reverse transcriptases of the invention may have a half-life of at least 4 minutes, at least 5 minutes, at least 6 minutes, at least 7 minutes, at least 8 minutes, at least 9 minutes, at least 10 minutes, at least 11 minutes, at least 12 minutes, at least 13 minutes, at least 14 minutes, at least 15 minutes, at least 20 minute, at least 25 minutes, at least 30 minutes, at least 40 minutes, at least 50 minutes, at least 60 minutes, at least 70 minutes, at least 80 minutes, at least 90 minutes, at least 100 minutes, at least 115 minutes, at least 125 minutes, at least 150 minutes, at least 175 minutes, at least 200 minutes, at least 225 minutes, at least 250 minutes, at least 275 minutes, at least 300 minutes, at least 400 minutes, at least 500 minutes at temperatures of 48° C., 50° C., 52° C., 54° C., 56° C., 58° C., 60° C., 62° C., 64° C., 66° C., 68° C., and/or 70° C.

Thermoreactivity. As used herein, "thermoreactivity" or "thermoreactive" refers to the ability of a reverse transcriptase to exhibit enzyme activity at elevated temperatures.

Thermostability. As used herein, "thermostability" or "thermostable" refers to the ability to withstand exposure to elevated temperatures, but not necessarily show activity at such elevated temperatures.

Processivity. As used herein, "processivity" refers to the ability of a reverse transcriptase to continuously extend a primer without disassociating from the nucleic acid template. The length of a template an enzyme is capable of replicating (e.g., "X enzyme can polymerase a 9 kb template" or "X enzyme can produce a cDNA that is about 6000 bases in length.") can also be used to describe the processivity of a given enzyme.

Inhibitor resistance. As used herein, "inhibitor resistance" refers to the ability of a reverse transcriptase to perform reverse transcription in the presence of a compound, chemical, protein, buffer, etc. that is typically inhibitory to the reverse transcriptase (prevents or inhibits reverse transcriptase activity).

Fidelity. Fidelity refers to the accuracy of polymerization, or the ability of the reverse transcriptase to discriminate correct from incorrect substrates, (e.g., nucleotides) when synthesizing nucleic acid molecules which are complementary to a template. The higher the fidelity of a reverse transcriptase, the less the reverse transcriptase misincorporates nucleotides in the growing strand during nucleic acid synthesis; that is, an increase or enhancement in fidelity results in a more faithful reverse transcriptase having decreased error rate or decreased misincorporation rate.

About. The term "about" as used herein, means the recited number plus or minus 10%. Thus, "about 100" includes the full range of values within the range of 90 through 110.

Sources of Reverse Transcriptases

In accordance with the invention, mutations or modifications may be made in any reverse transcriptase or polypeptide having reverse transcriptase activity in order to increase the thermostability and/or thermoreactivity of the enzyme, or confer other properties upon the enzyme, such as increased specificity, increased resistance to reverse transcriptase inhibitors, and/or increased ability to generate cDNAs from difficult RNA templates.

Reverse transcriptases for use in the compositions, methods and kits of the invention include any enzyme or polypeptide having reverse transcriptase activity. Such enzymes include, but are not limited to, retroviral reverse transcriptase, retrotransposon reverse transcriptase, hepatitis B reverse transcriptase, cauliflower mosaic virus reverse transcriptase, bacterial reverse transcriptase, Tth DNA polymerase, Taq DNA polymerase (Saiki, R. K., et al., Science 239:487-491 (1988); U.S. Pat. Nos. 4,889,818 and 4,965,188), Tne DNA polymerase (WO 96/10640), Tma DNA polymerase (U.S. Pat. No. 5,374,553) and mutants, fragments, variants or derivatives thereof (see, e.g., commonly owned U.S. Pat. Nos. 5,948,614 and 6,015,668, which are incorporated by reference herein in their entireties).

Preferred reverse transcriptases include retroviral reverse transcriptases such as Maloney Murine Leukemia Virus (M-MLV) reverse transcriptase, Human Immunodeficiency Virus (HIV) reverse transcriptase, Rous sarcoma virus (RSV) reverse transcriptase, Avian Myeloblastosis Virus (AMV) reverse transcriptase, Rous-associated virus (RAV) reverse transcriptase, and Myeloblastosis Associated Virus (MAV) reverse transcriptase or other Avian sarcoma leukosis virus (ASLV) reverse transcriptases. Additional reverse transcriptases which may be mutated to make the reverse transcriptases of the invention include bacterial reverse transcriptases (e.g., *Escherichia coli* reverse transcriptase) (see, e.g., Mao et al., Biochem. Biophys. Res. Commun. 227:489-93 (1996)) and reverse transcriptases of *Saccharomyces cerevisiae* (e.g., reverse transcriptases of the Ty1 or Ty3 retrotransposons) (see, e.g., Cristofari et al., Jour. Biol. Chem. 274:36643-36648 (1999); Mules et al., Jour. Virol. 72:6490-6503 (1998)). Other reverse transcriptases that can be used in accordance with the described invention include, but are not limited to reverse transcriptases isolated from viruses isolated from, for example, baboon, fowl pox, koala bear, and wild boar species.

The present invention further provides polynucleotides which are identical or have the same functions as the reverse transcriptases included in the present invention. The phrase "identical" or "have same functions as" herein indicates that two polynucleotides demonstrate at least 70%, preferably at least 80%, more preferably at least 90%, and most preferably at least 95% amino acid identity when they are properly arranged by a well-informed computerized algorithm.

The invention further includes reverse transcriptases which are 50%, 55%, 60%, 65%, 70%, 75%, 80%, 85%, 90%, 95%, 96%, 97%, 98%, or 99% identical at the amino acid level to a wild type reverse transcriptase (e.g., M-MLV reverse transcriptase enzyme; SEQ ID NO:2), AMV reverse transcriptase, RSV reverse transcriptase, HIV reverse transcriptase, etc.) and exhibit increased thermostability and/or other desired properties of the invention. Also included within the invention are reverse transcriptases which are 70%, 75%, 80%, 85%, 90%, 95%, 96%, 97%, 98%, or 99% identical at the amino acid level to a reverse transcriptase comprising the amino acid sequence set out below in SEQ ID NO:4 and exhibit increased thermostability and/or thermoreactivity.

The invention also includes fragments of reverse transcriptases which comprise at least 200, 250, 300, 350, 400, 450, 500, 550, 600, 650, or 700 amino acid residues and retain one or more activities associated with reverse transcriptases. Such fragments may be obtained by deletion mutation, by recombinant techniques that are routine and well-known in the art, or by enzymatic digestion of the reverse transcriptase(s) of interest using any of a number of well-known proteolytic enzymes. Reverse transcriptase fragments of the invention further comprise polypeptides which are 70%, 75%, 80%, 85%, 90%, 95%, 96%, 97%, 98%, or 99% identical to one or more of the fragments set out above. The invention also concerns various combinations of any number of these fragments.

By a protein or protein fragment having an amino acid sequence at least, for example, 70% "identical" to a reference amino acid sequence it is intended that the amino acid sequence of the protein is identical to the reference sequence except that the protein sequence may include up to 30 amino acid alterations per each 100 amino acids of the amino acid sequence of the reference protein. In other words, to obtain a protein having an amino acid sequence at least 70% identical to a reference amino acid sequence, up to 30% of the amino acid residues in the reference sequence may be deleted or substituted with another amino acid, or a number of amino acids up to 30% of the total amino acid residues in the reference sequence may be inserted into the reference sequence. These alterations of the reference sequence may occur at the amino (N-) and/or carboxy (C-) terminal positions of the reference amino acid sequence and/or anywhere between those terminal positions, interspersed either individually among residues in the reference sequence and/or in one or more contiguous groups within the reference sequence. As a practical matter, whether a given amino acid sequence is, for example, at least 70% identical to the amino acid sequence of a reference protein can be determined conventionally using known computer programs such as those described above for nucleic acid sequence identity determinations, or using the CLUSTAL W program (Thompson, J. D., et al., Nucleic Acids Res. 22:4673-4680 (1994)).

Sequence identity may be determined by comparing a reference sequence or a subsequence of the reference sequence to a test sequence. The reference sequence and the test sequence are optimally aligned over an arbitrary number of residues termed a comparison window. In order to obtain optimal alignment, additions or deletions, such as gaps, may be introduced into the test sequence. The percent sequence identity is determined by determining the number of positions at which the same residue is present in both sequences and dividing the number of matching positions by the total length of the sequences in the comparison window and multiplying by 100 to give the percentage. In addition to the number of matching positions, the number and size of gaps is also considered in calculating the percentage sequence identity.

Sequence identity is typically determined using computer programs. A representative program is the BLAST (Basic Local Alignment Search Tool) program publicly accessible at the National Center for Biotechnology Information (NCBI, http://www.ncbi.nlm.nih.gov/). This program compares segments in a test sequence to sequences in a database to determine the statistical significance of the matches, then identifies and reports only those matches that that are more significant than a threshold level. A suitable version of the BLAST program is one that allows gaps, for example, version 2.X (Altschul, et al., Nucleic Acids Res. 25(17): 3389-402, 1997). Standard BLAST programs for searching nucleotide sequences (blastn) or protein (blastp) may be used. Translated query searches in which the query sequence is translated, i.e., from nucleotide sequence to protein (blastx) or from protein to nucleic acid sequence (tbblastn) may also be used as well as queries in which a nucleotide query sequence is translated into protein sequences in all 6 reading frames and then compared to an NCBI nucleotide database which has been translated in all six reading frames (tbblastx).

Additional suitable programs for identifying proteins with sequence identity or similarity to the proteins of the invention include, but are not limited to, PHI-BLAST (Pattern Hit Initiated BLAST, Zhang, et al., Nucleic Acids Res. 26(17): 3986-90, 1998) and PSI-BLAST (Position-Specific Iterated BLAST, Altschul, et al., Nucleic Acids Res. 25(17):3389-402, 1997).

Programs may be used with default searching parameters. Alternatively, one or more search parameter may be adjusted. Selecting suitable search parameter values is within the abilities of one of ordinary skill in the art.

Some reverse transcriptase enzymes for use in the invention include those that are reduced, substantially reduced, or lacking in RNase H activity. Such enzymes that are reduced or substantially reduced in RNase H activity include RNase H– derivatives of any of the reverse transcriptases described above and may be obtained by mutating, for example, the RNase H domain within the reverse transcriptase of interest, for example, by introducing one or more (e.g., one, two, three, four, five, ten, twelve, fifteen, twenty, thirty, etc.) point mutations, one or more (e.g., one, two, three, four, five, ten, twelve, fifteen, twenty, thirty, etc.) deletion mutations, and/or one or more (e.g., one, two, three, four, five, ten, twelve, fifteen, twenty, thirty, etc.) insertion mutations as described elsewhere herein. For example, such mutations are described in U.S. Pat. Nos. 8,541,219 and 8,753,845, and are herein incorporated by reference in their entirety.

By an enzyme "substantially reduced in RNase H activity" is meant that the enzyme has less than about 30%, less than about 25%, less than about 20%, more preferably less than about 15%, less than about 10%, less than about 7.5%, or less than about 5%, and most preferably less than about 5% or less than about 2%, of the RNase H activity of the corresponding wild type or RNase H+ enzyme, such as wild type Maloney Murine Leukemia Virus (M-MLV), Avian Myeloblastosis Virus (AMV) or Rous Sarcoma Virus (RSV) reverse transcriptases. A reduction in RNase H activity means any reduction in the activity compared, for example, to the corresponding wild type or un-mutated reverse transcriptase. Thus, in one aspect, the reverse transcriptase of the invention can have 50%, 40%, 30%, 20%, 10%, 5%, 1% or no RNase H activity compared to the corresponding wild type reverse transcriptase.

Reverse transcriptases having reduced, substantially reduced, undetectable or lacking RNase H activity have been previously described (see U.S. Pat. No. 5,668,005, U.S. Pat.

No. 6,063,608, and PCT Publication No. WO 98/47912). The RNase H activity of any enzyme may be determined by a variety of assays, such as those described, for example, in U.S. Pat. No. 5,244,797, in Kotewicz, M. L., et al., Nucl. Acids Res. 16:265 (1988), in Gerard, G. F., et al., FOCUS 14(5):91 (1992), in PCT publication number WO 98/47912, and in U.S. Pat. No. 5,668,005, the disclosures of all of which are fully incorporated herein by reference.

Reverse transcriptases having no detectable RNase H activity or lacking RNase H activity by one or more of the described assays are also contemplated in accordance with the invention. Thus, in some embodiments, mutated enzymes for use in the invention include, but are not limited to, M-MLV H– reverse transcriptase, RSV H– reverse transcriptase, AMV H– reverse transcriptase, RAV H– reverse transcriptase, MAV H– reverse transcriptase and HIV H– reverse transcriptase. It will be understood by one of ordinary skill, however, that any enzyme capable of producing a DNA molecule from a ribonucleic acid molecule (i.e., having reverse transcriptase activity) that is reduced or substantially reduced in RNase H activity may be equivalently used in accordance with the invention.

Alternatively, reverse transcriptase enzymes of the invention may not contain any modification or mutation in the RNase H domain which reduces RNase H activity. Thus, in other embodiments, the reverse transcriptases of the invention can have 100% RNase H activity which is equivalent to the corresponding wild type reverse transcriptase.

Reverse transcriptase enzymes or polynucleotides for use in the invention also include those in which terminal deoxynucleotidyl transferase (TdT) activity has been reduced, substantially reduced, or eliminated. Such enzymes that are reduced or substantially reduced in terminal deoxynucleotidyl transferase activity, or in which TdT activity has been eliminated, may be obtained by mutating, for example, amino acid residues within the reverse transcriptase of interest which are in close proximity or in contact with the template-primer, for example, by introducing one or more (e.g., one, two, three, four, five, ten, twelve, fifteen, twenty, thirty, etc.) point mutations, one or more deletion mutations, and/or one or more insertion mutations. Reverse transcriptases which exhibit decreased TdT activity are described in U.S. Pat. No. 7,056,716, issued Jun. 6, 2006 (the entire disclosure of which is incorporated herein by reference).

Enzymes for use in the invention also include those that exhibit increased fidelity. Reverse transcriptases which exhibit increased fidelity are described in U.S. Appl. No. 60/189,454, filed Mar. 15, 2000, and U.S. Pat. No. 7,056,716, issued Jun. 6, 2006 (the entire disclosures of which are incorporated herein by reference).

Thus, in specific embodiments, the invention includes reverse transcriptases which exhibit increased thermostability and/or increased thermoreactivity and, optionally, also exhibit one or more of the following characteristics: (1) reduced or substantially reduced RNase H activity, (2) reduced or substantially reduced TdT activity, and/or (3) increased fidelity.

The present invention further provides nucleic acid molecules which encode the above described mutant reverse transcriptases and reverse transcriptase fragments. In some embodiments, the nucleic acid molecules encoding the mutant reverse transcriptases and reverse transcriptase fragments are at least 80% (e.g., 80%, 85%, 90%, 95%, 99%) identical to SEQ ID NO:3. In some embodiments, the nucleic acid molecules encoding the mutant reverse transcriptases and reverse transcriptase fragments comprise SEQ ID NO:3.

As will be understood by one of ordinary skill in the art, mutated reverse transcriptases in accordance with the invention may be obtained by recombinant or genetic engineering techniques that are routine and well-known in the art (see, e.g., Kotewicz, M. L., et al., Nucl. Acids Res. 16:265 (1988); Soltis, D. A., and Skalka, A. M., Proc. Natl. Acad. Sci. USA 85:3372-3376 (1988)); U.S. Pat. No. 5,668,005; and PCT publication no. WO 98/47912. Mutant reverse transcriptases can, for example, be obtained by mutating the gene(s) or nucleic acid sequences encoding the reverse transcriptase or polynucleotide having reverse transcriptase activity, such as those described above, by site-directed or random mutagenesis. Such mutations may include point mutations, deletion mutations and insertional mutations. Preferably, one or more point mutations (e.g., substitution of one or more amino acids with one or more different amino acids) are used to construct mutant reverse transcriptases of the invention. Fragments of reverse transcriptases may be obtained by deletion mutation by recombinant techniques that are routine and well-known in the art, or by enzymatic digestion of the reverse transcriptase(s) of interest using any of a number of well-known proteolytic enzymes.

To clone a gene or other nucleic acid molecule encoding a reverse transcriptase which will be mutated in accordance with the invention, isolated, DNA which contains the reverse transcriptase gene or open reading frame may be used to construct a recombinant DNA library. Any vector, well known in the art, can be used to clone the reverse transcriptase of interest. However, the vector used must be compatible with the host in which the recombinant vector will be transformed.

The present invention also provides transformants transformed by the expression vector. The transformant of the present invention can be easily constructed by inserting the said expression vector into random prokaryotic cells or eukaryotic cells. The method to introduce a specific vector into cells is well-known to those in the art. In a preferred embodiment of the present invention, a pBAD vector comprising the mutant gene or polynucleotide of the present invention (+/– an additional unrelated sequence, such as a His Tag) is introduced in *E. coli* Top10 cells, leading to the construction of a transformant.

The present invention also provides an expression vector containing the genes or polynucleotides of the present invention. The vector used for the construction of the expression vector of the present invention is not limited, and any conventional vector for the transformation of prokaryotes or eukaryotes can be used. In some embodiments of the present invention, recombinant expression vectors are constructed by inserting a mutant gene represented by SEQ. ID. NO: 3.

Prokaryotic vectors for constructing the plasmid library include plasmids such as those capable of replication in *E. coli* such as, for example, pBR322, ColE1, pSC101, pUC-vectors (pUC18, pUC19, etc.: In: Molecular Cloning, A Laboratory Manual, Cold Spring Harbor Laboratory Press, Cold Spring Harbor, N.Y. (1982); and Sambrook et al., In: Molecular Cloning A Laboratory Manual (2d ed.) Cold Spring Harbor Laboratory Press, Cold Spring Harbor, N.Y. (1989)). *Bacillus* plasmids include pC194, pUB110, pE194, pC221, pC217, etc. Such plasmids are disclosed by Glyczan, T. In: The Molecular Biology Bacilli, Academic Press, York (1982), 307-329. Suitable *Streptomyces* plasmids include pIJ101 (Kendall et al., J. Bacteriol. 169:4177-4183 (1987)).

*Pseudomonas* plasmids are reviewed by John et al., (Rad. Insec. Dis. 8:693-704 (1986)), and Igaki, (Jpn. J. Bacteriol. 33:729-742 (1978)). Broad-host range plasmids or cosmids, such as pCP13 (Darzins and Chakrabarty, J. Bacteriol. 159:9-18 (1984)) can also be used for the present invention. Preferred vectors for cloning the genes and nucleic acid molecules of the present invention are prokaryotic vectors. Preferably, pBAD, pCP13 and pUC vectors are used to clone the genes of the present invention. Other suitable vectors are known to those skilled in the art and are commercially available.

Suitable hosts for cloning the reverse transcriptase genes and nucleic acid molecules of interest are prokaryotic hosts. One example of a prokaryotic host is *E. coli*. However, the desired reverse transcriptase genes and nucleic acid molecules of the present invention may be cloned in other prokaryotic hosts including, but not limited to, hosts in the genera *Escherichia, Bacillus, Streptomyces, Pseudomonas, Salmonella, Serratia,* and *Proteus*. Bacterial hosts of particular interest include *E. coli* DH10B, which may be obtained from Life Technologies, Corp. (Carlsbad, Calif.).

Eukaryotic hosts for cloning and expression of the reverse transcriptase of interest include yeast, fungal, and mammalian cells. Expression of the desired reverse transcriptase in such eukaryotic cells may require the use of eukaryotic regulatory regions which include eukaryotic promoters. Cloning and expressing the reverse transcriptase gene or nucleic acid molecule in eukaryotic cells may be accomplished by well-known techniques using well known eukaryotic vector systems.

Once a DNA library has been constructed in a particular vector, an appropriate host is transformed by well-known techniques. In some embodiments, transformed cells are plated at a density to produce approximately 200-300 transformed colonies per petri dish. For selection of reverse transcriptase, colonies can then be screened for the expression of a reverse transcriptase or a thermostable reverse transcriptase using methods well-known to those skilled in the art. For example, in some embodiments, overnight cultures of individual transformant colonies are lysed, heated at 50° C. for 15 minutes and assayed for reverse transcriptase or thermostable reverse transcriptase activity and/or other desirable activities using a fluorescently-labeled stem loop template (e.g. FRET assay). See, for example, Nikiforov, T. T., Anal Biochem., 2011, 412(2): 229-36. In some embodiments, thermostable reverse transcriptase activity and/or other desirable activity are detected, the mutant is sequenced to determine which amino acids maintain reverse transcriptase activity. The gene or nucleic acid molecule encoding a reverse transcriptase of the present invention can be cloned using techniques known to those in the art.

Mutant Reverse Transcriptases

In accordance with the invention, a number of specified mutations can be made to the reverse transcriptases and, in a preferred aspect, multiple mutations can be made to result in an increased thermostability, thermoactivity, increased resistance to inhibitors, and/or to confer other desired properties on reverse transcriptases as described. Such mutations include point mutations, frame shift mutations, deletions and insertions. Preferably, one or more point mutations, resulting in one or more amino acid substitutions, are used to produce reverse transcriptases having enhanced or increased thermostability and/or thermoreactivity or increased resistance to inhibitors.

Mutations can be introduced into reverse transcriptases of the present invention using any methodology known to those of skill in the art. Mutations can be introduced randomly by, for example, conducting a PCR reaction in the presence of manganese as a divalent metal ion cofactor. Alternatively, oligonucleotide directed mutagenesis may be used to create the mutant polymerases which allows for all possible classes of base pair changes at any determined site along the encoding DNA molecule. In general, this technique involves annealing an oligonucleotide complementary (except for one or more mismatches) to a single stranded nucleotide sequence coding for the reverse transcriptase of interest. The mismatched oligonucleotide is then extended by DNA polymerase, generating a double-stranded DNA molecule which contains the desired change in sequence in one strand. The changes in sequence can, for example, result in the deletion, substitution, or insertion of an amino acid. The double-stranded polynucleotide can then be inserted into an appropriate expression vector, and a mutant polypeptide can thus be produced. The above-described oligonucleotide directed mutagenesis can, for example, be carried out via PCR.

In general, the invention provides, in part, reverse transcriptases with one or more (e.g., one, two, three, four, five, ten, twelve, fifteen, eighteen, twenty, etc.) mutations or modification at specified amino acid sites which render the reverse transcriptase more thermostable and/or thermoreactive compared to its un-mutated counterpart. The invention also provides reverse transcriptases with one or more specified mutations or modification which render the reverse transcriptase more efficient (e.g., having increased speed and/or processivity), more specific, more resistant to reverse transcriptase inhibitors than a corresponding un-mutated reverse transcriptase, and/or better able to generate cDNAs from difficult RNA templates.

In some embodiments, the mutations or modifications of the reverse transcriptases provided by the invention are made in a recognized region of the reverse transcriptase enzyme (e.g., pol or RNase H region) in such a way as to produce a mutated reverse transcriptase having increased or enhanced thermostability and/or thermoreactivity. Modifications or mutations may also be made in other regions in accordance with the invention (e.g., such as those regions know to play a role in enzyme Kd, thermostability, fidelity, substrate binding, etc.). Thus, the invention includes reverse transcriptases which exhibit increased thermostability (as well as other properties), as described elsewhere herein, and have one or more (e.g., one, two, three, four, five, ten, fifteen, twenty, etc.) specified mutations or modification or combination of mutations or modifications.

In certain embodiments of the invention, amino acid substitutions are made at one or more of the amino acid positions corresponding to the sequence for wild type M-MLV reverse transcriptase (SEQ ID NO:2) which are listed in Table 1 below (e.g., amino acid position 51, 67, 69, 196, 197, 200, 204, 289, 302, 306, 309, 313, 435, 454, 524, 562, 583, 594, 603, 653, and 671). In accordance with the invention, the wild type amino acids at these positions may be substituted with any other amino acid including Ala, Arg, Asn, Arg, Asp, Cys, Gln, Glu, Gly, His, Ile, Leu, Lys, Met, Phe, Pro, Ser, Thr, Trp, Tyr, and Val. Certain illustrative amino acids at these positions are those listed in Table 1 (e.g., L/P51, S/R/N/K67, K/E69, S/P196, T/A/S/G197, N/D200, H/R204, L/M289, K/R/E/G302, T/K306, F/Y/I/N309, F/L/C/W313, P/T330, L/V/R/G435, N/K454 D/G524, Q/E562, N/D583, N/D594, H/Q603, H/N/D653, and L/P671. Thus, specific examples of reverse transcriptases according to the invention which exhibit increased thermostability and/or thermoreactivity include M-MLV reverse transcriptase in which (1) the residue at position 51 is proline (P) or lysine (L); (2) residue at position 67 is the serine (S), arginine (R), lysine (K) or asparagine (N); (3) the residue at position 69 is glutamic acid (E) or lysine (K); (4) the residue at position 196 is proline (P) or serine (S); (5) the residue at position 197 is threonine (T), glycine (G), serine (S) or alanine (A); (6) the residue at position 200 is aspartic acid (D) or asparagine (N); (7) the residue at position 204 is histidine or asparagine (R); (8) the residue at position 289 is methionine (M) or leucine (L); (9) the residue at position 302 is glutamic acid residue (E), lysine (K), arginine (R), or glycine (G); (10) the residue at position 306 is threonine (T) or lysine (K); (11) the residue at position 309 is phenylalanine (F), tyrosine (Y), isoleucine (I) or asparagine (N); (12) the residue at position 313 is tryptophan (W), phenylalanine (F), leucine (L) or cysteine (C); (13) the residue at position 330 is tyrosine (Y) or proline (P); (14) the residue at position 435 is leucine (L), valine (V), arginine (R), or glycine (G); (15) the residue at position 454 is asparagine (N) or lysine (K); (16) the residue at position 524 is aspartic acid (D) or glycine (G); (17) the residue at position 562 is glutamic acid (E) or glutamine (Q); (18) the residue at position 583 is aspartic acid (D) or asparagine (N); (19) the residue at position 594 is histidine (H) or glutamine (Q); (20) the residue at position 603 is leucine (L) or tryptophan (W); (21) the residue at position 653 is aspartic acid (D), histidine (H) or asparagine (N); and (22) the residue at position 671 is leucine (L) or proline (P).

TABLE 1

Mutant Reverse Transcriptases

| | Amino Acid Position | | | | | | | | | | | | | | | | | | | | | |
|---|---|---|---|---|---|---|---|---|---|---|---|---|---|---|---|---|---|---|---|---|---|---|
| | 51 | 67 | 69 | 196 | 197 | 200 | 204 | 289 | 302 | 306 | 309 | 313 | 330 | 435 | 454 | 524 | 562 | 583 | 594 | 603 | 653 | 671 |
| Amino Acid Substitutions (any amino acid listed for a given position can be selected in combination with any listed amino acid at any other given position) | L P | S R N K | K E | S P | T A S G | N D | H R | L M | K R E G | T K | F Y I N | F L C W | P T | L V R G | N K | D G | Q E | N D | H Q | L W | H N D | L P |
| Wild Type M-MLV RT | P | S | E | P | T | D | H | M | E | T | F | W | T | L | N | D | E | D | H | L | D | L |
| Mutant M-MLV RTs | | | | | | | | | | | | | | | | | | | | | | |
| A7 | P | R | E | P | S | D | H | L | R | T | N | W | P | R | K | D | | | | | | |
| D3 | P | S | E | P | T | N | H | L | K | T | F | W | P | G | K | G | E | N | Q | L | H | P |
| D9 | L | R | K | P | A | D | R | M | K | T | N | F | P | G | K | G | E | N | Q | L | N | P |
| E7 | P | R | K | P | S | N | H | L | R | K | Y | F | T | R | K | G | E | D | H | W | D | L |
| P1A7 | P | R | K | P | A | N | H | L | K | T | Y | F | P | G | N | G | E | N | H | W | H | P |
| P1E2 | P | K | K | P | T | D | R | M | R | T | N | F | P | L | K | G | | | | | | |
| P2A5 | P | R | K | P | S | N | H | L | E | T | F | L/W | P | R | K | G | Q | N | H | L | H | L |
| P2B4 | P | K | K | P | S | N | R | L | E | K | I | F | P | R | K | G | E | D | H | W | H | P |
| P2B6 | P | S | K | P | S | D | H | L | G | K | N | F | P | R | K | D | E | N | Q | W | N | L |
| P2C3 | P | R | K | P | A | D | R | M | R | T | N | F | P | L | K | G | E | N | Q | W | D | P |
| P3A8 | P | S | K | S | T | D | R | L | R | T | N | W | P | G | K | G | E | N | H | W | D | P |
| P3H6 | P | R | K | P | T | N | H | L | K | T | Y | C | P | R | K | D | E | N | Q | ? | H | L |
| P4B4 | P | K | K | P | T | D | R | L | G | T | N | F | T | L | N | G | E | N | Q | L | N | P |
| P4F6 | P | K | E | P | A | D | H | M | K | T | N | F | P | G | K | D | | | | | | |
| C9 | P | R | K | P | T | D | H | L | E | K | I | L | T | L | K | D | E | D | H | ? | H | P |
| D8 | L | K | K | P | A | N | H | M | K | K | I | W | P | G | N | G | E | D | Q | W | D | P |
| E3 | L | K | K | P | T | N | R | L | G | K | I | L | P | G | N | D | E | N | H | W | H | P |
| F4 | L | K | E | P | T | N | H | M | E | K | N | F | T | R | K | G | Q | N | H | W | H | P |

TABLE 1-continued

Mutant Reverse Transcriptases

Amino Acid Position

| | 51 | 67 | 69 | 196 | 197 | 200 | 204 | 289 | 302 | 306 | 309 | 313 | 330 | 435 | 454 | 524 | 562 | 583 | 594 | 603 | 653 | 671 |
|---|---|---|---|---|---|---|---|---|---|---|---|---|---|---|---|---|---|---|---|---|---|---|
| Other Possible RTs | | | | | | | | | | | | | | | | | | | | | | |
| BABOON | D | S | E | P | T | D | H | A | E | T | F | W | E | I | N | D | E | D | H | L | D | P |
| FELINE | Q | P | E | P | T | D | H | L | E | T | Y | W | P | L | N | D | E | D | H | L | D | |
| KOALA | E | S | E | P | T | D | H | M | E | T | F | W | E | I | N | D | E | D | H | L | D | K |
| FOWL | Q | T | E | P | T | D | N | L | E | T | Y | W | G | T | N | D | E | D | H | L | D | S |
| HUMAN | E | P | E | P | T | G | A | C | K | A | F | W | W | K | N | D | E | D | H | L | D | L |
| OPOSSUM | P | P | A | P | T | S | A | L | E | T | Y | W | E | A | H | D | E | D | H | Y | D | L |
| BOAR | Q | S | E | P | T | D | H | V | E | T | F | W | E | I | N | D | E | D | H | L | D | M |

In some embodiments, mutations or modifications in reverse transcriptases which alter thermoreactivity and/or thermostability properties may be present in conjunction with alterations which either have little or no effect on activities normally associated with reverse transcriptases (e.g., RNase H activity, reverse transcriptase or polymerase activity, terminal deoxynucleotidyl transferase (TdTase) activity, etc.) or substantially alter one or more of these activities normally associated with reverse transcriptases.

In some embodiments, one or more mutations at a position equivalent or corresponding to positions S67, T197, and E302 of wild type M-MLV (SEQ ID NO:2) reverse transcriptase can be made to produce the desired result (e.g., increased thermostability, increased thermoreactivity, increased efficiency (speed and processivity), increased specificity, increased resistance to reverse transcriptase inhibitors, and increased ability to generate cDNA from difficult RNA templates.). Thus, in some embodiments, using amino acid positions of M-MLV reverse transcriptase as a frame of reference, reverse transcriptases of the invention include any reverse transcriptase (e.g., M-MLV reverse transcriptase, AMV reverse transcriptase, HIV reverse transcriptase, RSV reverse transcriptase, reverse transcriptases from viruses isolated from, for example, baboon, fowl pox, koala bear, and wild boar species) having alterations that correspond in position to one or more of the following alterations: (S67R, S67N, or S67K), (T197A, T197S, T197G), and (302K, E302R, or E302G), as well as compositions, kits, and reaction mixtures containing these mutated proteins, nucleic acid molecules which encode these proteins, and host cells which contain these nucleic acid molecules.

In other embodiments, six or more mutations at positions equivalent or corresponding to positions P51, E69, P196, D200, H204, M289, T306, F309, W313, T330, L435, N454, D524, E562, D583, H594, L603, D653, and L671 of wild type M-MLV (SEQ ID NO:2) reverse transcriptase may be made to produce the desired result (e.g., increased thermostability, increased thermoreactivity, increased efficiency (speed and processivity), increased specificity, increased resistance to reverse transcriptase inhibitors, and/or increased ability to generate cDNA from difficult RNA templates.). Thus, in specific embodiments, using amino acid positions of M-MLV reverse transcriptase as a frame of reference, reverse transcriptases of the invention include any reverse transcriptase (e.g., M-MLV reverse transcriptase, AMV reverse transcriptase, HIV reverse transcriptase, RSV reverse transcriptase, reverse transcriptases from viruses isolated from, for example, baboon, fowl pox, koala bear, and wild boar species) having six or more of the following alterations: P51L, E69K, P196S, D200N, H204R, M289L, T306K, (F309N, F309Y, or F309I), (W313F, W313L, or W313C), T330P, (L435G, L435V, or L435R), N454K, D524G, E562Q, D583N, H594Q, L603W, (D653N or D653H), and L671P, as well as compositions and reaction mixtures containing these mutated proteins, nucleic acid molecules which encode these proteins, and host cells which contain these nucleic acid molecules.

In other embodiments, one or more mutations at a position equivalent or corresponding to positions S67, T197, and E302 and, additionally, one or more mutation at a position equivalent or corresponding to position P51, E69, P196, D200, H204, M289, T306, F309, W313, T330, L435, N454, D524, E562, D583, H594, L603, D653, and L671 of wild type M-MLV (SEQ ID NO:2) reverse transcriptase may be made to produce the desired result (e.g., increased thermostability, increased thermoreactivity, increased efficiency (speed and processivity), increased specificity, increased resistance to reverse transcriptase inhibitors, and/or increased ability to generate cDNA from difficult RNA templates.). Thus, in specific embodiments, using amino acid positions of M-MLV reverse transcriptase as a frame of reference, proteins of the invention include reverse transcriptases (e.g., M-MLV reverse transcriptase, AMV reverse transcriptase, HIV reverse transcriptase, RSV reverse transcriptase, reverse transcriptases from viruses isolated from, for example, baboon, fowl pox, koala bear, and wild boar species) having one or more of the following alterations: (S67R, S67N, or S67K), (T197A, T197S, T197G), and (302K, E302R, or E302G) and, additionally, one or more of the following alterations: P51L, E69K, P196S, D200N, H204R, M289L, T306K, (F309N, F309Y, or F309I), (W313F, W313L, or W313C), T330P, (L435G, L435V, or L435R), N454K, D524G, E562Q, D583N, H594Q, L603W, (D653N or D653H), and L671P, as well as compositions and reaction mixtures containing these mutated proteins, nucleic acid molecules which encode these proteins, and host cells which contain these nucleic acid molecules.

In other embodiments, six or more mutations at a position equivalent or corresponding to positions P51, E69, P196, D200, H204, M289, T306, F309, W313, T330, L435, N454, D524, E562, D583, H594, L603, D653, and L671 and, additionally, one or more mutation at a position equivalent or corresponding to position S67, T197, and E302 of wild type M-MLV (SEQ ID NO:2) reverse transcriptase can be made to produce the desired result (e.g., increased thermostability, increased thermoreactivity, increased efficiency (speed and processivity), increased specificity, increased resistance to reverse transcriptase inhibitors, and/or increased ability to generate cDNA from difficult RNA templates.). Thus, in specific embodiments, using amino acid positions of M-MLV reverse transcriptase as a frame of reference, proteins of the invention include reverse transcriptases (e.g., M-MLV reverse transcriptase, AMV reverse transcriptase, HIV reverse transcriptase, RSV reverse transcriptase, reverse transcriptases from viruses isolated from, for example, baboon, fowl pox, koala bear, and wild boar species) having six or more of the following alterations: P51L, E69K, P196S, D200N, H204R, M289L, T306K, (F309N, F309Y, or F309I), (W313F, W313L, or W313C), T330P, (L435G, L435V, or L435R), N454K, D524G, E562Q, D583N, H594Q, L603W, (D653N or D653H), and L671P and, additionally, one or more of the following alterations: (S67R, S67N, or S67K), (T197A, T197S, or T197G), and (E302K, E302R, or E302G), as well as compositions and reaction mixtures containing these mutated proteins, nucleic acid molecules which encode these proteins, and host cells which contain these nucleic acid molecules.

In other embodiments, mutations at each position equivalent or corresponding to positions S67, T197, and E302 and, additionally, mutations at each position equivalent or corresponding to position P51, E69, H204, F309, W313, T330, L435, N454, D524, D583, H594, D653, and L671 of wild type M-MLV (SEQ ID NO:2) reverse transcriptase can be made to produce the desired result (e.g., increased thermostability, increased thermoreactivity, increased efficiency (speed and processivity), increased specificity, increased resistance to reverse transcriptase inhibitors, and/or increased ability to generate cDNA from difficult RNA templates.). Thus, in specific embodiments, using amino acid positions of M-MLV reverse transcriptase as a frame of reference, proteins of the invention include reverse transcriptases (e.g., M-MLV reverse transcriptase, AMV reverse transcriptase, HIV reverse transcriptase, RSV reverse transcriptase, reverse transcriptases from viruses isolated from, for example, baboon, fowl pox, koala bear, and wild boar species) having the following alterations: (S67R, S67N, or S67K), (T197A, T197S, or T197G), and (302K, E302R, or E302G) and, additionally, at P51L, E69K, H204R, (F309N, F309Y, or F309I), (W313F, W313L, or W313C), T330P, (L435G, L435V, or L435R), N454K, D524G, D583N, H594Q, (D653N or D653H), and L671P, as well as compositions and reaction mixtures containing these mutated proteins, nucleic acid molecules which encode these proteins, and host cells which contain these nucleic acid molecules. In some embodiments, reverse transcriptases of the invention have the following mutations: P51L, S67R, E69K, T197A, H204R, E302M, F309N, W313F, T330P, L435G, N454K, D524G, D583N, H594QD653N, and L671P, also referred to herein as "Mut D9" (SEQ ID NO:4).

In some embodiments, the invention provides mutant reverse transcriptases or polypeptides having the properties described herein and at least 70% amino acid sequence identity to SEQ ID NO:4. For example, in some embodiments, reverse transcriptases of the invention are at least 70%, 75%, 80%, 85%, 90%, 95%, 97%, 98%, 99% or 100% identical to SEQ ID NO:4. In some embodiments, the invention provides mutant reverse transcriptases or polypeptides that comprise SEQ ID NO:4. In some preferred embodiments, the properties of the mutant reverse transcriptases or polypeptides described herein comprise one or more of the following: (a) increased thermostability; (b) increased thermoreactivity; (c) increased resistance to reverse transcriptase inhibitors; (d) increased speed; (e) decreased primer-less reverse transcription; and (f) increased processivity.

The corresponding positions of M-MLV reverse transcriptase identified above can be readily identified for other reverse transcriptases by one with skill in the art. Thus, given the defined region and the assays described in the present application, one with skill in the art can make the specified modifications which would result in increased thermostability, increased thermoactivity, and/or other desired features of any reverse transcriptase of interest. Identified regions of interest for other known reverse transcriptases and residues to be mutated in accordance with the present invention can include those listed in FIGS. 1A through 1D.

The nucleotide sequence for wild type M-MLV reverse transcriptase (SEQ ID NO:1) is well-known to those skilled in the art. See, for example, Shinnick et al., 1981, Nature 293:543-548; Georgiadis et al., 1995, Structure 3:879-892), the disclosure of which is incorporated herein by reference in its entirety.

In some preferred embodiments, oligonucleotide directed mutagenesis is used to create the mutant reverse transcriptases which allows for all possible classes of base pair changes at any determined site along the encoding DNA molecule. Those skilled in the art are well aware of that even when the amino acid substituted once is replaced again with another amino acid having similar characteristics (that is, conservative amino acid substitution), similar physiological and biochemical properties are still observed. The effect of amino acid substitution on the various amino acid properties and protein structure and functions has been well-studied by those in the art.

In some embodiments of the present invention, the mutant reverse transcriptases described herein demonstrate higher thermostability and/or thermoreactivity than the corresponding wild type reverse transcriptase. In some embodiments, M-MLV mutant reverse transcriptases having the following mutations: P51L, S67R, E69K, T197A, H204R, E302K, F309N, W313F, T330P, L435G, N454K, D524G, D583N, H594Q, D653N, and L671P, demonstrate increased thermostability at 60° C. In particular, in some embodiments, mutant M-MLV reverse transcriptases as disclosed herein demonstrate increased reverse transcriptase activity at 60° C. compared to the wild type M-MLV reverse transcriptase as well as compared to other commercially available M-MLV derivative reverse transcriptases (e.g., Q-SS, SSII, and SSIII) at temperatures much lower than 60° C. (i.e., 37° C., 42° C., and 50° C., respectively). See, for example, FIG. 2.

In some embodiments of the present invention, the mutant reverse transcriptases described herein demonstrate increased reverse transcriptase activity compared to the corresponding wild type reverse transcriptase. In some preferred embodiments, the mutant reverse transcriptases exhibit increased reverse transcriptase activity at reaction temperatures above 37° C. For example, the mutant reverse transcriptases as described herein exhibit increased reverse transcriptase activity at reaction temperatures of 38° C., 40° C., 42° C., 45° C., 48° C., 50° C., 52° C., 55° C., 58° C., 60° C., 62° C., 65° C., 68° C., 70° C., 72° C., 75° C., 78° C., etc. See, for example, FIG. 4.

In some embodiments of the present invention, the mutant reverse transcriptases described herein demonstrate increased reverse transcriptase activity that is at least 10% more compared to the corresponding wild type reverse transcriptase. For example, the mutant reverse transcriptases as described herein exhibit at least 10%, 15%, 20%, 25%, 30%, 35%, 40%, 45%, 50%, 55%, 60%, 65%, 70%, 75%, 80%, 85%, 90%, 95%, 100%, etc. more reverse transcriptase activity compared to the corresponding wild type reverse transcriptase. In some embodiments, the mutant reverse transcriptases as described herein exhibit 110%, 115%, 120%, 125%, 150%, 200%, 250%, 300%, 400%, 500%, etc. the amount of the reverse transcriptase activity exhibited by the wild type reverse transcriptase. In some embodiments, the mutant reverse transcriptases as described herein are at least about 1.1×, 1.5×, 1.8×, 2×, 4×, 6×, 8×, 10×, 30×, 40×, 50×, etc. more thermoreactive than the corresponding wild type reverse transcriptase. In some embodiments, the mutant reverse transcriptases of the present invention exhibit increased activity compared to the corresponding wild type reverse transcriptase, even when the reaction or incubation temperature of the mutant reverse transcriptase is at a higher temperature compared to the reaction or incubation temperature of the wild type polymerase.

In some embodiments of the present invention, the mutant reverse transcriptases described herein demonstrate improved or increased properties compared to the corresponding wild type reverse transcriptase when both reverse transcriptases are at the same reaction temperature (e.g., 37° C., 40° C., 42° C., 50° C., 52° C., 55° C., 58° C., 60° C., 62° C., 65° C. 70° C., or 75° C.). In some other embodiments, the mutant reverse transcriptases described herein demonstrate improved or increased properties at an elevated reaction temperature (e.g., 52° C., 55° C., 58° C., 60° C., 62° C., 65° C., 70° C., 75° C.) compared to the same properties demonstrated by the corresponding wild type reverse transcriptase at a lower temperature (e.g., 37° C., 40° C., 42° C., 50° C.).

In another aspect, the mutant reverse transcriptases described herein exhibit improved or increased activity (e.g., thermostability or thermoreactivity) at lower pH compared to the activity demonstrated by the corresponding wild type reverse transcriptase under the same pH. See, for example, FIG. 3.

In some embodiments, the reverse transcriptases of the present invention exhibit increased activity at a wider range of pH, producing more cDNA and longer cDNA compared to a non-mutated or conventional RTs under similar or the same conditions. For example, the mutant reverse transcriptases described herein exhibit increased activity compared to wild type reverse transcriptase at a pH range from about from about pH 5.5 to about pH 9.0 (e.g., about pH 6.0, about pH 6.5, about pH 7.0, about pH 7.1, about pH 7.2, about pH 7.3, about pH 7.4, about pH 7.5, about pH 7.6, about pH 7.7, about pH 7.8, about pH 7.9, about pH 8.0, about pH 8.1, about pH 8.2, about pH 8.3, about pH 8.4, about pH 8.5, about pH 8.6, about pH 8.7, about pH 8.8, about pH 8.9, about pH 9.0, from about pH 6.0 to about pH 8.5, from about pH 6.5 to about pH 8.5, from about pH 7.0 to about pH 8.5, from about pH 7.5 to about pH 8.5, from about pH 6.0 to about pH 8.0, from about pH 6.0 to about pH 7.7, from about pH 6.0 to about pH 7.5, from about pH 6.0 to about pH 7.0, from about pH 7.2 to about pH 7.7, from about pH 7.3 to about pH 7.7, from about pH 7.4 to about pH 7.6, from about pH 7.0 to about pH 7.4, from about pH 7.6 to about pH 8.0, from about pH 7.6 to about pH 8.5, from about pH 7.7 to about pH 8.5, from about pH 7.9 to about pH 8.5, from about pH 8.0 to about pH 8.5, from about pH 8.2 to about pH 8.5, from about pH 8.3 to about pH 8.5, from about pH 8.4 to about pH 8.5, from about pH 8.4 to about pH 9.0, from about pH 8.5 to about pH 9.0, etc.). In some embodiments, the mutant reverse transcriptases of the present invention exhibit at least 10% (e.g., 10%, 15%, 20%, 25%, 30%, 40%, 50%, 75%, 100%, 200%, 300%, 500%, etc.) more activity compared to the wild type RT at the same pH. In other embodiments, the mutant reverse transcriptases of the present invention produce at least 10% (e.g., 10%, 15%, 20%, 25%, 30%, 40%, 50%, 75%, 100%, 200%, 300%, 500%, etc.) more cDNA product compared to the wild type RT at the same pH. In still other embodiments, the mutant reverse transcriptases of the present invention produce cDNA products that are at least 10% (e.g., 10%, 15%, 20%, 25%, 30%, 40%, 50%, 75%, 100%, 200%, 300%, 500%, etc.) longer than the cDNA products produced by the corresponding wild type RT at the same pH. In yet other embodiments, the mutant reverse transcriptases of the present invention produce cDNA products at a rate that is at least 10% (e.g., 10%, 15%, 20%, 25%, 30%, 40%, 50%, 75%, 100%, 200%, 300%, 500%, etc.) faster than that of the corresponding wild type RT at the same pH. For example, the mutant reverse transcriptases of the present invention produces at least 2× more (e.g., 2×, 3×, 4×, 5×, 10×, 20×, etc.) cDNA product than the corresponding wild type RT at the same pH.

In some embodiments of the present invention, the mutant reverse transcriptases described herein retain at least 20% reverse transcriptase activity after heating to a temperature between 55° C. to 75° C. For example, the mutant reverse transcriptases retain at least 20%, 25%, 30%, 35%, 40%, 45%, 50%, 55%, 60%, 65%, 70%, 75%, 80%, 90%, 95%, 99% or 100% reverse transcriptase activity after heating to a temperature between 55° C. to 75° C. In some embodiments, the mutant reverse transcriptases retain at least 20% reverse transcriptase activity after heating to a temperature between 55° C. to 75° C. for at least 5 minutes. For example, the mutant reverse transcriptases retain at least 20%, 25%, 30%, 35%, 40%, 45%, 50%, 55%, 60%, 65%, 70%, 75%, 80%, 90%, 95%, 99% or 100% reverse transcriptase activity after heating to a temperature between 55° C. to 75° C. for at least 5 minutes.

In some embodiments of the present invention, the mutant reverse transcriptases described herein retain at least 20% reverse transcriptase activity after heating to a temperature between 50° C. to 75° C. For example, the mutant reverse transcriptases retain at least 20% reverse transcriptase activity after heating to a temperature of 50° C., 55° C., 58° C., 60° C., 62° C., 64° C., 68° C., 70° C., 72° C., or 75° C. In some embodiments, the mutant reverse transcriptases retain at least 20% reverse transcriptase activity after heating to a temperature between 50° C. to 75° C. for at least 5 minutes. For example, the mutant reverse transcriptases retain at least 20% reverse transcriptase activity after heating to a temperature between a temperature of 50° C., 58° C., 60° C., 62° C., 64° C., 68° C., 70° C., 72° C., or 75° C. for at least 5 minutes.

In some embodiments of the present invention, the mutant reverse transcriptases described herein retain at least 20% reverse transcriptase activity after heating to a temperature between 50° C. to 75° C. for at least 1 minute. For example, the mutant reverse transcriptases retain at least 20% reverse transcriptase activity after heating to a temperature between 50° C. to 75° C. for at least 1 minute, 2 minutes, 5 minutes, 10 minutes, 15 minutes, 20 minutes, 30 minutes, 40 minutes, 50 minutes, 60 minutes, etc. In some embodiments, the mutant reverse transcriptases retain at least about 20%, about 25%, about 30%, about 35%, about 40%, about 45%, about 50%, about 55%, about 60%, about 65%, about 70%, about 75%, about 80%, about 90%, about 95%, about 99% or about 100% reverse transcriptase activity after heating to a temperature of about 50° C., about 55° C., about 58° C., about 60° C., about 62° C., about 64° C., about 68° C., about 70° C., about 72° C., or about 75° C. for at least about 1 minute, about 2 minutes, about 5 minutes, about 10 minutes, about 15 minutes, about 20 minutes, about 30 minutes, about 40 minutes, about 50 minutes, or about 60 minutes.

In some embodiments of the present invention, the mutant reverse transcriptases described herein are able to produce a cDNA that is at least 0.2 kb in length. For example, the mutant reverse transcriptases are able to produce a cDNA that is 0.2 kb, 0.5 kb, 1 kb, 1.5 kb, 2 kb, 3 kb, 4 kb, 5 kb, 6 kb, 7 kb, 7.5 kb, 8 kb, 8.5 kb, 9 kb, 9.5 kb, 10 kb, 15 kb, or 20 kb, etc. in length. In some embodiments, the mutant reverse transcriptases described herein are able to produce a cDNA that is between about 0.2 kb to 10 kb in length. In some embodiments, the mutant reverse transcriptases described herein are able to produce a cDNA that is between about 0.2 kb to 10 kb in length within 1 to 60 minutes at a temperature between 25° C. to 75° C. In some embodiments, the mutant reverse transcriptases are able to produce a cDNA that is between about 0.2 kb to 10 kb in length within 1 minute, 5 minutes, 10 minutes, 15 minutes, 20 minutes, 30 minutes, 40 minutes, 50 minutes or 60 minutes at a temperature of at least 37° C. (e.g., 37° C., 40° C., 45° C., 50° C., 55° C., 60° C., 70° C. or 75° C.).

In some preferred embodiments, the mutant or mutated reverse transcriptases of the present invention demonstrate higher thermostability than the corresponding wild type reverse transcriptase. In particular, mutant reverse transcriptases as described herein, exhibit increased thermostability and/or increased thermoreactivity. Among some of the possible mutant reverse transcriptases provided herein, an exemplary mutant "D9" (SEQ ID NO:4) (see FIG. 11) demonstrates increased thermostability at least 50° C. In some embodiments, at 60° C. this exemplary mutant reverse transcriptase produces cDNA more efficiently than wild type M-MLV reverse transcriptase at a temperature of 37° C. (see, for example, FIG. 2).

In another aspect, the mutant reverse transcriptases as described herein are resistant to enzyme inhibitors found in biological samples, including, for example, blood, sweat, tears, soil, feces, saliva, urine, and bile. Such inhibitors can include, but are not limited to, humic acid, heparin, ethanol, bile salts, fulvic acid, polysaccarides, metal ions, sodium dodecyl sulfate (SDS), EDTA, guanidinium salts, formamide, sodium pyrophosphate, and spermidine. An inhibitor-resistant reverse transcripatase, as used herein, can generally refer to a reverse transcriptase that exhibits at least 10% reverse transcriptase activity in the presence of an inhibitor(s) in the reaction mixture. For example, the mutant reverse transcriptases described herein exhibit up to about 90% (e.g., 90%, 85%, 80%, 75%, 70%, 65%, 60%, 55%, 50%, 45%, 40%, 35%, 30%, 25%, 20%, 15%, 10%, 5%, etc.) reverse transcriptase activity in the presence of an inhibitor compared to reactions comprising no inhibitor. The amount of inhibitor in any given reaction mixture can depend upon the type of inhibitory substance that exists within the biological sample from which the nucleic acid being assayed is extracted. Generally, mutant reverse transcriptases described herein (even when at elevated temperatures) can tolerate at least 2× (e.g., 2×, 3×, 5×, 10×, 50×, 100×) greater concentration of these inhibitory substances, as compared to the corresponding wild type reverse transcriptase. Assays to determine the level of inhibitory substances in a sample are known in the art. Inhibitor-resistance can be readily determined by assays described herein.

Expression of Reverse Transcriptases

To optimize expression of reverse transcriptases of the present invention, inducible or constitutive promoters are well known and may be used to express high levels of a reverse transcriptase structural gene in a recombinant host. Similarly, high copy number vectors, well known in the art, may be used to achieve high levels of expression. Vectors having an inducible high copy number may also be useful to enhance expression of the reverse transcriptases of the invention in a recombinant host.

To express the desired structural gene in a prokaryotic cell (such as *E. coli, B. subtilis, Pseudomonas*, etc.), it is preferable to operably link the desired structural gene to a functional prokaryotic promoter. However, the natural promoter of the reverse transcriptase gene may function in prokaryotic hosts allowing expression of the reverse transcriptase gene. Thus, the natural promoter or other promoters may be used to express the reverse transcriptase gene. Such other promoters that may be used to enhance expression include constitutive or regulatable (i.e., inducible or derepressible) promoters. Examples of constitutive promoters include the int promoter of bacteriophage λ, and the bla promoter of the β-lactamase gene of pBR322. Examples of inducible prokaryotic promoters include the major right and left promoters of bacteriophage λ (PR and PL), trp, recA, lacZ, lad, tet, gal, trc, ara BAD (Guzman, et al., 1995, J. Bacteriol. 177(14):4121-4130) and tac promoters of *E. coli*. The *B. subtilis* promoters include α-amylase (Ulmanen et al., J. Bacteriol 162:176-182 (1985)) and *Bacillus* bacteriophage promoters (Gryczan, T., In: The Molecular Biology Of Bacilli, Academic Press, New York (1982)). Streptomyces promoters are described by Ward et al., Mol. Gen. Genet. 203:468478 (1986)). Prokaryotic promoters are also reviewed by Glick, J. Ind. Microbiol. 1:277-282 (1987); Cenatiempto, Y., Biochimie 68:505-516 (1986); and Gottesman, Ann. Rev. Genet. 18:415-442 (1984). Expression in a prokaryotic cell also requires the presence of a ribosomal binding site upstream of the gene-encoding sequence. Such ribosomal binding sites are disclosed, for example, by Gold et al., Ann. Rev. Microbiol. 35:365404 (1981).

To enhance the expression of reverse transcriptases of the invention in a eukaryotic cell, well known eukaryotic promoters and hosts may be used. Enhanced expression of the reverse transcriptases may be accomplished in a prokaryotic host. One example of a prokaryotic host suitable for use with the present invention is *Escherichia coli*.

Isolation and Purification of Reverse Transcriptases

The enzyme(s) of the present invention is preferably produced by growth in culture of the recombinant host containing and expressing the desired reverse transcriptase gene. However, the reverse transcriptase of the present invention may be isolated from any strain, organism, or tissue which produces the reverse transcriptase of the present invention, Fragments of the reverse transcriptase are also included in the present invention. Such fragments include proteolytic fragments and fragments having reverse transcriptase activity, Such fragments may also be produced by cloning and expressing portions of the reverse transcriptase gene of interest, creating frame shift mutations and/or by adding one or more stop codons in the gene of interest for expression of a truncated protein or polypeptide. Preferably, polypeptides of the invention may be purified and/or isolated from a cell or organism expressing them, which may be a wild type cell or organism or a recombinant cell or organism. In some embodiments, such polypeptides may be substantially isolated from the cell or organism in which they are expressed.

Any nutrient that can be assimilated by a host containing the cloned reverse transcriptase gene may be added to the culture medium. Optimal culture conditions should be selected case by case according to the strain used and the composition of the culture medium. Antibiotics may also be added to the growth media to insure maintenance of vector DNA containing the desired gene to be expressed. Media formulations have been described in DSM or ATCC Catalogs and Sambrook et al., In: *Molecular cloning, a Laboratory Manual* (2nd ed.), Cold Spring Harbor Laboratory Press, Cold Spring Harbor, N.Y. (1989).

Recombinant host cells producing the reverse transcriptases of this invention can be separated from liquid culture, for example, by centrifugation. In general, the collected microbial cells are dispersed in a suitable buffer, and then broken open by ultrasonic treatment or by other well-known procedures to allow extraction of the enzymes by the buffer solution. After removal of cell debris by ultracentrifugation or centrifugation, the reverse transcriptases can be purified by standard protein purification techniques such as extraction, precipitation, chromatography, affinity chromatography, electrophoresis or the like. Assays to detect the presence of the reverse transcriptase during purification are well known in the art and can be used during conventional biochemical purification methods to determine the presence of these enzymes.

In some embodiments, reverse transcriptases of the present invention may be mutated to contain an affinity tag in order to facilitate the purification of the reverse transcriptase. Suitable affinity tags are well known to those skilled in the art and include, but are not limited to, repeated sequences of amino acids such as six histidines (SEQ ID NO: 6) epitopes such as the hemagglutinin epitope and the myc epitope, and other amino acid sequences that permit the simplified purification of the reverse transcriptase.

The invention further provides fusion proteins comprising (1) a protein, or fragment thereof, having one or more activity associated with a reverse transcriptase and (2) a tag (e.g., an affinity tag). In particular embodiments, the invention includes a reverse transcriptase (e.g., a thermostable reverse transcriptase) described herein having one or more (e.g., one, two, three, four, five, six, seven, eight, etc.) tags. These tags may be located, for example, (1) at the N-terminus, (2) at the C-terminus, or (3) at both the N-terminus and C-terminus of the protein, or a fragment thereof having one or more activities associated with a reverse transcriptase. A tag may also be located internally (e.g., between regions of amino acid sequence derived from a reverse transcriptase and/or attached to an amino acid side chain). For example, Ferguson et al., *Protein Sci.* 7:1636-1638 (1998), describe a siderophore receptor, FhuA, from *Escherichia coli* into which an affinity tag (i.e., a hexahistidine sequence (SEQ ID NO: 6) was inserted. This tag was shown to function in purification protocols employing metal chelate affinity chromatography. Additional fusion proteins with internal tags are described in U.S. Pat. No. 6,143,524, the entire disclosure of which is incorporated herein by reference.

Tags used to prepare compositions of the invention may vary in length but will typically be from about 5 to about 500, from about 5 to about 100, from about 10 to about 100, from about 15 to about 100, from about 20 to about 100, from about 25 to about 100, from about 30 to about 100 from about 35 to about 100, from about 40 to about 100, from about 45 to about 100, from about 50 to about 100, from about 55 to about 100, from about 60 to about 100, from about 65 to about 100, from about 70 to about 100, from about 75 to about 100, from about 80 to about 100, from about 85 to about 100, from about 90 to about 100, from about 95 to about 100, from about 5 to about 80, from about 10 to about 80, from about 20 to about 80, from about 30 to about 80, from about 40 to about 80, from about 50 to about 80, from about 60 to about 80, from about 70 to about 80, from about 5 to about 60, from about 10 to about 60, from about 20 to about 60, from about 30 to about 60, from about 40 to about 60, from about 50 to about 60, from about 5 to about 40, from about 10 to about 40, from about 20 to about 40, from about 30 to about 40, from about 5 to about 30, from about 10 to about 30, from about 20 to about 30, from about 5 to about 25, from about 10 to about 25, or from about 15 to about 25 amino acid residues in length.

Tags used to prepare compositions of the invention include those which contribute to the thermostability of the fusion protein. Thus, these tags may be at least partly responsible, for example, for a particular protein (e.g., a protein having one or more activities of a reverse transcriptase activity) having increased thermostability. Examples of tags that enhance the thermostability of a reverse transcriptase (i.e., M-MLV reverse transcriptase) include, but are not limited to, tags having the following amino acid sequences: MGGSHHHHHHGMASMASMTG-GQQMGRDLYDDDDKH (SEQ ID NO: 7) and MASGTG-GQQMGRDLYDDDDKH (SEQ ID NO: 8). Fragments of these tags may also be used in accordance with the invention (preferably those having 3 or more, 5 or more, 10 or more, or 15 or more amino acids) Thus, the invention includes, in part, reverse transcriptases, or fragments thereof that comprise tags and demonstrate enhanced thermostability. Using well known methods, one of skill in the art can attach one or more of above-mentioned tags to one or more RT enzymes, or fragments thereof having reverse transcriptase activity, to produce a thermostable reverse transcriptase enzyme or fragment thereof.

Tags used in the practice of the invention may serve any number of purposes and a number of tags may be added to impart one or more different functions to the reverse transcriptase of the invention. For example, tags may (1) contribute to protein-protein interactions both internally within a protein and with other protein molecules, (2) make the protein amenable to particular purification methods, (3) enable one to identify whether the protein is present in a composition; or (4) give the protein other functional characteristics.

Examples of tags which may be used in the practice of the invention include metal binding domains (e.g., a polyhistidine segments such as a three, four, five, six, or seven histidine region (SEQ ID NO: 9)), immunoglobulin binding domains (e.g., (1) Protein A; (2) Protein G; (3) T cell, B cell, and/or Fc receptors; and/or (4) complement protein antibody-binding domain); sugar binding domains (e.g., a maltose binding domain, chitin-binding domain); and detectable domains (e.g., at least a portion of beta-galactosidase). Fusion proteins may contain one or more tags such as those described above. Typically, fusion proteins that contain more than one tag will contain these tags at one terminus or both termini (i.e., the N-terminus and the C-terminus) of the reverse transcriptase, although one or more tags may be located internally instead of or in addition to those present at termini. Further, more than one tag may be present at one terminus, internally and/or at both termini of the reverse transcriptase. For example, three consecutive tags could be linked end-to-end at the N-terminus of the reverse transcriptase. The invention further include compositions and reaction mixture which contain the above fusion proteins, as well as methods for preparing these fusion proteins, nucleic acid molecules (e.g., vectors) which encode these fusion proteins and recombinant host cells which contain these nucleic acid molecules. The invention also includes methods for using these fusion proteins as described elsewhere herein (e.g., methods for reverse transcribing nucleic acid molecules).

Tags which enable one to identify whether the fusion protein is present in a composition include, for example, tags which can be used to identify the protein in an electrophoretic gel. A number of such tags are known in the art and include epitopes and antibody binding domains which can be used for Western blots.

The amino acid composition of the tags for use in the present invention may vary. In some embodiments, a tag may contain from about 1% to about 5% amino acids that have a positive charge at physiological pH, e.g., lysine, arginine, and histidine, or from about 5% to about 10% amino acids that have a positive charge at physiological pH, or from about 10% to about 20% amino acids that have a positive charge at physiological pH, or from about 10% to about 30% amino acids that have a positive charge at physiological pH, or from about 10% to about 50% amino acids that have a positive charge at physiological pH, or from about 10% to about 75% amino acids that have a positive charge at physiological pH. In some embodiments, a tag may contain from about 1% to about 5% amino acids that have a negative charge at physiological pH, e.g., aspartic acid and glutamic acid, or from about 5% to about 10% amino acids that have a negative charge at physiological pH, or from about 10% to about 20% amino acids that have a negative charge at physiological pH, or from about 10% to about 30% amino acids that have a negative charge at physiological pH, or from about 10% to about 50% amino acids that have a negative charge at physiological pH, or from about 10% to about 75% amino acids that have a negative charge at physiological pH. In some embodiments, a tag may comprise a sequence of amino acids that contains two or more contiguous charged amino acids that may be the same or different and may be of the same or different charge. For example, a tag may contain a series e.g., two, three, four, five, six, ten etc.) of positively charged amino acids that may be the same or different. A tag may contain a series (e.g., two, three, four, five, six, ten etc.) of negatively charged amino acids that may be the same or different. In some embodiments, a tag may contain a series (e.g., two, three, four, five, six, ten etc.) of alternating positively charged and negatively charged amino acids that may be the same or different (e.g., positive, negative, positive, negative, etc.). Any of the above-described series of amino acids (e.g., positively charged, negatively charged or alternating charge) may comprise one or more neutral polar or non-polar amino acids (e.g., two, three, four, five, six, ten etc.) spaced between the charged amino acids. Such neutral amino acids may be evenly distributed throughout the series of charged amino acids (e.g., charged, neutral, charged, neutral) or may be unevenly distributed throughout the series (e.g., charged, a plurality of neutral, charged, neutral, a plurality of charged, etc.). In some embodiments, tags to be attached to the polypeptides of the invention may have an overall charge at physiological pH (e.g., positive charge or negative charge). The size of the overall charge may vary, for example, the tag may contain a net plus one, two, three, four, five, etc. or may possess a net negative one, two, three, four, five, etc. The present invention also provides reverse transcriptases (e.g., thermostable reverse transcriptases) comprising one or more of the above-described tag sequences, vectors encoding such reverse transcriptases, host cells reaction mixture, compositions and reaction mixtures comprising such reverse transcriptases, as well as kits comprising containers containing such reverse transcriptases.

In some embodiments, it may be desirable to remove all or a portion of a tag sequence from a fusion protein comprising a tag sequence and a sequence having reverse transcriptase (RT) activity. In embodiments of this type, one or more amino acids forming a cleavage site, e.g., for a protease enzyme, may be incorporated into the primary sequence of the fusion protein. The cleavage site may be located such that cleavage at the site may remove all or a portion of the tag sequence from the fusion protein. In some embodiments, the cleavage site may be located between the tag sequence and the sequence having RT activity such that all of the tag sequence is removed by cleavage with a protease enzyme that recognizes the cleavage site. Examples of suitable cleavage sites include, but are not limited to, the Factor Xa cleavage site having the sequence Ile-Glu-Gly-Arg (SEQ ID NO: 10), which is recognized and cleaved by blood coagulation factor Xa, and the thrombin cleavage site having the sequence Leu-Val-Pro-Arg (SEQ ID NO: 11), which is recognized and cleaved by thrombin. Other suitable cleavage sites are known to those skilled in the art and may be used in conjunction with the present invention.

In some embodiments, the reverse transcriptases of the invention have specific activities (e.g., RNA-directed DNA polymerase activity and/or RNase H activity) greater than about 5 units/mg, preferably greater than about 50 units/mg, more preferably greater than about 100 units/mg, 250 units/mg, 500 units/mg, 1000 units/mg, 5000 units/mg or 10,000 units/mg, and most preferably greater than about 15,000 units/mg, greater than about 16,000 units/mg, greater than about 17,000 units/mg, greater than about 18,000 units/mg, greater than about 19,000 units mg and greater than about 20,000 units/mg. In some embodiments, the reverse transcriptases of the present invention may have specific activities greater than about 50,000 units mg, greater than about 100,000 units/mg, greater than about 150,000 units/mg, greater than about 200,000 units/mg, greater than about 250,000 units/mg and greater than about 300,000 units/mg. Preferred ranges of specific activities for the reverse transcriptases of the invention include a specific activity from about 5 units/mg to about 750,000 units/mg a specific activity from about 5 units/mg to about 500,000 units/mg, from about 5 units/mg to about 300,000 units/mg, a specific activity of from about 50 units/mg to about 750,000 units/mg, a specific activity from about 100 units/mg to about 750,000 units/mg, a specific activity from about 250 units/mg to about 750,000 units/mg, a specific activity from about 500 units/mg to about 750,000 units/mg, a specific activity from about 1000 units/mg to about 750,000 units/mg, a specific activity from about 5000 units/mg to about 750,000 units/mg, a specific activity from about 10,000 units/mg to about 750,000 units/mg, a specific activity from about 25,000 units/mg to about 750,000 units/mg, a specific activity from about 100 units/mg to about 500 units/mg, a specific activity from about 100 units/mg to about 400 units/mg and a specific activity from about 200 units/mg to about 500 units/mg, Other preferred ranges of specific activities include a specific activity of from about 200,000 units/mg to about 350,000 units/mg, a specific activity from about 225,000 units/mg to about 300,000 units/mg, a specific activity from about 250,000 units/mg to about 300,000 units/mg a specific activity of from about 200,000 units/mg to about 750,000 ti n its/mg, a specific activity of from about 200,000 units/mg to about 500,000 units/mg, a specific activity of from about 200,000 units/mg to about 400,000 units/mg a specific activity of from about 250,000 units/mg to about 750,000 units/mg, a specific activity of from about 250,000 units/mg to about 500,000 units/mg, and a specific activity of from about 250,000 units/mg to about 400,000 units/mg. Preferably, the lower end of the specific activity range may vary from 50, 100, 200, 300, 400, 500, 700, 900, 1,000, 5,000, 10,000, 20,000, 30,000, 35,000, 40,000, 45,000, 50,000, 55,000, 60,000, 65,000, 70,000, 75,000, and 80,000 units/mg, while the upper end of the range may vary from 750,000, 650,000, 600,000, 550,000, 500,000, 450,000, 400,000, 350,000, 300,000, 250,000, 200,000, 150,000, 140,000, 130,000, 120,000, 110,000, 100,000, and 90,000 units/mg. Specific activity may be determined using enzyme assays and protein assays well known in the art. DNA polymerase assays and RNase H assays are described, for example, in U.S. Pat. No. 5,244,797 and WO 98/47912, the disclosures of which are fully incorporated herein by reference. In some embodiments of the present invention, the specific activity of the thermostable reverse transcriptase prepared in accordance with the present invention may be higher than the specific activity of a non-thermostable (e.g., wild type) reverse transcriptase. In some embodiments, the specific activity of the thermostable reverse transcriptase may be 5%, 10,%, 15%, 20%, 25%, 30%, 40%, 50%, 60%, 70%, 80%, 90%, 100% or more higher than the specific activity of a corresponding non-thermostable reverse transcriptase. In some preferred embodiments, the specific activity of the thermostable reverse transcriptase according to the present invention may be 30% or more than the specific activity of a corresponding non-thermostable reverse transcriptase. In accordance with the invention, specific activity is a measurement of the enzymatic activity (in units) of the protein or enzyme relative to the total amount of protein or enzyme used in a reaction. The measurement of a specific activity may be determined by standard techniques well-known to one of ordinary skill in the art.

Compositions and Reaction Mixtures Comprising Reverse Transcriptases

The present teachings provide compositions comprising a variety of components in various combinations. In some embodiments of the present invention, the compositions are formulated by admixing one or more reverse transcriptases a in a buffered salt solution. One or more DNA polymerases and/or one or more nucleotides, and/or one or more primers may optionally be added to make the compositions of the invention. These compositions can be used in the present methods to produce, analyze, quantitate and otherwise manipulate nucleic acid molecules (e.g., using reverse transcription or one-step (coupled) RT-PCR procedures).

In some embodiments, the enzymes are provided at working concentrations (e.g., 1×) in stable buffered salt solutions. The terms "stable" and "stability" as used herein generally mean the retention by a composition, such as an enzyme composition, of at least 70%, preferably at least 80%, and most preferably at least 90%, of the original enzymatic activity (in units) after the enzyme or composition containing the enzyme has been stored for about one week at a temperature of about 4° C., about two to six months at a temperature of about −20° C., and about six months or longer at a temperature of about −80° C. As used herein, the term "working concentration" means the concentration of an enzyme that is at or near the optimal concentration used in a solution to perform a particular function such as reverse transcription of nucleic acids).

Such compositions can also be formulated as concentrated stock solutions (e.g., 2×, 3×, 4×, 5×, 6×, 10×, etc.). In some embodiments, having the composition as a concentrated (e.g., 5×) stock solution allows a greater amount of nucleic acid sample to be added (such as, for example, when the compositions are used for nucleic acid synthesis).

The water used in forming the compositions of the present invention Is preferably distilled, deionized and sterile filtered (through a 0.1-0.2 micrometer filter), and is free of contamination by DNase and RNase enzymes. Such water is available commercially, for example from Life Technologies (Carlsbad, Calif.) or may be made as needed according to methods well known to those skilled in the art.

In addition to the enzyme components, the present compositions can comprise one or more buffers and cofactors necessary for synthesis of a nucleic acid molecule such as a cDNA molecule. In some embodiments, buffers for use in forming the present compositions are the acetate, sulfate, hydrochloride, phosphate or free acid forms of Tris-(hydroxymethyl)aminomethane (TRIS®) or 4-(2-hydroxyethyl)-1-piperazineethanesulfonic acid (HEPES), although alternative buffers of the same approximate ionic strength and pKa as TRIS® or HEPES may be used with equivalent results. For example, possible buffers for use with the described enzymes can include, but are not limited to 3-{[tris(hydroxymethyl)methyl]amino} propanesulfonic acid (TAPS), N,N-bis(2-hydroxyethyl)glycine (Bicine), (hydroxymethyl)methylamine (Tris), N-tris(hydroxymethyl) methylglycine (Tricine), 3-[N-Tris(hydroxymethyl)methylamino]-2-hydroxypropanesulfonic Acid (TAPSO), 4-2-hydroxyethyl-1-piperazineethanesulfonic acid (HEPES), 2-{[tris(hydroxymethyl)methyl]amino} ethanesulfonic acid (TES), 3-(N-morpholino)propanesulfonic acid (MOPS), piperazine-N,N-bis(2-ethanesulfonic acid) (PIPES), and dimethylarsinic acid (cacodylate).

In addition to buffer salts, cofactor salts such as those of potassium (preferably potassium chloride or potassium acetate) and magnesium (preferably magnesium chloride or magnesium acetate are contemplated for use in the compositions of the invention.

Addition of one or more carbohydrates and/or sugars to the compositions and/or synthesis reaction mixtures may also be advantageous, to support enhanced stability of the compositions upon storage and/or reaction mixtures during synthesis. In some embodiments, carbohydrates or sugars for inclusion in the compositions and/or synthesis reaction mixtures of the invention include, but are not limited to, sucrose, trehalose, glycerol, and the like. In some embodiments, trehalose is provided at concentrations ranging from 0.01M to 5M (e.g., 0.01 M, 0.05 M, 0.1 M, 0.5 M, 0.75 M, 1.0 M, 2.0 M, 3.0 M, 4.0 M or 5.0 M). In some embodiments, glycerol is provided at concentrations ranging from 5% to 60%. (e.g., 5%, 10%, 15%, 25%, 30%, 40%, 50%, 60%). Furthermore, such carbohydrates and/or sugars may be added to the storage buffers for the enzymes used in the production of the enzyme compositions and kits of the invention and may be provided in compositions that are either in liquid or dry form (e.g., lyophilized). Such carbohydrates and/or sugars are commercially available from a number of sources, including Sigma (St. Louis, Mo.).

Likewise, addition of one or more surfactants and/or detergents to the compositions and/or synthesis reaction mixtures may also be advantageous, to support enhanced stability of the compositions and/or reaction mixtures upon storage. Preferred such detergents for inclusion in the compositions and/or synthesis reaction mixtures of the invention include, but are not limited to Tween 20, Nonidet P 40 (NP-40), Brij58, CHAPS, Big CHAPS, CHAPS, and the like. Other surfactants or detergents, such as those described in pending U.S. application Ser. No. 13/492,576 and 61/895,876 (the disclosures of which are incorporated herein by reference in their entirety) may also be included in the compositions and/or synthesis reaction mixtures of the invention. Furthermore, such detergents may be added to the storage buffers for the enzymes used in the production of the enzyme compositions and kits of the invention. Examples of such detergents are commercially available from a number of sources, including Sigma (St. Louis, Mo.).

It is often preferable to first dissolve the buffer salts, cofactor salts, carbohydrates or sugars, or detergents at working concentrations in water and to adjust the pH of the solution prior to addition of the enzymes. In this way, the pH-sensitive enzymes will be less subject to acid- or alkaline-mediated inactivation during formulation of the present compositions. Thus, in some embodiments, buffered salt solutions are formulated by combining a buffer salt such as a salt of Tris(hydroxymethyl)aminomethane (TRIS®) or the hydrochloride salt thereof, with a sufficient quantity of water. In some embodiments, this combination yields a solution having a TRIS® concentration of 5-150 millimolar, preferably 10-60 millimolar, and most preferably about 20-60 millimolar. To this solution, a salt of magnesium (preferably either the chloride or acetate salt (hereof) or other divalent cation, may be added to provide a working concentration thereof of 1-10 millimolar, preferably 1.5-8.0 millimolar, and most preferably about 3-7.5 millimolar. A salt of potassium (preferably a chloride or acetate salt of potassium), or other monovalent cation (e.g. Na), may also be added to the solution, at a working concentration of 10-100 millimolar and most preferably about 75 millimolar. A reducing agent, such as dithiothreitol, may be added to the solution, preferably at a final concentration of about 1-100 mM, more preferably a concentration of about 5-50 mM or about 7.5-20 mM, and most preferably at a concentration of about 10 mM. Preferred concentrations of carbohydrates and/or sugars for inclusion in the compositions of the invention range from about 5% (w/v) to about 30% (w/v), from about 7.5% (w/v) to about 25% (w/v), from about 10% (w/v) to about 25% (w/v), from about 10% (w/v) to about 20% (w/v), and preferably from about 10% (w/v) to about 15% (w/v). Preferred concentrations of surfactants and/or detergents for inclusion in the compositions of the invention range from about 0.001% (w/v) to about 5% WO, from about 0.002% WO to about 2% (w/v) from about 0.004% (w/v) to about 1% WO, from about 0.01% (w/v) to about 0.5% (w/v) and preferably from about 0.05% (w/v) to about 0.1% (w/v). A small amount of a salt of ethylenediaminetetraacetate (EDTA), such as disodium EDTA, may also be added (preferably about 0.1 millimolar). In some embodiments, after addition of all buffers and salts, this buffered salt solution is mixed well until all salts are dissolved, and the pH is adjusted using methods known in the art. In some embodiments, the final buffer pH ranges from about 6.0 to about 9.5, from about 6.9 to about 8.7, or from about 7.3 to about 8.3.

To these buffered salt solutions, the enzymes reverse transcriptases are added to produce the compositions of the present invention. In some embodiments, reverse transcriptases are added at a working concentration in the solution of from about 1,000 to about 50,000 units per milliliter, from about 2,000 to about 30,000 units per milliliter, from about 2,500 to about 25,000 units per milliliter, from about 3,000 to about 22,500 units per milliliter, from about 4,000 to about 20,000 units per milliliter, or from about 5,000 to about 20,000 units per milliliter. In some embodiments, a reverse transcriptases of the invention (e.g., an M-MLV reverse transcriptase) may be added at a working concentration described above in a first strand reaction mixture (e.g., a reaction to reverse transcribe an mRNA molecule) and/or in a reverse transcription coupled with a polymerase chain reaction. A suitable concentration of a reverse transcriptase of the invention for these reactions may be from about 5,000 units/ml to about 50,000 units/ml, from about 5,000 units/ml about 40,000 units/ml, from about 5,000 units/ml about 30,000 units/ml, or from about 5,000 units/ml to about 20,000 units/ml of reverse transcriptase. A reaction may be conducted in a volume of 20 µl to 50 µl and such a reaction may contain 50 units, 100, units, 200 units, 300 units, 400 units or more of a reverse transcriptase of the invention. Those skilled in the art will appreciate that adding additional reverse transcriptase may allow increased synthesis of the first strand (e.g., the DNA strand complementary to the mRNA strand) at the expense of increased enzyme usage. The skilled artisan can determine without undue experimentation the amount of a reverse transcriptase of the invention to add to a reaction in order to produce a desired amount of product at an acceptable expense.

In some embodiments, mutant reverse transcriptases described herein are provided at a working concentration in solution from about 100 to about 5000 units per milliliter, from about 125 to about 4000 units per milliliter, from about 150 to about 2000 units per milliliter, from about 200 to about 2500 units per milliliter, from about 225 to about 2000 units per milliliter, and most preferably at a working concentration of from about 250 to about 1000 units per milliliter. The enzymes may be added to the solution in any order, or may be added simultaneously.

The compositions of the invention may further comprise one or more nucleotides, which are preferably deoxynucleoside triphosphates (dNTPs) or dideoxynucleoside triphosphates (ddNTPs). The dNTP components of the present compositions serve as the "building blocks" for newly synthesized nucleic acids, being incorporated therein by the action of the polymerases, and the ddNTPs may be used in sequencing methods according to the invention. Examples of nucleotides suitable for use in the present compositions include, but are not limited to, dUTP, dATP, dTTP, dCTP, dGTP, dITP, 7-deaza-dGTP, α-thio-dATP, α-thio-dTTP, α-thio-dGTP, α-thio-dCTP, ddUTP, ddATP, ddTTP, ddCTP, ddGTP, ddITP, 7-deaza-ddGTP, α-thio-ddATP α-thio-ddTTP, α-thio-ddGTP, α-thio-ddCTP or derivatives thereof, all of which are available commercially from sources including Invitrogen Corporation (Carlsbad, Calif.), New England BioLabs (Beverly, Mass.) and Sigma Chemical Company (Saint Louis, Miss.). The nucleotides may be unlabeled, or they may be detectably labeled by coupling them by methods known in the art with radioisotopes (e.g., $^{3}$H, $^{14}$C, $^{32}$P or $^{35}$S), vitamins/e.g., biotin), fluorescent moieties (e.g., fluorescein, rhodamine, Texas Red, or phycoerythrin), chemiluminescent labels (e.g., using the PHOTO-GENE™ or ACES™ chemiluminescence systems, available commercially from Life Technologies (Carlsbad, Calif.)), dioxigenin and the like. Labeled nucleotides may also be obtained commercially, for example from Life Technologies (Carlsbad, Calif.) or Sigma Chemical Company (Saint Louis, Mo.). In some embodiments of the present compositions, the nucleotides are added to give a working concentration of each nucleotide of about 10-4000 micromolar, about 50-2000 micromolar, about 100-1500 micromolar, or about 200-1200 micromolar, or about 1000 micromolar.

In accordance with the present teachings, one or more agents can also be added to the present compositions to assist in overcoming the inhibition of RT reactions by a variety of compounds often found in samples used for nucleic acid preparation, isolation or purification. Such inhibitors can include, for example, heparin (blood); hematin (blood); EDTA (blood); citrate (blood); immunoglobin G (blood, serum); humic acid (soil, feces); lactoferrin (milk, saliva, other secretory fluids); urea urine); plant polysaccharides (plants); melanin (skin, hair); myoglobin (tissue); and indigo dye (textiles). Such agents for use in overcoming RT inhibition can include proteins such as, but not limited to, albumin (e.g. bovine serum albumin (BSA), recombinant BSA and albumins derived from other species), α-lacalbumin, β-lactoblogulin, casein, apotransferrin, spermine, gelatin (e.g., human recombinant gelatin, fish gelatin and gelatins derived from other species), and DNA-binding proteins (e.g., phage T4 gene 32 (T4gP32)), or peptide or polypeptide variants, fragments or derivatives thereof. Other non-protein based PCR inhibitor blocking agents for use in the present teachings can include, for example, deferoxamine mesylate. Some preferred proteins for use as PCR inhibitor blocking agents include bovine serum albumin (BSA), fish gelatin, and T4gP32 proteins. In some embodiments, anti-RT inhibitor agents are added to the present compositions to give a final concentration in a working solution of about 1 ng/µL to about 10,000 ng/µL, about 50 ng/µL to about 8000 ng/µL, about 100 ng/µL to about 6000 ng/µL, about 200 ng/µL to about 5000 ng/µL or preferably about 500 ng/µL to about 3000 ng/µL Anti-RT inhibitor agents can also be added as a percentage of the final concentration in a working solution, for example, from about 0.001% to about 15%, about 0.05% to about 10%, about 0.01% to about 5%, or preferably about 0.1% to about 1%. The addition of these anti-RT inhibitor agents, both individually or in combination, can increase tolerance to such RT inhibitor contaminants. Thus, the present compositions can further comprise agents that work alone or in combination to increase tolerance to various inhibitors including, for example, ethanol, bile salts, humic acid, hematin, and heparin.

In some embodiments, component deterioration can be reduced by storage of the reagent compositions at a temperature of about −80° C. (for up to two years) or at a temperature of about −20° C. (for up to one year).

In some embodiments, the present compositions can be packaged in a suitable container or vessel capable of holding the composition and which will not significantly interact with components of the composition. The container or vessel can be designed to permit easy dispensing of the dosage form by individuals or by a liquid handling instrument. The containers or vessels of such composition can be further packaged into multi-pack units.

In another aspect, the compositions and reverse transcriptases of the invention may be prepared and stored in dry form (e.g., lyophilized) in the presence of one or more carbohydrates, sugars, or synthetic polymers. Preferred carbohydrates, sugars or polymers for the preparation of dried compositions or reverse transcriptases include, but are not limited to, sucrose, trehalose, and polyvinylpyrrolidone (PVP) or combinations thereof. See, e.g., U.S. Pat. Nos. 5,098,893, 4,891,319, and 5,556,771, the disclosures of which are entirely incorporated herein by reference. Such dried compositions and enzymes may be stored at various temperatures for extended times without significant deterioration of enzymes or components of the compositions of the invention. In some preferred embodiments, the dried reverse transcriptases or compositions are stored at about −20° C. to about 25° C.

The invention further includes compositions for reverse transcribing nucleic acid molecules, as well as reverse transcription methods employing such compositions and product nucleic acid molecules produced using such methods. In many instances, compositions of the invention may contain one or more of the following components: (1) one or more buffering agent (e.g., sodium phosphate, sodium acetate, 2-(N-morpholino)-ethanesulfonic acid (MES), tris-(hydroxymethyl)aminomethane (Tris), 3-(cyclohexylarnino)-2-hydroxy-1-propanesulfonic acid (CAPS), citrate, N-2-hydroxyethylpiperazine-N-2-ethanesulfonic acid (HEPES), acetate, 3-(N-morpholino)propanesulfonic acid (MOPS), N-tris(hydroxymethyl)methyl-3-aminopropanesulfonio acid (TAPS), etc.), (2) one or more monovalent cationic salt (e.g., NaCl, KCl, etc.), (3) one or more divalent cationic salt (e.g., MnCl2, MgCl2, MgSO4, CaCl2, etc.), (4) one or more reducing agent (e.g., dithiothreitol, β-mercaptoethanol, etc.), (5) one or more ionic or non-ionic detergent (e.g., TRITON X-100™, NONIDET P40™, sodium dodecyl sulphate, etc.), (6) one or more DNA polymerase inhibitor (e.g., Actinomycin D, etc.), (7) nucleotides (e.g., dNTPs, such as dGTP, dATP, dCTP, dTTP, etc.), (8) RNA to be reverse transcribed and/or amplified, (9) one or more RNase inhibitor (e.g., RNASEOUT™, Invitrogen Corporation, Carlsbad, Calif., catalog number 10777-019 etc.), (10) a reverse transcriptase e.g., a reverse transcriptase of the invention, and/or (11) one or more diluent (e.g., water). Other components and/or constituents (e.g., primers, DNA polymerases, etc.) may also be present in compositions. In certain embodiments, compositions used for sequencing may contain one or more of the following components: (1) a single-stranded RNA template, (2) a primer, (3) nucleotides, (4) a label such as a radioactive label conjugated with the nucleotide base or a fluorescent label conjugated to the primer, and/or (5) a terminating agent, such as a chain terminator base comprising a dideoxynucleotide (ddATP, ddGTP, ddCTP, or ddTTP).

The concentration of the buffering agent in the compositions of the invention will vary with the particular buffering agent used. Typically, the working concentration i.e., the concentration in the reaction mixture) of the buffering agent will be from about 5 mM to about 500 mM (e.g., about 10 mM, about 15 mM, about 20 mM, about 25 mM, about 30 mM, about 35 mM, about 40 mM, about 45 mM, about 50 mM, about 55 mM about 60 mM, about 65 mM about 70 mM, about 75 mM, about 80 mM, about 85 mM, about 90 mM about 95 mM, about 100 mM, from about 5 mM to about 500 mM, from about 10 mM to about 500 mM, from about 20 mM to about 500 mM, from about 25 to about 500 mM, from about 30 mM to about 500 mM, from about 40 mM to about 500 mM, from about 50 mM to about 500 mM, from about 75 mM to about 500 mM, from about 100 mM to about 500 mM, from about 25 mM to about 50 mM, from about 25 mM to about 75 mM, from about 25 mM to about 100 mM, from about 25 mM to about 200 mM, from about 25 mM to about 300 mM, etc.). When Tris (e.g., Tris-HCl) is used, the Tris working concentration will typically be from about 5 mM to about 100 mM, from about 5 mM to about 75 mM, from about 10 mM to about 75 mM, from about 10 mM to about 60 mM, from about 10 mM to about 50 mM, from about 25 mM to about 50 mM, etc.

The final pH of solutions of the invention will generally be set and maintained by buffering agents present in compositions of the invention. The pH of compositions of the invention, and hence reaction mixtures of the invention, will vary with the particular use and the buffering agent present but will often be from about pH 5.5 to about pH 9.0 (e.g., about pH 6.0, about pH 6.5, about pH 7.0, about pH 7.1, about pH 7.2, about pH 7.3, about pH 7.4, about pH 7.5, about pH 7.6, about pH 7.7, about pH 7.8, about pH 7.9, about pH 8.0, about pH 8.1, about pH 8.2 about pH 8.3, about pH 8.4, about pH 8.5, about pH 8.6, about pH 8.7, about pH 8.8, about pH 8.9, about pH 9.0, from about pH 6.0 to about pH 8.5, from about pH 6.5 to about pH 8.5, from about pH 7.0 to about pH 8.5, from about pH 7.5 to about pH 8.5, from about pH 6.0 to about pH 8.0, from about pH 6.0 to about pH 7.7, from about pH 6.0 to about pH 7.5, from about pH 6.0 to about pH 7.0, from about pH 7.2 to about pH 7.7, from about pH 7.3 to about pH 7.7, from about pH 7.4 to about pH 7.6, from about pH 7.0 to about pH 7.4, from about pH 7.6 to about pH 8.0, from about pH 7.6 to about pH 8.5, from about pH 7.7 to about pH 8.5, from about pH 7.9 to about pH 8.5, from about pH 8.0 to about pH 8.5, from about pH 8.2 to about pH 8.5, from about pH 8.3 to about pH 8.5, from about pH 8.4 to about pH 8.5, from about pH 8.4 to about pH 9.0, from about pH 8.5 to about pH 9.0, etc.)

As indicated, one or more monovalent cationic salts (e.g., NaCl, KCl, etc.) may be included in compositions of the invention. In many instances, salts used in compositions of the invention will dissociate in solution to generate at least one species which is monovalent (e.g., Na+, K+, etc.) When included in compositions of the invention, salts will often be present either individually or in a combined concentration of from about 0.5 mM to about 500 mM (e.g., about 1 mM, about 2 mM, about 3 mM, about 5 mM, about 10 mM, about 12 mM, about 15 mM, about 17 mM, about 20 mM, about 22 mM, about 23 mM, about 24 mM, about 25 mM, about 27 mM, about 30 mM, about 35 mM, about 40 mM, about 45 mM, about 50 mM, about 55 mM, about 60 mM, about 64 mM, about 65 mM, about 70 mM, about 75 mM, about 80 mM, about 85 mM, about 90 mM, about 95 mM, about 100 mM, about 120 mM, about 140 mM, about 150 mM, about 175 mM, about 200 mM, about 225 about 250 mM, about 275 mM, about 300 mM, about 325 mM, about 350 about 375 mM, about 400 mM, from about 1 mM to about 500 mM, from about 5 mM to about 500 mM, from about 10 mM to about 500 mM, from about 20 mM to about 500 mM, from about 30 mM to about 500 mM, from about 40 mM to about 500 mM, from about 50 mM to about 500 mM, from about 60 mM to about 500 mM, from about 65 mM to about 500 mM, from about 75 mM to about 500 mM, from about 85 mM to about 500 mM, from about 90 mM to about 500 mM, from about 100 mM to about 500 mM, from about 125 mM to about 500 mM, from about 150 mM to about 500 mM, from about 200 mM to about 500 mM, from about 10 mM to about 100 mM, from about 10 mM to about 75 mM, from about 10 mM to about 50 mM, from about 20 mM to about 200 mM, from about 20 mM to about 150 mM, from about 20 mM to about 125 mM, from about 20 mM to about 100 mM, from about 20 mM to about 80 mM, from about 20 mM to about 75 mM, from about 20 mM to about 60 mM, from about 20 mM to about 50 mM, from about 30 mM to about 500 mM, from about 30 mM to about 100 mM, from about 30 mM to about 70 mM, from about 30 mM to about 50 mM, etc.

As indicated, one or more divalent cationic salts (e.g., $MnCl_2$, $MgCl_2$, $MgSO_4$, $CaCl_2$, etc.) may be included in compositions of the invention. In many instances, salts used in compositions of the invention will dissociate in solution to generate at least one species which is monovalent (e.g., $Mg^{++}$, $Mn^{++}$, $Ca^{++}$, etc.). When included in compositions of the invention, salts will often be present either individually or in a combined concentration of from about 0.5 mM to about 500 mM (e.g., about 1 mM, about 2 mM about 3 mM, about 4 mM, about 5 mM, about 6 mM, about 7 mM, about 8 mM, about 9 mM, about 10 mM, about 12 mM, about 15 mM, about 17 mM about 20 mM, about 22 mM, about 23 mM, about 24 mM, about 25 mM about 27 mM, about 30 mM, about 35 mM about 40 mM, about 45 mM, about 50 mM, about 55 mM, about 60 mM, about 64 mM, about 65 mM, about 70 mM, about 75 mM, about 80 mM, about 85 mM, about 90 mM, about 95 mM, about 100 mM, about 120 mM, about 140 mM, about 150 mM, about 175 mM, about 200 mM, about 225 mM, about 250 mM, about 275 mM, about 300 mM, about 325 mM, about 350 mM, about 375 mM, about 400 mM, from about 1 mM to about 500 mM, from about 5 mM to about 500 mM, from about 10 mM to about 500 mM, from about 20 mM to about 500 mM, from about 30 mM to about 500 mM, from about 40 mM to about 500 mM, from about 50 mM to about 500 mM, from about 60 mM to about 500 mM, from about 65 mM to about 500 mM, from about 75 mM to about 500 mM, from about 85 mM to about 500 mM, from about 90 mM to about 500 mM, from about 100 mM to about 500 mM, from about 125 mM to about 500 mM, from about 150 mM to about 500 mM, from about 200 mM to about 500 mM, from about 10 mM to about 100 mM, from about 10 mM to about 75 mM, from about 10 mM to about 50 mM, from about 20 mM to about 200 mM, from about 20 mM to about 150 mM, from about 20 mM to about 125 mM from about 20 mM to about 100 mM, from about 20 mM to about 80 mM, from about 20 mM to about 75 mM, from about 20 mM to about 60 mM, from about 20 mM to about 50 mM, from about 30 mM to about 500 mM, from about 30 mM to about 100 mM, from about 30 mM to about 70 mM, from about 30 mM to about 50 mM, etc.).

When included in compositions of the invention, reducing agents (e.g., dithiothreitol, β-mercaptoethanol, etc.) will often be present either individually or in a combined concentration of from about 0.1 mM to about 50 mM (e.g., about 0.2 mM, about 0.3 mM, about 0.5 mM, about 0.7 mM, about 0.9 mM, about 1 mM, about 2 mM, about 3 mM about 4 mM, about 5 mM, about 6 mM, about 10 mM, about 12 mM, about 15 mM, about 17 mM about 20 mM, about 22 mM, about 23 mM, about 24 mM, about 25 mM, about 27 mM, about 30 mM, about 35 mM, about 40 mM, about 45 mM, about 50 mM from about 0.1 mM to about 50 mM, from about 0.5 mM to about 50 mM, from about 1 mM to about 50 mM, from about 2 mM to about 50 mM, from about 3 mM to about 50 mM, from about 0.5 mM to about 20 mM, from about 0.5 mM to about 10 mM, from about 0.5 mM to about 5 mM, from about 0.5 mM 11 mM to about 2.5 mM from about 1 mM to about 20 mM, from about 1 mM to about 10 mM, from about 1 mM to about 5 mM, from about 1 mM to about 3.4 mM, from about 0.5 mM to about 3.0 mM, from about 1 mM to about 3.0 mM, from about 1.5 mM to about 3.0 mM, from about 2 mM to about 3.0 mM, from about 0.5 mM to about 2.5 mM, from about 1 mM to about 2.5 mM, from about 1.5 mM to about 2.5 mM, from about 2 mM to about 3.0 mM, from about 2.5 mM to about 3.0 mM, from about 0.5 mM to about 2 mM, from about 0.5 mM to about 1.5 mM, from about 0.5 mM to about 1.1 mM, from about 5.0 mM to about 10 mM from about 5.0 mM to about 15 mM, from about 5.0 mM to about 20 mM, from about 10 mM to about 15 mM, from about 10 mM to about 20 mM, etc.).

Compositions of the invention may also contain one or more ionic or non-ionic detergents (e.g., TRITON X-100™, NONIDET P40™, Tween 20, sodium dodecyl sulphate, etc.). When included in compositions of the invention, detergents will often be present either individually or in a combined concentration of from about 0.001% to about 5.0% (e.g., about 0.001%, about 0.002%, about 0.003%, about 0.004%, about 0.005%, about 0.006%, about 0.007%, about 0.008%, about 0.009%, about 0.01%, about 0.02%, about 0.05%, about 0.1, about 0.5%, about 1%, about %, about 5%, from about 0.001% to about 5.0%, from about 0.001% to about 4.0%, from about 0.001% to about 3.0%, from about 0.001% to about 2.0%, from about 0.001% to about 1.0%, from about 0.005% to about 5.0%, from about 0.01% to about 3.0%, from about 0.01% to about 2.0%, from about 0.01% to about 1.0%, from about 0.1% to about 5.0%, from about 0.1% to about 4.0%, from about 0.1% to about 3.0%, from about 0.1% to about 2.0%, from about 0.1% to about 1.0%, from about 0.1% to about 0.5%, etc.). For example, compositions of the invention may contain Tween 20, NP-40 and/or TRITON X100™ at a concentration of from about 0.01% to about 2.0%, from about 0.03% to about 1.0%, from about 0.04% to about 1.0%, from about 0.05% to about 0.5%, from about 0.04% to about 0.6%, from about 0.04% to about 0.3%, etc.

Other additives capable of facilitating or enhancing reverse transcription, amplification, or a combination of both reactions (e.g., agents for facilitating or enhancing RT-PCR), other than those disclosed herein, are known in the art. In accordance with the present compositions and methods, one or more of these additives can be incorporated in the present compositions to optimize the generation and replication of nucleic acids from a ribonucleic acid or deoxyribonucleic acid templates. Additives can be organic or inorganic compounds. Some additives useful in the present compositions, methods and kits Include polypeptides as well as nonpolypeptide additives. Such additives can include, for example, RNase inhibitor protein (RIP), uracil DNA glycosylase (UDG), lectins, *E. coli* single-stranded binding (SSB) protein, tRNA, rRNA, 7-deaza-2-deoxyguanosine (dC7GTP) sulfur-containing compounds, acetate-containing compounds, dimethylsulfoxide (DMSO), ribonuclease inhibitor (e.g., Rnase OUT™) formamide, betaine, tetramethylammonium chloride (TMAC) polyethylene glycol (PEG), ectoine, sodium azide, kathon, and polyols, to name just a few. Those of ordinary skill in the art will be able to identify additional additives for use in accordance with the present compositions, methods and kits.

Compositions of the invention may also contain one or more primers, in some embodiments, compositions of the invention comprise oligo(dT) primers. These primers are typically ~20 bases in length, and anneal to the polyA tails of mRNA. By targeting the mRNA fraction, the complexity of the resultant cDNA population is dramatically reduced, since rRNA and tRNA species will not serve as templates in the reaction. The drawback of using oligo(dT) primers is that the resultant cDNA population will have a 3' bias, thus compromising the effectiveness of PCR primers targeting the 5' ends of transcripts. In addition, due to the 3' bias, fragmented samples lacking a polyA tail will not be reverse transcribed.

In other embodiments, compositions of the invention comprise random primers. In some embodiments, the random primers are a random mixture of 4 bases of a specified oligo length. Random hexamer mixes, for example, can be used. Each of the random primers can anneal anywhere the complementary sequence exists within a given RNA molecule (including rRNA, tRNA, mRNA, and any fragments of these species). Reverse transcription using random primers overcomes concerns about RNA secondary structure, and RNA fragments, which are common headaches when using oligo(dT) primers.

In some other embodiments, compositions of the invention comprise locked nucleic acid (LNA) primers. The incorporation of LNA into oligonucleotide primers has been shown to increase template binding strength and specificity for DNA amplification. See, e.g., Ballantyne, K. N., et al., Genomics. 2008 March; 91(3):301-5.doi: 10.1016/j.ygeno.2007.10.016. LNA primers bind to polyA sequences with a higher melting temperature (Tm) than those that do not comprise LNA.

In other embodiments, compositions of the invention comprise sequence-specific (or gene-specific) primers. Sequence specific primers typically offer the greatest specificity and have been shown to be the most consistent of the primer options for reverse transcription. However, they do not offer the flexibility of oligo(dT) and random primers, meaning that a new cDNA synthesis reaction must be performed for each gene to be studied. This can sometimes makes sequence-specific primers less than optimal for processing limiting tissue or cell samples. In some embodiments, a mixture of different types of primers e.g., oligo(dT), random, LNA and/or sequence-specific primers are used.

Compositions of the invention may also comprise one or more hot start components. Hot-start is a common technique used to reduce nonspecific amplification due to assembly of nucleic acid synthesis reactions at room temperature. At lower temperatures, oligonucleotide primers can anneal to template sequences that are not perfectly complementary. Oftentimes, at these low temperatures enzymes such as reverse transcriptases can extend misannealed primers. This newly synthesized region then acts as a template for primer extension and synthesis of undesired nucleic acid synthesis products. However, if the reaction temperature is elevated (e.g., to temperatures ≥60° C.) before polymerization begins, the stringency of primer annealing is increased, and production of undesired nucleic acid synthesis products can be avoided or reduced.

The inclusion of hot start components in nucleic acid synthesis reactions can also reduce the amount of primer-dimer synthesized by increasing the stringency of primer annealing. At lower temperatures, oligonucleotide primers can anneal to each other via regions of complementarity to form hairpins, for example, and the reverse transcriptase can extend the annealed primers to produce primer dimers. The formation of nonspecific products and primer-dimers can compete for reagent availability for synthesis of the desired product. Thus, hot start techniques can improve the yield of specific nucleic acid synthesis products.

In some embodiments, hot start reactions are assembled on ice or at room temperature, with omission of a critical component until the reaction is heated to about 60° C., at which point the missing reagent is added. This omission prevents the reverse transcriptase from extending primers until the critical component is added at the higher temperature where primer annealing is more stringent.

In some other embodiments, the reverse transcriptase is reversibly inactivated or physically separated from one or more critical components in the reaction. For example, magnesium can be sequestered in a wax bead, which melts as the reaction is heated, releasing the component only at higher temperatures (see, e.g., Carothers et al. 1989; Krishnan et al. 1991; Clark, 1988). The reverse transcriptase can also be kept in an inactive state by binding to an oligonucleotide, also known as an aptamer (see, e.g., Lin and Jayasena, 1997; Dang and Jayasena, 1996) or an antibody (see, e.g., Scalice et al. 1994; Sharkey et al, 1994). This bond can then be disrupted at a higher temperature, releasing the functional reverse transcriptase.

In yet other embodiments, the reverse transcriptase can be maintained in an inactive state through chemical modification (see, e.g., Moretti, T. et al 1998). In some embodiments, the chemical modification is reversible. Thus, in some embodiments, the reverse transcriptase is chemically modified such that it is in an inactive state at a lower temperature (e.g., less than about 55° C.) and is fully functional/active at an elevated temperature (e.g., greater than about 55° C.).

Compositions of the invention may also contain one or more DNA polymerase inhibitors (e.g., Actinomycin D, etc.). When included in compositions of the invention, such inhibitors will often be present either individually or in a combined concentration of from about 0.1 µg/ml about 100 µg/ml (e.g., about 0.1 µg/ml, about 0.2 µg/ml about 0.3 µg/ml, about 0.4 µg/ml, about 0.5 µg/ml, about 0.6 µg/ml about 0.7 µg/ml, about 0.8 µg/ml, about 0.9 µg/ml, about 1.0 µg/ml, about 1.1 µg/ml, about 1.3 µg/ml, about 1.5 µg/ml, about 1.7 µg/ml, about 2.0 µg/ml, about 2.5 µg/ml, about 3.5 µg/ml, about 5.0 µg/ml, about 7.5 µg/ml, about 10 µg/ml, about 15 µg/ml, about 20 µg/ml, about 25 µg/ml, about 30 µg/ml, about 35 µg/ml, about 40 µg/ml, about 50 µg/ml, about 60 µg/ml, about 70 µg/ml, about 80 µg/ml, about 90 µg/ml, about 100 µg/ml, from about 0.5 µg/ml to about 30 µg/ml from about 0.75 µg/ml to about 30 µg/ml, from about 1.0 µg/ml to about 30 µg/ml, from about 2.0 µg/ml to about 30 µg/ml, from about 3.0 µg/ml to about 30 µg/ml, from about 4.0 µg/ml to about 30 µg/ml from about 5.0 µg/ml to about 30 µg/ml, from about 7.5 µg/ml to about 30 µg/ml, from about 10 µg/ml to about 30 µg/ml, from about 15 µg/ml about 30 µg/ml, from about 0.5 µg/ml to about 20 µg/ml, from about 0.5 µg/ml about 10 µg/ml, from about 0.5 µg/ml 1 to about 5 µg/ml, from about 0.5 µg/ml to about 2 µg/ml, from about 0.5 µg/ml to about 1 µg/ml, from about 1 µg/ml 1 µg/ml to about 10 µg/ml, from about 1 µg/ml to about 5 µg/ml, from about 1 µg/ml to about 2 µg/ml, from about 1 µg/ml to about 100 µg/ml, from about 10 µg/ml to about 100 µg/ml, from about 20 µg/ml to about 100 µg/ml, from about 40 µg/ml to about 100 µg/ml, from about 30 µg/ml to about 80 µg/ml, from about 30 µg/ml to about 70 µg/ml, from about 40 µg/ml to about 60 µg/ml, from about 40 µg/ml to about 70 µg/ml, from about 40 g/ml to about 80 µg/ml, etc.).

In many instances, nucleotides e.g., dNTPs, such as dGTP, dATP, dCTP, dTTP, etc. will be present in reaction mixtures of the invention. Typically, individually nucleotides will be present in concentrations of from about 0.05 mM to about 50 mM (e.g., about 0.07 mM, about 0.1 mM, about 0.15 mM, about 0.18 mM, about 0.2 mM, about 0.3 mM, about 0.5 mM, about 0.7 mM, about 0.9 mM, about 1 mM, about 2 mM, about 3 mM about 4 mM, about 5 mM, about 6 mM, about 10 mM, about 12 mM, about 15 mM, about 17 mM, about 20 mM, about 22 mM, about 23 mM, about 24 mM, about 25 mM, about 27 mM, about 30 mM, about 35 mM, about 40 mM, about 45 mM, about 50 mM, from about 0.1 mM to about 50 mM, from about 0.5 mM to about 50 mM, from about 1 mM to about 50 mM, from about 2 mM to about 50 mM, from about 3 mM to about 50 mM, from about 0.5 mM to about 20 mM, from about 0.5 mM to about 10 mM, from about 0.5 mM to about 5 mM, from about 0.5 mM to about 2.5 mM, from about 1 mM to about 20 mM, from about 1 mM to about 10 mM, from about 1 mM to about 5 mM, from about 1 mM to about 3.4 mM, from about 0.5 mM to about 3.0 mM, from about 1 mM to about 3.0 mM, from about 1.5 mM to about 3.0 mM, from about 2 mM to about 3.0 mM, from about 0.5 mM to about 2.5 mM, from about 1 mM to about 2.5 mM, from about 1.5 mM to about 2.5 mM, from about 2 mM to about 3.0 mM, from about 2.5 mM to about 3.0 mM, from about 0.5 mM to about 2 mM, from about 0.5 mM to about 1.5 mM, from about 0.5 mM to about 1.1 mM, from about 5.0 mM to about 10 mM, from about 5.0 mM to about 15 mM, from about 5.0 mM to about 20 mM from about 10 mM to about 15 mM, from about 10 mM to about 20 mM, etc.). The combined nucleotide concentration, when more than one nucleotides is present, can be determined by adding the concentrations of the individual nucleotides together. When more than one nucleotide is present in compositions of the invention, the individual nucleotides may not be present in equimolar amounts. Thus, a composition may contain, for example, 1 mM dGTP, 1 mM dATP, 0.5 mM dCTP and 1 mM dTTP.

RNA will typically be present in compositions of the invention. In most instances, RNA will be added to the composition shortly prior to reverse transcription. Thus, compositions may be provided without RNA. This will typically be the case when compositions are provided in kits. RNA, when present in compositions will often be present in a concentration of 1 picogram to 100 µg/20 µl reaction mixture (e.g., about 1 picogram/20 µl, about 10 picograms/20 µl, about 50 picograms/20 µl, about 100 picograms/20 µl, about 200 picograms/20 µl, about 10 picograms/20 µl, about 500 picograms/20 µl, about 800 picograms/20 µl, about 1.0 nanogram/20 µl, about 5.0 nanograms/20 µl, about 10 nanograms/20 µl, about 25 nanograms/20 µl, about 50 nanograms/20 µl, about 75 nanograms/20 µl, about 100 nanograms/20 µl, about 150 nanograms/20 µl, about 250 nanograms/20 µl, about 400 nanograms/20 µl, about 500 nanograms/20 µl, about 750 nanograms/20 µl, about 1.0 µg/20 about 5.0 µg/20 µl, about 10 µg/20 µl, about 20 µg/20 µl, about 30 µg/20 µl, about 40 µg/20 µl, about 50 µg/20 µl, about 70 µg/20 µl, about 100 µg/20 µl, from about 10 picograms/20 µl to about 100 µg/20 µl, from about 10 picograms/20 µl to about 100 µg/20 µl, from about 100 picograms/20 µl to about 100 µg/20 µl, from about 1.0 nanograms/20 µl to about 100 µl, from about 100 nanograms/20 µl to about 100 µl, from about 10 picograms/20 µl to about 10 µg/20 µl, from about 10 picograms/20 µl to about 5 µg/20 µl, from about 100 nanograms/20 µl to about 5 µg/20 µl, from about 1 µg/20 µl to about 10 µg/20 µl, from about 1 µg/20 µl to about 5 µg/20 µl, from about 100 nanograms/20 µl to about 1 µg/20 µl, from about 500 nanograms/20 µl to about 5 µg/20 µl, etc.). As one skilled in the art would recognize, different reverse transcription reactions may be performed in volumes other than 20 µl. In such instances, the total amount of RNA present will vary with the volume used. Thus, the above amounts are provided as examples of the amount of RNA/20 µl of composition.

Mutant reverse transcriptases of the invention when present in compositions as described herein (storage compositions and/or reaction mixtures), can be present in a concentration which results in about 0.01 to about 1,000 units of reverse transcriptase activity/µl (e.g., about 0.01 unit/µl, about 0.05 unit/µl, about 0.1 unit/µl, about 0.2 unit/µl, about 0.3 unit/µl about 0.4 unit/µl, about 0.5 unit/µl, about 0.7 unit/µl, about 1.0 unit/µl, about 1.5 unit/µl, about 2.0 unit/µl, about 2.5 unit/µl, about 5.0 unit/µl, about 7.5 unit/µl, about 10 unit/µl, about 20 unit/µl, about 25 unit/µl, about 50 unit/µl about 100 unit/µl, about 150 unit/µl, about 200 unit/µl, about 250 unit/µl, about 350 unit/µl, about 500 unit/µl, about 750 unit/µl, about 1,000 unit/µl, from about 0.1 unit/µl to about 1,000 unit/µl, from about 0.2 unit/µl to about 1,000 unit/µl, from about 1.0 unit/µl about 1,000 unit/µl, from about 5.0 unit/µl to about 1,000 unit/µl, from about 10 unit/µl to about 1,000 unit/µl, from about 20 unit/µl to about 1,000 unit/µl, from about 50 unit/µl to about 1,000 unit/µl, from about 100 unit/µl to about 1,000 unit/µl, from about 200 unit/µl to about 1,000 unit/µl, from about 400 unit/µl to about 1,000 unit/µl, from about 500 unit/µl to about 1,000 unit/µl, from about 0.1 unit/µl about 300 unit/µl, from about 0.1 unit/µl to about 200 unit/µl, from about 0.1 unit/µl to about 100 unit/µl, from about 0.1 unit/µl to about 50 unit/µl, from about 0.1 unit/µl about 10 unit/µl, from about 0.1 unit/µl about 5.0 unit/µl, from about 0.1 unit/µl to about 1.0 unit/µl, from about 0.2 unit/µl to about 0.5 unit/µl, etc.

Compositions of the invention may be prepared as concentrated solutions (e.g., 5× solutions) which are diluted to a working concentration for final use. With respect to a 5× composition, a 5:1 dilution is required to bring such a 5× solution to a working concentration. Compositions of the invention may be prepared, for examples, as a 2×, a 3×, a 4×, a 5×, a 6×, a 7×, a 8×, a 10×, etc. solutions. One limitation on the fold concentration of such solutions is that, when compounds reach particular concentrations in solution, precipitation can occur. Thus, concentrated compositions will generally be prepared such that the concentrations of the various components are low enough so that precipitation of buffer components will not occur. As one skilled in the art would recognize, the upper limit of concentration which is feasible for each solution will vary with the particular solution and the components present.

In many instances, compositions of the invention will be provided in sterile form. Sterilization may be performed on the individual components of compositions prior to mixing or on compositions after they are prepared. Sterilization of such solutions may be performed by any suitable means including autoclaving or ultrafiltration.

Methods of Using Reverse Transcriptases

The reverse transcriptases of the invention may be used to make nucleic acid molecules from one or more templates. Such methods can comprise mixing one or more nucleic acid templates (e.g., DNA or RNA, such as non-coding RNA (ncRNA), messenger RNA (mRNA), micro RNA (miRNA), and small interfering RNA (siRNA) molecules) with one or more of the reverse transcriptases of the invention and incubating the mixture under conditions sufficient to make one or more nucleic acid molecules complementary to all or a portion of the one or more nucleic acid templates.

The invention also concerns nucleic acid molecules produced by such methods (which may be full-length cDNA molecules), vectors (particularly expression vectors) comprising these nucleic acid molecules and host cells comprising these vectors and nucleic acid molecules.

Other methods of cDNA synthesis which may advantageously use the present invention will be readily apparent to one of ordinary skill in the art.

The invention also provides methods for the amplification of one or more nucleic acid molecules comprising mixing one or more nucleic acid templates with one of the reverse transcriptases of the invention, and incubating the mixture under conditions sufficient to amplify one or more nucleic acid molecules complementary to all or a portion of the one or more nucleic acid templates. Such amplification methods may further comprise the use of one or more DNA polymerases and may be employed as in standard reverse transcription-polymerase chain reaction (RT-PCR) reactions.

Nucleic acid amplification methods according to this aspect of the invention may be one-step (e.g., one-step RT-PCR) or two-step (e.g., two-step RT-PCR) reactions. According to the invention, one-step RT-PCR type reactions may be accomplished in one tube thereby lowering the possibility of contamination. Such one-step reactions comprise (a) mixing a nucleic acid template (e.g., mRNA) with one or more reverse transcriptases of the present invention and with one or more DNA polymerases and (b) incubating the mixture under conditions sufficient to amplify a nucleic acid molecule complementary to all or a portion of the template. Such amplification may be accomplished by the reverse transcriptase activity alone or in combination with the DNA polymerase activity. Two-step RT-PCR reactions may be accomplished in two separate steps. Such a method comprises (a) mixing a nucleic acid template (e.g., mRNA) with a reverse transcriptase of the present invention, (b) incubating the mixture under conditions sufficient to make a nucleic acid molecule (e.g., a DNA molecule) complementary to all or a portion of the template, (c) mixing the nucleic acid molecule with one or more DNA polymerases and (d) incubating the mixture of step (c) under conditions sufficient to amplify the nucleic acid molecule. For amplification of long nucleic acid molecules (i.e., greater than about 3-5 kb in length), a combination of DNA polymerases may be used, such as one DNA polymerase having 3 exonuclease activity and another DNA polymerase being substantially reduced in 3 exonuclease activity.

Amplification methods which may be used in accordance with the present invention include PCR (see, e.g., U.S. Pat. Nos. 4,683,195 and 4,683,202), Isothermal Amplification (using one or more RNA polymerases (see, e.g., PCT Publication No. WO 2006/081222), Strand Displacement Amplification (SDA; see, e.g., U.S. Pat. No. 5,455,166; EP 0 684 315), and Nucleic Acid Sequence-Based Amplification (NASBA; see, e.g., U.S. Pat. No. 5,409,818; EP 0 329 822), as well as more complex PCR-based nucleic acid fingerprinting techniques such as Random Amplified Polymorphic DNA (RAPD) analysis (see, e.g., Williams, J. G. K., et al., Nucl. Acids Res. 18(22):6531-6535, 1990), Arbitrarily Primed PCR (AP-PCR; see, e.g., Welsh, J., and McClelland, M., Nucl. Acids Res. 18(24):7213-7218, 1990), DNA Amplification Fingerprinting (DAF; see, e.g., Caetano-Anollés et al., Bio/Technology 9:553-557, 1991), microsatellite PCR or Directed Amplification of Minisatellite-region DNA (DAVID; see, e.g., Heath, D. D., et al. Nucl. Acids Res. 21(24): 5782-5785 (1993), and Amplification Fragment Length Polymorphism (AFLP) analysis (see, e.g., EP 0 534 858; Vos, P., et al. Nucl. Acids Res. 23(21):4407-4414 (1995); Lin, J. J., and Kuo, J. FOCUS 17(2):66-70 (1995). Nucleic acid sequencing techniques which may employ the present compositions include dideoxy sequencing methods such as those disclosed in U.S. Pat. Nos. 4,962,022 and 5,498,523. In some embodiments, the invention may be used in methods of amplifying or sequencing a nucleic acid molecule comprising one or more polymerase chain reactions (PCRs), such as any of the PCR-based methods described above.

The invention also concerns methods for the sequencing of one or more nucleic acid molecules comprising (a) mixing one or more nucleic acid molecules to be sequenced with one or more primer nucleic acid molecules, one or more reverse transcriptases of the invention, one or more nucleotides and one or more terminating agents; (b) incubating the mixture under conditions sufficient to synthesize a population of nucleic acid molecules complementary to all or a portion of the one or more nucleic acid molecules to be sequenced; and (c) separating the population of nucleic acid molecules to determine the nucleotide sequence of all or a portion of the one or more nucleic acid molecules to be sequenced.

Nucleic acid sequencing methods according to this aspect of the invention can comprise both cycle sequencing (sequencing in combination with amplification) and standard sequencing reactions. The sequencing method of the invention thus comprises (a) mixing a nucleic acid molecule to be sequenced with one or more primers, one or more reverse transcriptase of the invention, one or more nucleotides and one or more terminating agents, (b) incubating the mixture under conditions sufficient to synthesize a population of nucleic acid molecules complementary to all or a portion of the molecule to be sequenced, and (c) separating the population to determine the nucleotide sequence of all or a portion of the molecule to be sequenced. According to the invention, one or more DNA polymerases (preferably thermostable DNA polymerases) can be used in combination with or separate from the reverse transcriptases of the invention.

In accordance with the invention, cDNA molecules (single-stranded or double-stranded) can be prepared from a variety of nucleic acid template molecules using the novel mutant reverse transcriptases provided herein. Preferred nucleic acid molecules for use in the present invention include single-stranded or double-stranded DNA and RNA molecules, as well as double-stranded DNA:RNA hybrids. More preferred nucleic acid molecules include messenger RNA (mRNA), transfer RNA (tRNA) and ribosomal RNA (rRNA) molecules, although mRNA molecules are the preferred template according to the invention. In certain embodiments gene-specific primers can be used. In certain other embodiments in which at least some of the mutant reverse transcriptases provided herein are well-suited, oligo dT primers are used. These dT primers can be LNA primers in some embodiments. Furthermore, in illustrative examples, the templates for such reactions can be mRNA.

The nucleic acid molecules that are used to prepare cDNA molecules according to the methods of the present invention may be prepared synthetically according to standard organic chemical synthesis methods that will be familiar to one of ordinary skill. More preferably, the nucleic acid molecules may be obtained from natural sources, such as a variety of cells, tissues, organs or organisms. Cells that may be used as sources of nucleic acid molecules may be prokaryotic (bacterial cells, including but not limited to those of species of the genera *Escherichia, Bacillus, Serratia, Salmonella, Staphylococcus, Streptococcus, Clostridium, Chlamydia, Neisseria, Treponema, Mycoplasma, Borrelia, Legionella, Pseudomonas, Mycobacterium, Helicobacter, Erwinia, Agrobacterium, Rhizobium, Xanthomonas* and *Streptomyces*) or eukaryotic (including fungi (especially yeasts), plants, protozoans and other parasites, and animals including insects (particularly *Drosophila* spp. cells), nematodes (particularly *Caenorhabditis elegans* cells), and mammals (particularly human cells)).

Mammalian somatic cells that may be used as sources of nucleic acids include blood cells (reticulocytes and leukocytes), endothelial cells, epithelial cells, neuronal cells (from the central or peripheral nervous systems), muscle cells (including myocytes and myoblasts from skeletal, smooth or cardiac muscle), connective tissue cells (including fibroblasts, adipocytes, chondrocytes, chondroblasts, osteocytes and osteoblasts) and other stromal cells (e.g., macrophages, dendritic cells, Schwann cells). Mammalian germ cells (spermatocytes and oocytes) may also be used as sources of nucleic acids for use in the invention, as may the progenitors, precursors and stem cells that give rise to the above somatic and germ cells. Also suitable for use as nucleic acid sources are mammalian tissues or organs such as those derived from brain, kidney, liver, pancreas, blood, bone marrow, muscle, nervous, skin, genitourinary, circulatory, lymphoid, gastrointestinal and connective tissue sources, as well as those derived from a mammalian (including human) embryo or fetus.

Any of the above prokaryotic or eukaryotic cells, tissues and organs may be normal, diseased, transformed, established, progenitors, precursors, fetal or embryonic. Diseased cells may, for example, include those involved in infectious diseases (caused by bacteria, fungi or yeast, viruses (including AIDS, HIV, HTLV, herpes, hepatitis and the like) or parasites), in genetic or biochemical pathologies (e.g., cystic fibrosis, hemophilia, Alzheimer's disease, muscular dystrophy or multiple sclerosis) or in cancerous processes. Transformed or established animal cell lines may include, for example, COS cells, CHO cells, VERO cells, BHK cells, HeLa cells, HepG2 cells, K562 cells, 293 cells, L929 cells, F9 cells, and the like. Other cells, cell lines, tissues, organs and organisms suitable as sources of nucleic acids for use in the present invention will be apparent to one of ordinary skill in the art.

In some embodiments, a composition can comprise genomic nucleic acid. In some embodiments, a composition can comprise maternal nucleic acid, fetal nucleic acid or a mixture of maternal and fetal nucleic acids. In some embodiments, a composition can comprise fragments of genomic nucleic acids. In some embodiments a composition can comprise nucleic acids derived from a virus, bacteria, yeast, fungus, mammal or mixture thereof. A nucleic acid sample may be derived from one or more sources. A sample may be collected from an organism, mineral or geological site (e.g., soil, rock, mineral deposit, fossil), or forensic site (e.g., crime scene, contraband or suspected contraband), for example. Thus, a source may be environmental, such as geological, agricultural, combat theater or soil sources, for example. A source also may be from any type of organism such as any plant, fungus, protistan, moneran, virus or animal, including but not limited, human, non-human, mammal, reptile, cattle, cat, dog, goat, swine, pig, monkey, ape, gorilla, bull, cow, bear, horse, sheep, poultry, mouse, rat, fish, dolphin, whale, and shark, or any animal or organism that may have a detectable nucleic acids. Sources also can refer to different parts of an organism such as internal parts, external parts, living or nonliving cells, tissue, fluid and the like. A sample therefore may be a "biological sample," which refers to any material obtained from a living source or formerly-living source, for example, an animal such as a human or other mammal, a plant, a bacterium, a fungus, a protist or a virus. A source can be in any form, including, without limitation, a solid material such as a tissue, cells, a cell pellet, a cell extract, or a biopsy, or a biological fluid such as urine, blood, saliva, amniotic fluid, exudate from a region of infection or inflammation, or a mouth wash containing buccal cells, hair, cerebral spinal fluid and synovial fluid and organs. A sample also may be isolated at a different time point as compared to another sample, where each of the samples are from the same or a different source. A nucleic acid may be from a nucleic acid library, such as a cDNA or RNA library, for example. A nucleic acid may be a result of nucleic acid purification or isolation and/or amplification of nucleic acid molecules from the sample.

Nucleic acid provided for sequence analysis processes described herein may contain nucleic acid from one sample or from two or more samples (e.g., from 1, 2, 3, 4, 5, 6, 7, 8, 9, 10, 1 1, 12, 13, 14, 15, 16, 17, 18, 19, 20, 25, 50, 75, 100, 200, 300, 400, 500, 600, 700, 800, 900 or 1000 or more samples). Nucleic acids may be treated in a variety of manners. For example, a nucleic acid may be reduced in size (e.g., sheared, digested by nuclease or restriction enzyme, de-phosphorylated, de-methylated), increased in size (e.g., phosphorylated, reacted with a methylation-specific reagent, attached to a detectable label), treated with inhibitors of nucleic acid cleavage and the like.

Nucleic acids may be provided for conducting methods described herein without processing, in certain embodiments. In some embodiments, nucleic acid is provided for conducting methods described herein after processing. For example, a nucleic acid may be extracted, isolated, purified or amplified from a sample. The term "isolated" as used herein refers to nucleic acid removed from its original environment (e.g., the natural environment if it is naturally occurring, or a host cell if expressed exogenously), and thus is altered "by the hand of man" from its original environment. An isolated nucleic acid generally is provided with fewer non-nucleic acid components (e.g., protein, lipid) than the amount of components present in a source sample. A composition comprising isolated nucleic acid can be substantially isolated (e.g., about 90%, 91%, 92%, 93%, 94%, 95%, 96%, 97%, 98%, 99% or greater than 99% free of non-nucleic acid components). The term "purified" as used herein refers to nucleic acid provided that contains fewer nucleic acid species than in the sample source from which the nucleic acid is derived. A composition comprising nucleic acid may be substantially purified (e.g., about 90%, 91%, 92%, 93%, 94%, 95%, 96%, 97%, 98%, 99% or greater than 99% free of other nucleic acid species).

Nucleic acids may be processed by a method that generates nucleic acid fragments, in certain embodiments, before providing nucleic acid for a process described herein. In some embodiments, nucleic acid subjected to fragmentation or cleavage may have a nominal, average or mean length of about 5 to about 10,000 base pairs, about 100 to about 1,00 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000 or 10000 base pairs. Fragments can be generated by any suitable method known in the art, and the average, mean or nominal length of nucleic acid fragments can be controlled by selecting an appropriate fragment-generating procedure. In certain embodiments, nucleic acid of a relatively shorter length can be utilized to analyze sequences that contain little sequence variation and/or contain relatively large amounts of known nucleotide sequence information. In some embodiments, nucleic acid of a relatively longer length can be utilized to analyze sequences that contain greater sequence variation and/or contain relatively small amounts of unknown nucleotide sequence information. As used herein, the term "target nucleic acid" or "target nucleic acid species" refers to any nucleic acid species of interest in a sample. A target nucleic acid includes, without limitation, (i) a particular allele amongst two or more possible alleles, and (ii) a nucleic acid having, or not having, a particular mutation, nucleotide substitution, sequence variation, repeat sequence, marker or distinguishing sequence.

Once the starting cells, tissues, organs or other samples are obtained, nucleic acid molecules (such as mRNA) may be isolated therefrom by methods that are well-known in the art (See, e.g., Maniatis, T., et al., Cell 15:687-701 (1978); Okayama, H., and Berg, P., Mol. Cell. Biol. 2:161-170 (1982); Gubler, U., and Hoffman, B. J., Gene 25:263-269 (1983)). The nucleic acid molecules thus isolated may then be used to prepare cDNA molecules and cDNA libraries in accordance with the present invention.

Kits

In another embodiment, the present invention may be assembled into kits, which may be used in reverse transcription or amplification of a nucleic acid molecule, or into kits for use in sequencing of a nucleic acid molecule. Kits according to this aspect of the invention comprise a carrier means, such as a box, carton, tube or the like, having in close confinement therein one or more container means, such as vials, tubes, ampoules, bottles and the like, wherein a first container means contains one or more polypeptides of the present invention having reverse transcriptase activity. When more than one polypeptide having reverse transcriptase activity is used, they may be in a single container as mixtures of two or more polypeptides, or in separate containers. The kits of the invention can also comprise (in the same or separate containers) one or more DNA polymerases, a suitable buffer, one or more nucleotides and/or one or more primers. The kits of the invention can also comprise one or more hosts or cells including those that are competent to take up nucleic acids (e.g., DNA molecules including vectors). Preferred hosts may include chemically competent or electrocompetent bacteria such as E. coli (including DH5, DH5α, DH10B, HB101, Top 10, and other K-12 strains as well as E. coli B and E. coli W strains).

In a specific aspect of the invention, the kits of the invention (e.g., reverse transcription and amplification kits) can include one or more components (in mixtures or separately) including one or more polypeptides having reverse transcriptase activity of the invention, one or more nucleotides (one or more of which may be labeled, e.g., fluorescently labeled) used for synthesis of a nucleic acid molecule, and/or one or more primers (e.g., oligo(dT) for reverse transcription). Such kits (including the reverse transcription and amplification kits) can further comprise one or more DNA polymerases. Sequencing kits of the invention may comprise one or more polypeptides having reverse transcriptase activity of the invention, and optionally one or more DNA polymerases, one or more terminating agents (e.g., dideoxynucleoside triphosphate molecules) used for sequencing of a nucleic acid molecule, one or more nucleotides and/or one or more primers. Preferred polypeptides having reverse transcriptase activity, DNA polymerases, nucleotides, primers and other components suitable for use in the reverse transcription, amplification and sequencing kits of the invention include those described above. The kits encompassed by this aspect of the present invention may further comprise additional reagents and compounds necessary for carrying out standard nucleic acid reverse transcription, amplification or sequencing protocols. Such polypeptides having reverse transcriptase activity of the invention, DNA polymerases, nucleotides, primers, and additional reagents, components or compounds can be contained in one or more containers, and can be contained in such containers in a mixture of two or more of the above-noted components or may be contained in the kits of the invention in separate containers. Such kits can also comprise instructions (e.g., for performing the methods of the invention such as for labeling nucleic acid molecules in accordance with the invention).

In certain illustrative embodiments, the kits of the invention are prepared for molecular diagnostics assays. The kits can be approved by a government regulatory agency that regulates the sale of diagnostics products for human diagnostics, animal diagnostics, environmental diagnostics and/or food safety. The reverse transcriptases of the present invention can be provided in place of current reverse transcriptases in such kits. Furthermore, the advantageous and surprising properties of the novel reverse transcriptases of the present invention make them particularly well-suited for these applications.

In some embodiments, the kits of the invention include one or more components, including, but not limited to: an internal and/or external positive control, a set of oligonucleotides for detection of the target gene (e.g., primer and/or probe), lysis buffer, uracil DNA glycosylase (UDG), a master mix, and a detection dye.

It will be readily apparent to one of ordinary skill in the relevant arts that other suitable modifications and adaptations to the methods and applications described herein are obvious and may be made without departing from the scope of the invention or any embodiment thereof. Section headings provided herein are for convenience only. Having now described the present invention in detail, the same will be more clearly understood by reference to the following examples, which are included herewith for purposes of illustration only and are not intended to be limiting of the invention.

EXAMPLES

Example 1

Comparison of Thermostability and Processivity of Various Reverse Transcriptases 2 µg of 0.24-9.5 kb RNA Ladder (Invitrogen, Cat. No. 15620016) and 5 µM of 5' labeled oligo(dT)$_{20}$ primer (SEQ ID NO: 5) (Alexa-647) was added to a final reaction volume of 19 µL of 1× 1st strand cDNA synthesis buffer, pH 8.4 (Life Technologies, Cat. No. Y02321) supplemented with 10 mM DTT, 500 µM of each dNTP (dATP, dTTP, dGTP and dCTP), and 2U RNaseOut (Invitrogen, Cat. No. 10777-019) and incubated on ice. Reactions were then initiated by adding 1 µL of a reverse transcriptase (200U/µl) (to a final volume 20 µL) followed by incubation at 60° C., 37° C., 42° C., or 50° C. (as indicated in FIG. 2) for various lengths of time (i.e., 5 minutes, 15 minutes and 60 minutes). At the end of each time point, the reactions were terminated by addition of 10 µl of alkaline loading dye (300 mM NaOH, 2 mM EDTA, 20% glycerol, 10% saturated Thymol Blue) and visualized by electrophoresis on a 1% alkaline agarose gel (30 mM NaOH, 2 mM EDTA pH 7.5) in buffer (30 mM NaOH, 2 mM EDTA pH 7.5) for 2-4 hours at 30 volts. The gel was then analyzed by Molecular Dynamics Typhoon 8600 Variable Mode Imager (Harlow Scientific) using ImageQuant software.

As FIG. 2 shows, reactions that include mutant M-MLV RT "Mut D9" (SEQ ID NO:4), an exemplary mutant M-MLV constructed using the teachings herein, produced cDNAs up to 7.5 kb as early as 5 minutes after incubation and cDNAs up to 9.5 kb after only 15 minutes of incubation at 60° C. This is in contrast to reactions comprising wild type M-MLV RT incubated at 37° C. which required up to 60 minutes to produce a comparable amount of 7.5 kb cDNAs. Similarly, 7.5 kb cDNAs were not detected in reactions comprising either SuperScript™ II ("SSII") or SuperScript™ III ("SSIII")RTs until more than 5 minutes of incubation at 42° C. or 50° C., respectively. Another commercially available RT ("Q-RT") that was examined did not produce any similar cDNAs even after 60 minutes of incubation at 37° C. This demonstrates that mutant M-MLV ("Mut D9") RT was highly processive and exhibited increased thermostability, as well as thermoreactivity, in reverse transcription reactions performed at temperatures as high as 60° C.

Example 2

Mutant Reverse Transcriptase Stability at Low pH

Figure 3:
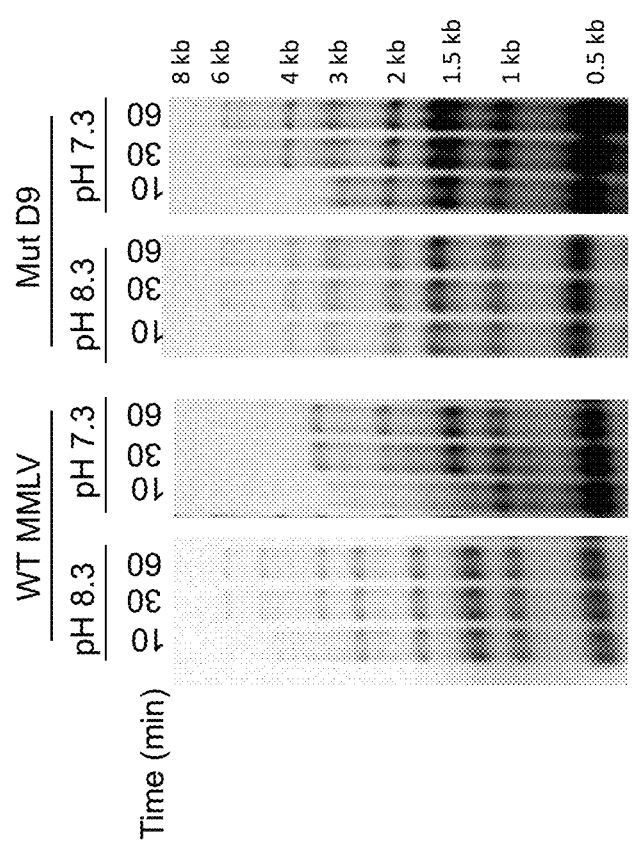
FIG. 3 is a fluorescent image showing RT activity of an exemplary mutant M-MLV reverse transcriptase as disclosed herein ("Mut D9"; SEQ ID NO:4) compared to wild type M-MLV reverse transcriptase ("WT MMLV"; SEQ ID NO:2). Each lane shows the cDNA products obtained from RT reactions carried out for varying lengths of time (i.e., 10 minutes, 30 minutes or 60 minutes) either at 37° C. (for WT MMLV) or 50° C. (for Mut D) and under pH 8.3 or 7.3, as indicated. A 0.5 to 10 kb RNA ladder was used as the template nucleic acid for each reaction.

Comparison of wild type M-MLV RT (Invitrogen™, Catalog #28025-013) ("WT MMLV") and an exemplary mutant M-MLV RT ("Mut D9") was performed to evaluate speed and length of cDNA synthesized at varying pH. These assays contained 0.5-10 kb RNA ladder (Ambion®, Catalog #15623-200) and Alexa Fluor® 647 oligo(dT)20 (SEQ ID NO: 5) and was performed with a standard pH 8.3 buffer (50 mM Tris-HCl pH 8.3, 72.5 mM KCl, and 3 mM MgCl2) or a pH 7.3 buffer (50 mM Tris-HCl pH 7.3, 72.5 mM KCl, and 3 mM MgCl2). Reaction temperatures were 37° C. for wild type M-MLV and 50° C. for Mut D9 and RT reactions were carried out for varying lengths of time (i.e., 10 minutes, 30 minutes or 60 minutes, as indicated in FIG. 3). The first strand cDNAs produced were resolved by alkaline agarose gel electrophoresis and visualized using Molecular Dynamics Typhoon 8600 Variable Mode Imager (Harlow Scientific) set at Cy5 fluorescent mode.

As FIG. 3 shows, at pH 8.3, Mut D9 reaches 4 kb by 10 minutes while wild type M-MLV reaches only 3 kb in the same amount of time. At pH 7.3, Mutant D9 can reach 4 kb in 30 minutes whereas wild type M-MLV cannot produce cDNA over 3 kb even after 60 minute RT reaction time. Mut D9 is therefore more active than wild type M-MLV at a wider range of pH, producing more cDNA and longer cDNA at both pH 8.3 and pH 7.3, even while at a higher temperature than wild type M-MLV.

Example 3

Mutant Reverse Transcriptase Thermostability

Figure 4:
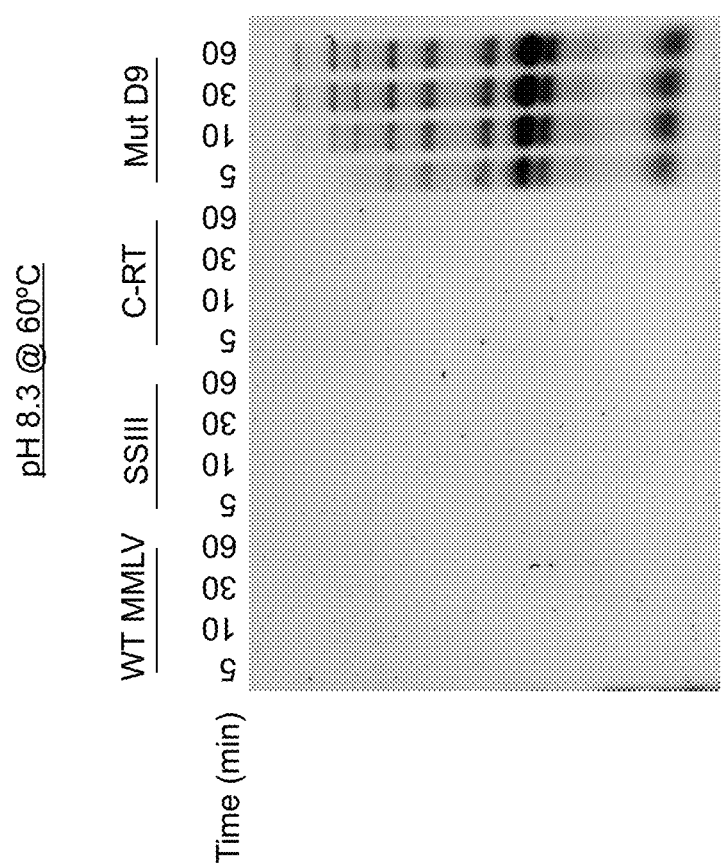
FIG. 4 is a fluorescent image showing RT activity of an exemplary mutant M-MLV reverse transcriptase as disclosed herein ("Mut D9"; SEQ ID NO:4) compared to wild type M-MLV reverse transcriptase ("WT MMLV"; SEQ ID NO:2) as well as other commercially available ("conventional") mutant M-MLV reverse transcriptases ("SSIII" and "C-RT"). Each lane shows the cDNA products obtained from RT reactions carried out for varying lengths of time (i.e., 5 minutes, 10 minutes, 30 minutes or 60 minutes) at 60° C. and at pH 8.3. A 0.5 to 10 kb RNA ladder was used as the template nucleic acid for each reaction.

The experiment described in Example 2 was also performed at 60° C. for varying lengths of time (i.e., 5 minutes, 10 minutes, 30 minutes or 60 minutes, as indicated in FIG. 4) to evaluate thermostability of an exemplary mutant RT as described herein ("Mut D9") compared to wild type M-MLV ("WT MMLV") and other commercially available RTs ("SSIII" and "C-RT"). At this temperature, a standard oligo (dT)$_{20}$ (SEQ ID NO: 5) cannot anneal to the polyadenylated tail of the RNA targets because the melting temperature is around 50° C. Instead an LNA™ oligo-T20 (SEQ ID NO: 13) (Exiqon Life Sciences) containing 50% LNA was utilized. Another difference in the experiment is that reaction mix containing buffer, RNA targets, and primer were first heated to 60° C. prior to the addition of RT enzyme ("manual hot start"). Manual hot start was performed to eliminate cDNA synthesis during reaction set up and temperature ramp up time. At pH 8.3 and 60° C., all enzymes except Mut D9 are non-functional. Mut D9 speed, cDNA yield, and cDNA length performance remains unchanged at 60° C. (see FIG. 4) compared to 50° C. (compare to FIG. 3). Thus, Mut D9 is both thermostable and thermoreactive—it can refold into an active enzyme after being heated to a higher temperature (thermostable) as well as synthesize cDNA at higher temperatures (thermoreactive) (see, e.g., FIG. 4).

Example 4

Evaluation of Reverse Transcription Sensitivity and Thermostability

Figure 5:
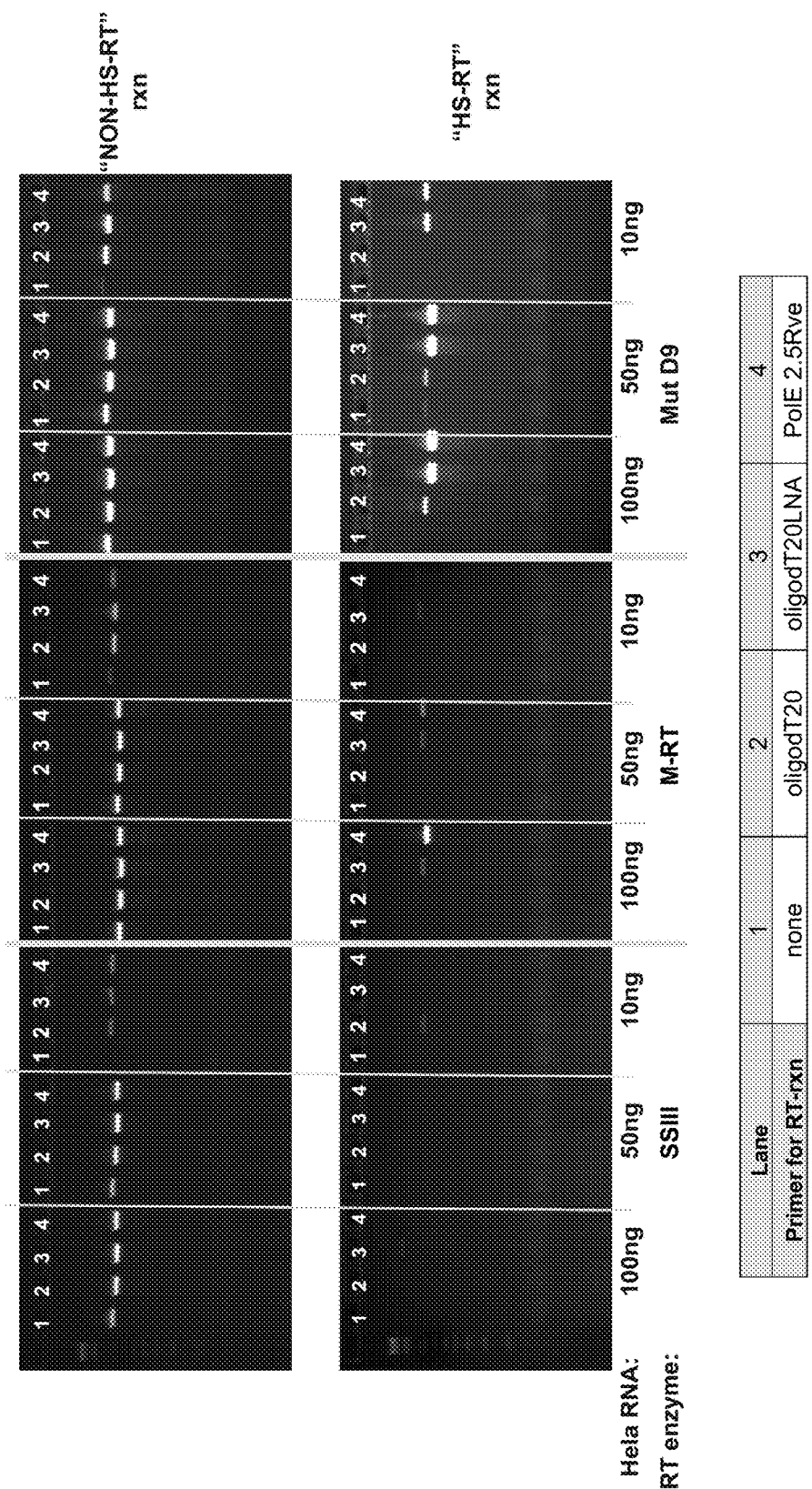
FIG. 5 is a photograph of an ethidium bromide stained gel showing RT activity of an exemplary mutant M-MLV reverse transcriptase as disclosed herein ("Mut D9"; SEQ ID NO:4) compared to other commercially available mutant M-MLV reverse transcriptases ("SSIII" and "M-RT"). Each lane shows the products (amplified via PCR) obtained from RT reactions carried out using different primers: (1) no primer; (2) oligo(dT)$_{20}$ primer (SEQ ID NO: 5); (3) oligo (dT)$_{20}$LNA primer (SEQ ID NO: 13); or (4) PolE 2.5Rve gene-specific primer and under varying reaction conditions (i.e., "NON-HS-RT-rxn" or "HS-RT-rxn"; HS=hot start), as indicated and as described in more detail in Example 4. A different amount (i.e., 10 ng, 50 ng, or 100 ng) of a 1 kb target ("Hela RNA") was used as the template nucleic acid for each reaction.

For all reactions, 100, 50 or 10 ng per 20 µL reaction of Hela RNA (Life Technologies, Cat. No. AM7852, Cervical Adenocarcinoma (Hela-S3) Total RNA) was incubated at the temperatures and times indicated below in: (1) the absence of primer, (2) in the presence of oligo(dT)$_{20}$ primer (SEQ ID NO: 5; (3) in the presence of LNA T20 primer (SEQ ID NO: 13) (Exiqon); and (4) in the presence of a gene specific primer (PolE 2.5 kb-rev primer sequence: GACCA-GGTCCTGCAGGGTGAAGGC (SEQ ID NO: 12)). Each reaction mixture contained the indicated amount of Hela RNA (as indicated in FIG. 5), 1 mM of each dNTP (dATP, dTTP, dGTP and dCTP) (Life Technologies, Cat. No. 10297018), 5 mM DTT (Life Technologies, Cat. No. Y00147), 1× First strand buffer (Life Technologies, Cat. No. Y02321), 1 µM primer (1, 2, 3, or 4, as described above and indicated in FIG. 5), 40 U RNaseOut (Life Technologies, Cat. No. 10777019) and 100 U of other commercially available mutant M-MLV reverse transcriptase ("SSIII" and "M-RT"), or an exemplary mutant M-MLV reverse transcriptase as disclosed herein ("Mut D9").

For non-hot start ("NON-HS-RT") reaction conditions, reaction mixtures minus proteins (reverse transcriptase and RNaseOut) were incubated at 65° C. for 5 minutes, followed by a 10 minute incubation on ice. RNaseOut and reverse transcriptase enzyme were added to each reaction, and the reactions were then incubated at room temperature for 10 minutes. This was followed by an additional incubation at 50° C. for 50 minutes, and then all reactions were heat killed at 95° C. for 10 minutes.

For manual hot start ("HS-RT") reaction conditions, reaction mixtures minus proteins (reverse transcriptase and RNaseOut) were incubated at 65° C. for 5 minutes, followed by 10 minute incubation on ice. RNaseOut was added to each reaction, and the reactions were incubated at 60° C. for 10 minutes in the absence of reverse transcriptase. Reverse transcriptase enzymes were then added directly to the reactions while incubating at 60° C. and the reactions were allowed to proceed at 60° C. for 50 minutes. All reactions were then heat killed at 95° C. for 10 minutes.

Using the cDNA products from the above-mentioned reverse transcription reactions, PCR mixtures were prepared. Briefly, 1 µL of the above RT reactions was added to 24 µL of a PCR mixture. PCR reactions were set up as recommended by the manufacturer using Platinum Taq DNA Polymerase High Fidelity (Life Technologies, Cat. No. 11304102) and amplified for 30 cycles. Gene-specific primers for the pol E gene were used for PCR and resulted in a 1 kb fragment. Primer sequences were as follows: Forward (AGCGCCAGACATCGAGGGCGTATATGAGAC (SEQ ID NO: 14)) and Reverse (TGGTGAGACTGGAGAATG-GTGTTG (SEQ ID NO: 15)). Gel products were visualized using 10 µL of each PCR reaction on a 2% E-gel (Life Technologies, Cat. No. G501802)

As FIG. 5 demonstrates, all three reverse transcriptases produced transcripts using 10-100 ng template DNA when incubated at room temperature and 50° C. (see "NON-HS-RT" reactions), even in the absence of any primer (1), and produced similar amounts of 1 kb cDNA using either (2) oligo(dT)$_{20}$ primer (SEQ ID NO: 5); (3) locked nucleic acid (LNA) T20 primer (SEQ ID NO: 13), and (4) gene specific primer with 50-100 ng template DNA. For the "HS-RT" reactions, the 1 kb cDNA was not produced by SSIII for 10, 50, or 100 ng template DNA in the absence of primer or with the addition of any of the primers (2, 3, or 4). The other commercially available RT ("M-RT") also did not produce any cDNA in the absence of primer and only produced trace amounts of cDNA for 10, 50, or 100 ng template DNA when either the LNA T20 primer (SEQ ID NO: 13) or the gene specific primers were used. Mutant M-MLV Mut D9 (SEQ ID NO:4) on the other hand produced significant amounts of cDNA for 10 ng template DNA when either the LNA T20 primer (SEQ ID NO: 13) or the gene specific primers were used and also produced significant amounts of cDNA for 50 and 100 ng of template DNA for all three of the primers (2, 3, and 4) that were tested. This shows that Mut D9 not only functions at 60° C., but is also able to reverse transcribe template DNA using non-specific (e.g., dT or LNA) primers as well as specific primers types. Mut D9's ability to produce more products with only 10 ng input RNA than either wild type M-MLV reverse transcriptase or any of the other commercially available ("conventional") mutant M-MLV RTs further indicates an increase in sensitivity.

Moreover, the ability to carry out reverse transcription reactions at higher temperatures, such as at 60° C., helps to prevent primerless cDNA synthesis which was visible for all RTs tested in the "NON-HS-RT" reactions. Thus, having an RT that is able to perform efficiently at 60° C., such as those disclosed herein, provides the benefit of reducing the amount of non-specific priming due to self-priming events that can often occur during RT reactions. This reduction in primerless cDNA is greatly enhanced at elevated temperatures (e.g., at 50° C., 55° C., 60° C., etc.).

Example 5

Mutant Reverse Transcriptase Performance in the Presence of Inhibitors

Figure 6:
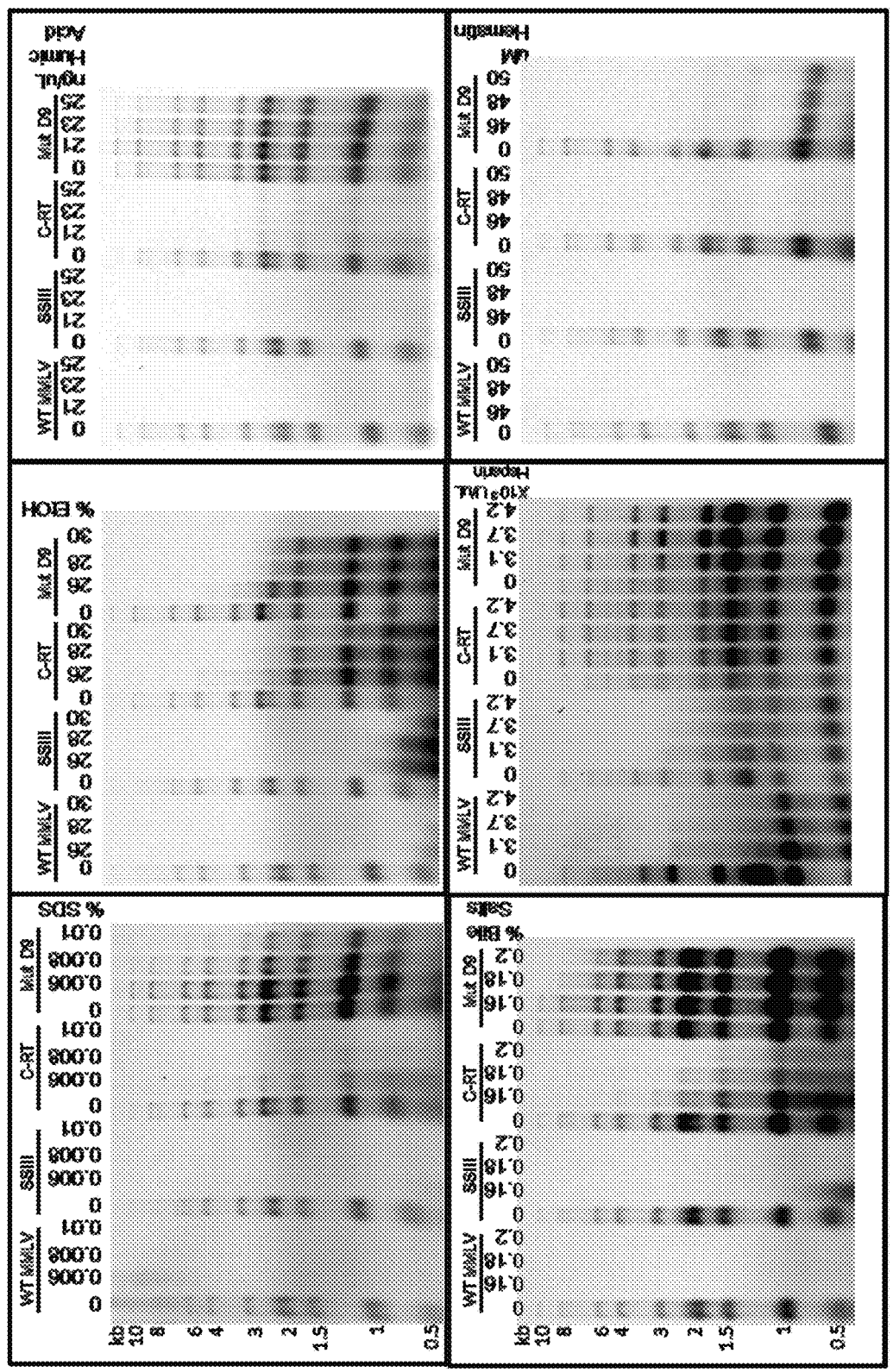
FIG. 6 is a fluorescent image showing RT activity of an exemplary mutant reverse transcriptase as disclosed herein ("Mut D9"; SEQ ID NO:4) compared to wild type M-MLV reverse transcriptase ("WT MMLV"; SEQ ID NO:2) as well as other commercially available ("conventional") mutant M-MLV reverse transcriptases ("SSIII" and "C-RT"). Each lane shows the cDNA products obtained from RT reactions carried out for 60 minutes at 50° C. and in the presence of various inhibitors at various concentrations, as indicated. A 0.5 to 10 kb RNA ladder was used as the template nucleic acid for each reaction.

A similar assay as that described in Example 2 was performed in the presence of various inhibitors. RT reaction temperature was 37° C. for wild type M-MLV, while the reaction temperature for other commercially available mutant M-MLV RTs ("SSIII" and "C-RT"), and Mut D9 was 50° C. Each RT reaction was carried out for 60 minutes. The RT inhibitors tested include SDS (0.006-0.01%), ethanol (26-30%), humic acid (21-25 ng/µL), bile salts (0.16-0.2%), heparin (0.0031-0.0042 U/µl), and hematin (46-50 µM). As FIG. 6 demonstrates, wild type M-MLV is not functional at all concentration of SDS, humic acid, bile salts, and hematin. It is slightly function in ethanol but cannot synthesize a full length 0.5 kb cDNA. However, in the presence of heparin, wild type M-MLV is able to synthesize the 0.5 kb cDNA. SSIII is not functional at all concentration of SDS, humic acid, and hematin. It is slightly functional in ethanol and bile salts but cannot synthesize a full length 0.5 kb cDNA. It can reverse transcribe up to 1.5 kb when heparin is present. Mut D9 shows greater activity than both wild type M-MLV and SSIII at all concentrations of inhibitors tested. Mut D9 compared to other commercially available RTs (i.e., C-RT) displays greater activity at all concentrations of inhibitors tested with the exception of ethanol and heparin where activity is approximately equal.

Figure 7:
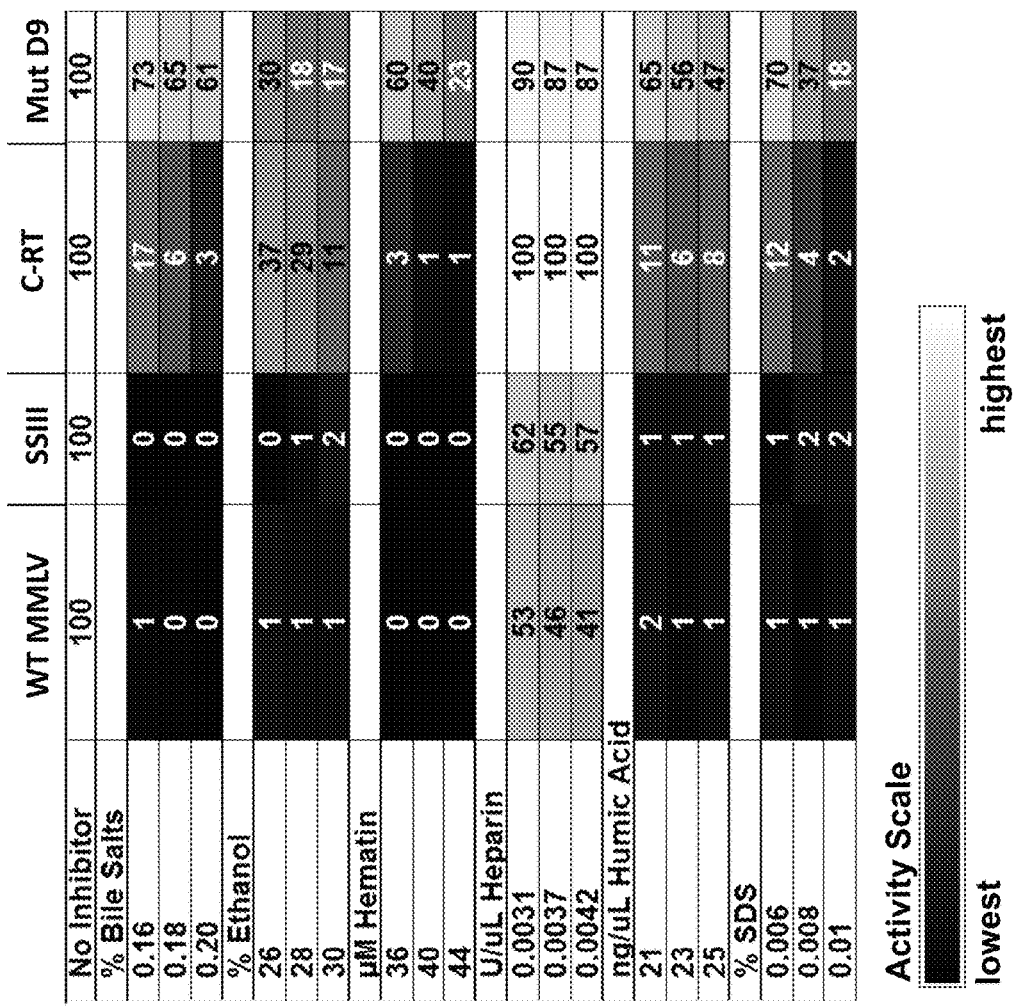
FIG. 7 illustrates the RT activity in graphical format of the different RTs in the presence of inhibitors, as shown in FIG. 6. RT activity was normalized to reactions comprising no inhibitor (indicated as 100% activity). Dark shading represents the lowest RT activity, while light shading represents the highest RT activity (Black to White=Lowest to Highest Activity).

The % activity of the RTs tested in the presence of the various inhibitors as described above was quantitated by densitometry using TotalLab TL100 software. Volume intensity of each band was summed in each lane. The volume intensity of no inhibitor lanes was set to 100% and lanes with inhibitors were normalized as % of no inhibitors to giv% activity. FIG. 7 shows the comparison of RT activities of the different RTs shown in FIG. 6. e

The invention claimed is:

1. An isolated mutant M-MLV reverse transcriptase, comprising a mutation at an amino acid position corresponding to S67 of wild type M-MLV reverse transcriptase (SEQ ID NO:2).

2. The mutant M-MLV reverse transcriptase of claim 1, wherein said mutation is selected from the group consisting of: S67R, S67N, and S67K.

3. The mutant M-MLV reverse transcriptase of claim 1, wherein said mutant reverse transcriptase further comprises at least one mutation at an amino acid position selected from the group consisting of: P51, E69, P196, T197, D200, H204, M289, E302, T306, F309, W313, T330, L435, N454, D524, E562, D583, H594, L603, D653, and L671 of wild type M-MLV reverse transcriptase (SEQ ID NO:2).

4. The mutant M-MLV reverse transcriptase of claim 3, comprising at least one mutation selected from the group consisting of: P51L, E69K, P196S, T197A, T197S, T197G, D200N, H204R, M289L, E302K, E302R, E302G, T306K, F309N, F309Y, F309I, W313F, W313L, W313C, T330P, L435G, L435V, L435R, N454K, D524G, E562Q, D583N, H594Q, L603W, D653N, D653H and L671P.

5. The mutant M-MLV reverse transcriptase of claim 3, comprising the following mutations: P51L, S67R, E69K, T197A, H204R, E302K, F309N, W313F, T330P, L435G, N454K, D524G, D583N, H594Q, D653N, and L671P.

6. The mutant M-MLV reverse transcriptase of claim 1, wherein said mutant reverse transcriptase lacks RNase H activity.

7. The mutant M-MLV reverse transcriptase of claim 1, wherein said mutant reverse transcriptase possesses one or more of the following properties when compared to the reverse transcriptase of SEQ ID NO:2:
   a. increased thermostability;
   b. increased thermoreactivity;
   c. increased resistance to reverse transcriptase inhibitors;
   d. increased ability to reverse transcribe difficult templates
   e. increased speed;
   f. increased processivity;
   g. increased specificity; or
   h. increased sensitivity.

8. The mutant M-MLV reverse transcriptase of claim 1, wherein said mutant reverse transcriptase synthesizes at least 50% more reverse transcriptase product within 5 minutes at 60° C. than the amount of reverse transcriptase product synthesized by wild type M-MLV after 5 minutes at 37° C.

9. The mutant M-MLV reverse transcriptase of claim 1, wherein said mutant reverse transcriptase demonstrates increased reverse transcriptase activity at a reaction temperature of 60° C. compared to reverse transcriptase activity of said wild type M-MLV reverse transcriptase.

10. An isolated mutant M-MLV reverse transcriptase, comprising at least ten mutations at an amino acid position selected from the group consisting of P51, E69, P196, D200, H204, M289, T306, F309, W313, T330, L435, N454, D524, E562, D583, H594, L603, D653, and L671 of wild type M-MLV (SEQ ID NO:2).

11. The mutant M-MLV reverse transcriptase of claim 10, comprising at least ten mutations selected from the group consisting of P51L, E69K, P196S, D200N, H204R, M289L, T306K, F309N, F309Y, F309I, W313F, W313L, W313C, T330P, L435G, L435V, L435R, N454K, D524G, E562Q, D583N, H594Q, L603W, D653N, D653H and L671P.

12. The mutant M-MLV reverse transcriptase of claim 10, wherein said mutant reverse transcriptase further comprises at least one mutation at an amino acid position selected from the group consisting of S67, T197, and E302 of wild type M-MLV (SEQ ID NO:2).

13. The mutant M-MLV reverse transcriptase of claim 12, wherein said reverse transcriptase comprises at least one mutation selected from the group consisting of S67R, S67N, S67K, T197A, T197S, T197G, E302K, E302R, and E302G.

14. The mutant M-MLV reverse transcriptase of claim 10, wherein said mutant reverse transcriptase lacks RNase H activity.

15. The mutant M-MLV reverse transcriptase of claim 10, wherein said mutant reverse transcriptase possesses one or more of the following properties when compared to the reverse transcriptase of SEQ ID NO:2:
   a. increased thermostability;
   b. increased thermoreactivity;
   c. increased resistance to reverse transcriptase inhibitors;
   d. increased ability to reverse transcribe difficult templates
   e. increased speed;
   f. increased processivity;
   g. increased specificity; and
   h. increased sensitivity.

16. The mutant M-MLV reverse transcriptase of claim 10, wherein said mutant reverse transcriptase synthesizes at least 50% more reverse transcriptase product within 5 minutes at 60° C. than the amount of reverse transcriptase product synthesized by wild type M-MLV after 5 minutes at 37° C.

17. The mutant M-MLV reverse transcriptase of claim 10, wherein said mutant reverse transcriptase demonstrates increased reverse transcriptase activity at a reaction temperature of 60° C. compared to reverse transcriptase activity of said wild type M-MLV reverse transcriptase.

18. An isolated mutant reverse transcriptase, wherein said mutant reverse transcriptase comprises at least 99% amino acid sequence identity to SEQ ID NO:4.

19. The mutant reverse transcriptase of claim 18, wherein said mutant reverse transcriptase is thermostable at 60° C.

20. A composition for nucleic acid synthesis, comprising a mutant M-MLV reverse transcriptase and a buffer, wherein said mutant reverse transcriptase comprises at least 99% amino acid sequence identity to SEQ ID NO:4.

* * * * *

SEQUENCE LISTING

<160> NUMBER OF SEQ ID NOS: 20

<210> SEQ ID NO 1
<211> LENGTH: 2031
<212> TYPE: DNA
<213> ORGANISM: Maloney murine leukemia virus

<400> SEQUENCE: 1

```
accctaaata tagaagatga gcatcggcta catgagacct caaaagagcc agatgtttct      60
ctagggtcca catggctgtc tgattttcct caggcctggg cggaaaccgg gggcatggga     120
ctggcagttc gccaagctcc tctgatcata cctctgaaag caacctctac ccccgtgtcc     180
ataaaacaat accccatgtc acaagaagcc agactgggga tcaagcccca catacagaga     240
ctgttggacc agggaatact ggtaccctgc cagtccccct ggaacacgcc cctgctaccc     300
gttaagaaac cagggactaa tgattatagg cctgtccagg atctgagaga agtcaacaag     360
cgggtggaag acatccaccc caccgtgccc aaccctaca acctcttgag cgggctccca     420
ccgtcccacc agtggtacac tgtgcttgat ttaaaggatg ccttttctg cctgagactc     480
cacccccacca gtcagcctct cttcgccttt gagtggagag atccagagat gggaatctca     540
ggacaattga cctggaccag actcccacag ggtttcaaaa acagtcccac cctgtttgat     600
gaggcactgc acagagacct agcagacttc cggatccagc acccagactt gatcctgcta     660
cagtacgtgg atgacttact gctggccgcc acttctgagc tagactgcca acaaggtact     720
cgggccctgt tacaaaccct agggaacctc gggtatcggg cctcggccaa gaaagcccaa     780
atttgccaga aacaggtcaa gtatctgggg tatcttctaa aagagggtca gagatggctg     840
actgaggcca gaaagagac tgtgatgggg cagcctactc cgaagaccce tcgacaacta     900
agggagttcc tagggacggc aggcttctgt cgcctctgga tccctgggtt tgcagaaatg     960
gcagcccct tgtaccctct caccaaaacg gggactctgt ttaattgggg cccagaccaa    1020
caaaaggcct atcaagaaat caagcaagct cttctaactg ccccagccct ggggttgcca    1080
gattttgacta gcccctttga actctttgtc gacgagaagc agggctacgc caaaggtgtc    1140
ctaacgcaaa aactggggacc ttggcgtcgg ccggtggcct acctgtccaa aaagctagac    1200
ccagtagcag ctgggtggcc cccttgccta cggatggtag cagccattgc cgtactgaca    1260
aaggatgcag gcaagctaac catgggacag ccactagtca ttctggcccc ccatgcagta    1320
gaggcactag tcaaacaacc ccccgaccgc tggcttttca acgcccggat gactcactat    1380
caggccttgc tttggacac ggaccgggtc cagttcggac cggtggtagc cctgaacccg    1440
gctacgctgc tcccactgcc tgaggaaggg ctgcaacaca actgccttga tatcctggcc    1500
gaagcccacg gaacccgacc cgacctaacg gaccagccgc tcccagacgc cgaccacacc    1560
tggtacacgg atggaagcag tctcttacaa gagggacagc gtaaggcggg agctgcggtg    1620
accaccgaga ccgaggtaat ctgggctaaa gccctgccag ccgggacatc cgctcagcgg    1680
gctgaactga tagcactcac ccaggcccta aagatggcag aaggtaagaa gctaaatgtt    1740
tatactgata gccgttatgc ttttgctact gcccatatcc atggagaaat atacagaagg    1800
cgtgggttgc tcacatcaga aggcaaagag atcaaaaata agacgagat cttggcccta    1860
ctaaaagccc tctttctgcc caaaagactt agcataatcc attgtccagg acatcaaaag    1920
ggacacagcg ccgaggctag aggcaaccgg atggctgacc aagcggcccg aaaggcagcc    1980
atcacagaga ctccagacac ctctaccctc tcatagaaa attcatcacc c              2031
```

```
<210> SEQ ID NO 2
<211> LENGTH: 677
<212> TYPE: PRT
<213> ORGANISM: Maloney murine leukemia virus

<400> SEQUENCE: 2

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
50                  55                  60

Pro Met Ser Gln Glu Ala Arg Leu Gly Ile Lys Pro His Ile Gln Arg
65                  70                  75                  80

Leu Leu Asp Gln Gly Ile Leu Val Pro Cys Gln Ser Pro Trp Asn Thr
                85                  90                  95

Pro Leu Leu Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Glu Ala Arg Lys Glu Thr Val
        275                 280                 285

Met Gly Gln Pro Thr Pro Lys Thr Pro Arg Gln Leu Arg Glu Phe Leu
290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
370                 375                 380
```

-continued

```
Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
            405                 410                 415

Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Leu Leu
450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Asp Gly Ser Ser Leu
        515                 520                 525

Leu Gln Glu Gly Gln Arg Lys Ala Gly Ala Ala Val Thr Thr Glu Thr
530                 535                 540

Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
                565                 570                 575

Lys Leu Asn Val Tyr Thr Asp Ser Arg Tyr Ala Phe Ala Thr Ala His
            580                 585                 590

Ile His Gly Glu Ile Tyr Arg Arg Gly Leu Leu Thr Ser Glu Gly
        595                 600                 605

Lys Glu Ile Lys Asn Lys Asp Glu Ile Leu Ala Leu Leu Lys Ala Leu
610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu Ile
            660                 665                 670

Glu Asn Ser Ser Pro
            675
```

<210> SEQ ID NO 3
<211> LENGTH: 2031
<212> TYPE: DNA
<213> ORGANISM: Maloney murine leukemia virus

<400> SEQUENCE: 3

```
accctgaaca tcgaagatga atatcgtctg catgaaacca gcaaagaacc ggatgttagc      60
ctgggtagca cctggctgag cgattttccg caggcatggg cagaaaccgg tggtatgggt    120
ctggcagttc gtcaggcacc gctgattatt ctgctgaaag caaccagcac accggttagc    180
attaaacagt atccgatgag cagaaagcc cgtctgggta ttaaaccgca tattcagcgt     240
ctgctggatc agggtattct ggttccgtgt cagagcccgt ggaatacacc gctgctgccg    300
gttaaaaaac cgggtacaaa tgattatcgt ccggttcagg atctgcgtga agttaataaa    360
cgcgtggaag atattcatcc gaccgttccg aatccgtata atctgctgag cggtctgcct    420
```

-continued

| | |
|---|---|
| ccgagccatc agtggtatac cgttctggat ctgaaagatg cctttttttg tctgcgtctg | 480 |
| catccgacca gccagccgct gtttgcattt gaatggcgtg atccggaaat gggtattagc | 540 |
| ggtcaactga cctggacccg tctgccgcag ggttttaaaa atagcccggc cctgtttgat | 600 |
| gaggccctgc gtcgtgatct ggcagatttt cgtattcagc atccggatct gattctgctg | 660 |
| cagtatgttg atgatctgct gctggcagca accagcgaac tggattgtca gcagggcacc | 720 |
| cgtgcactgc tgcagacccT gggtgatctg gttatcgtg caagcgcaaa aaaagcacag | 780 |
| atttgtcaga acaggtgaa atatctgggc tatctgctga agaaggtca gcgttggctg | 840 |
| accgaagcac gtaaagaaac cgttatgggt cagccgaccc cgaaaacacc gcgtcagctg | 900 |
| cgtaaatttc tgggtacagc aggtaattgc cgtctgttca ttccgggttt tgcagaaatg | 960 |
| gcagcaccgc tgtatccgct gaccaaaccc ggcacccTgt taattgggg tccggatcag | 1020 |
| cagaaagcct atcaagaaat taaacaggca ctgctgaccg caccggcact gggtctgcct | 1080 |
| gacctgacca aaccgtttga actgtttgtg gatgaaaaac aggttatgc aaaaggtgtt | 1140 |
| ctgacccaga aactgggtcc gtggcgtcgt ccggttgcat atctgagcaa aaaactggat | 1200 |
| ccggttgcag caggttggcc tccgtgtctg cgtatggttg cagcaattgc agttctgacc | 1260 |
| aaagatgcag gtaaactgac aatgggtcag ccgctggtta ttggggcacc gcatgcagtt | 1320 |
| gaagcactgg ttaaacagcc tccggatcgt tggctgagca aggcccgtat gacccattat | 1380 |
| caggccctgc tgctggatac cgatcgtgtt cagtttggtc cggttgttgc actgaatccg | 1440 |
| gcaaccctgc tgccgctgcc ggaagaaggt ctgcagcata attgtctgga tattctggcc | 1500 |
| gaagcacatg gcacccgtcc ggatctgaca gatcagccgc tgcctgatgc agatcatacc | 1560 |
| tggtataccg gcggtagcag cctgctgcaa gagggccagc gtaaagccgg tgcagcagtt | 1620 |
| accaccgaaa ccgaagttat ttgggcaaaa gcactgcctg ctggcaccag cgcacagcgt | 1680 |
| gcagagctga ttgcactgac ccaggcactg cgtatggccg aaggtaaaaa actgaatgtg | 1740 |
| tataccaaca gccgctatgc atttgcaacc gcacatattc agggcgaaat ttatcgtcgt | 1800 |
| cgtggtttgc tgaccagcga aggtaaagaa attaaaaata agatgaaat tctggccctg | 1860 |
| ctgaaagcac tgtttctgcc gaaacgtctg agcattattc attgtccggg tcatcagaaa | 1920 |
| ggtcatagcg cagaagcacg cggtaatcgt atggcaaacc aggcagcacg taaagcagca | 1980 |
| attaccgaaa atccggatac cagcaccctg ccgattgaaa atagcagccc g | 2031 |

<210> SEQ ID NO 4
<211> LENGTH: 677
<212> TYPE: PRT
<213> ORGANISM: Maloney murine leukemia virus

<400> SEQUENCE: 4

Thr Leu Asn Ile Glu Asp Glu Tyr Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Leu Leu Lys Ala Thr Ser Thr Pro Val Ser Ile Lys Gln Tyr
    50                  55                  60

Pro Met Arg Gln Lys Ala Arg Leu Gly Ile Lys Pro His Ile Gln Arg
65                  70                  75                  80

Leu Leu Asp Gln Gly Ile Leu Val Pro Cys Gln Ser Pro Trp Asn Thr
                85                  90                  95

```
Pro Leu Leu Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Ala Leu Phe Asp Glu Ala Leu Arg Arg Asp Leu Ala
        195                 200                 205

Asp Phe Arg Ile Gln His Pro Asp Leu Ile Leu Leu Gln Tyr Val Asp
210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asp Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Glu Ala Arg Lys Glu Thr Val
        275                 280                 285

Met Gly Gln Pro Thr Pro Lys Thr Pro Arg Gln Leu Arg Lys Phe Leu
290                 295                 300

Gly Thr Ala Gly Asn Cys Arg Leu Phe Ile Pro Gly Phe Ala Glu Met
305                 310                 315                 320

Ala Ala Pro Leu Tyr Pro Leu Thr Lys Pro Gly Thr Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Val Ile Gly Ala Pro His Ala Val Glu Ala Leu Val Lys Gln Pro Pro
        435                 440                 445

Asp Arg Trp Leu Ser Lys Ala Arg Met Thr His Tyr Gln Ala Leu Leu
450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510
```

-continued

```
Pro Leu Pro Asp Ala Asp His Thr Trp Tyr Thr Gly Ser Ser Leu
            515                 520                 525

Leu Gln Glu Gly Gln Arg Lys Ala Gly Ala Ala Val Thr Thr Glu Thr
530                 535                 540

Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Arg Met Ala Glu Gly Lys
                565                 570                 575

Lys Leu Asn Val Tyr Thr Asn Ser Arg Tyr Ala Phe Ala Thr Ala His
            580                 585                 590

Ile Gln Gly Glu Ile Tyr Arg Arg Gly Leu Leu Thr Ser Glu Gly
        595                 600                 605

Lys Glu Ile Lys Asn Lys Asp Glu Ile Leu Ala Leu Leu Lys Ala Leu
    610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asn Gln Ala Ala
                645                 650                 655

Arg Lys Ala Ala Ile Thr Glu Asn Pro Asp Thr Ser Thr Leu Pro Ile
            660                 665                 670

Glu Asn Ser Ser Pro
        675

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tttttttttt tttttttttt                                              20

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 6

His His His His His His
1               5

<210> SEQ ID NO 7
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Gly Gly Ser His His His His His Gly Met Ala Ser Met Thr
1               5                  10                  15

Gly Gly Gln Gln Met Gly Arg Asp Leu Tyr Asp Asp Asp Lys His
                20                  25                  30

<210> SEQ ID NO 8
```

```
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Met Ala Ser Gly Thr Gly Gly Gln Gln Met Gly Arg Asp Leu Tyr Asp
1               5                   10                  15

Asp Asp Asp Lys His
            20

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: misc_feature
<222> LOCATION: (1)..(7)
<223> OTHER INFORMATION: This sequence may encompass 3 to 7 residues

<400> SEQUENCE: 9

His His His His His His His
1               5

<210> SEQ ID NO 10
<211> LENGTH: 4
<212> TYPE: PRT
<213> ORGANISM: Unknown
<220> FEATURE:
<223> OTHER INFORMATION: Description of Unknown: Factor Xa cleavage site
      peptide

<400> SEQUENCE: 10

Ile Glu Gly Arg
1

<210> SEQ ID NO 11
<211> LENGTH: 4
<212> TYPE: PRT
<213> ORGANISM: Unknown
<220> FEATURE:
<223> OTHER INFORMATION: Description of Unknown: Thrombin cleavage site
      peptide

<400> SEQUENCE: 11

Leu Val Pro Arg
1

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gaccaggtcc tgcagggtga aggc                                          24

<210> SEQ ID NO 13
<211> LENGTH: 20
<212> TYPE: DNA
<213> ORGANISM: Artificial Sequence
```

-continued

```
<220> FEATURE:
<223> OTHER INFORMATION: Description of Artificial Sequence: Synthetic
      primer
<220> FEATURE:
<221> NAME/KEY: modified_base
<222> LOCATION: (1)..(20)
<223> OTHER INFORMATION: Locked nucleic acid

<400> SEQUENCE: 13
tttttttttt tttttttttt                                                      20

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
agcgccagac atcgagggcg tatatgagac                                           30

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tggtgagact ggagaatggt gttg                                                 24

<210> SEQ ID NO 16
<211> LENGTH: 677
<212> TYPE: PRT
<213> ORGANISM: Maloney murine leukemia virus

<400> SEQUENCE: 16

Thr Leu Asn Ile Glu Asp Glu Tyr Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Gln Glu Ala Arg Leu Gly Ile Lys Pro His Ile Gln Arg
65                  70                  75                  80

Leu Leu Asp Gln Gly Ile Leu Val Pro Cys Gln Ser Pro Trp Asn Thr
                85                  90                  95

Pro Leu Leu Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175
```

```
Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asp Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Glu Ala Arg Lys Glu Thr Val
        275                 280                 285

Met Gly Gln Pro Thr Pro Lys Thr Pro Arg Gln Leu Arg Glu Phe Leu
    290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asp Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
    370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Leu Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Asp Gly Ser Ser Phe
        515                 520                 525

Leu Gln Glu Gly Gln Arg Lys Ala Gly Ala Ala Val Thr Thr Glu Thr
    530                 535                 540

Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
                565                 570                 575

Lys Leu Asn Val Tyr Thr Asp Ser Arg Tyr Ala Phe Ala Thr Ala His
            580                 585                 590

Ile His Gly Glu Ile Tyr Arg Arg Arg Gly Leu Leu Thr Ser Glu Gly
```

```
                595                 600                 605
Lys Glu Ile Lys Asn Lys Gly Glu Ile Leu Ala Leu Leu Lys Ala Leu
            610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
            645                 650                 655

Arg Lys Ala Ala Ile Thr Glu Thr Pro Asp Thr Ser Thr Leu Leu Ile
            660                 665                 670

Glu Lys Ser Ser Pro
        675

<210> SEQ ID NO 17
<211> LENGTH: 678
<212> TYPE: PRT
<213> ORGANISM: Baboon endogenous virus

<400> SEQUENCE: 17

Met Thr Val Ser Leu Gln Asp Glu His Arg Leu Phe Asp Ile Pro Val
1               5                   10                  15

Thr Thr Ser Leu Pro Asp Val Trp Leu Gln Asp Phe Pro Gln Ala Trp
            20                  25                  30

Ala Glu Thr Gly Gly Leu Gly Arg Ala Lys Cys Gln Ala Pro Ile Ile
        35                  40                  45

Ile Asp Leu Lys Pro Thr Ala Val Pro Val Ser Ile Lys Gln Tyr Pro
    50                  55                  60

Met Ser Leu Glu Ala His Met Gly Ile Arg Gln His Ile Ile Lys Phe
65                  70                  75                  80

Leu Glu Leu Gly Val Leu Arg Pro Cys Arg Ser Pro Trp Asn Thr Pro
                85                  90                  95

Leu Leu Pro Val Lys Lys Pro Gly Thr Gln Asp Tyr Arg Pro Val Gln
            100                 105                 110

Asp Leu Arg Glu Ile Asn Lys Arg Thr Val Asp Ile His Pro Thr Val
        115                 120                 125

Pro Asn Pro Tyr Asn Leu Leu Ser Thr Leu Lys Pro Asp Tyr Ser Trp
    130                 135                 140

Tyr Thr Val Leu Asp Leu Lys Asp Ala Phe Phe Cys Leu Pro Leu Ala
145                 150                 155                 160

Pro Gln Ser Gln Glu Leu Phe Ala Phe Glu Trp Lys Asp Pro Glu Arg
                165                 170                 175

Gly Ile Ser Gly Gln Leu Thr Trp Thr Arg Leu Pro Gln Gly Phe Lys
            180                 185                 190

Asn Ser Pro Thr Leu Phe Asp Glu Ala Leu His Arg Asp Leu Thr Asp
        195                 200                 205

Phe Arg Thr Gln His Pro Glu Val Thr Leu Leu Gln Tyr Val Asp Asp
    210                 215                 220

Leu Leu Leu Ala Ala Pro Thr Lys Lys Ala Cys Thr Gln Gly Thr Arg
225                 230                 235                 240

His Leu Leu Gln Glu Leu Gly Glu Lys Gly Tyr Arg Ala Ser Ala Lys
                245                 250                 255

Lys Ala Gln Ile Cys Gln Thr Lys Val Thr Tyr Leu Gly Tyr Ile Leu
            260                 265                 270

Ser Glu Gly Lys Arg Trp Leu Thr Pro Gly Arg Ile Glu Thr Val Ala
        275                 280                 285
```

-continued

Arg Ile Pro Pro Pro Arg Asn Pro Arg Glu Val Arg Glu Phe Leu Gly
    290                 295                 300

Thr Ala Gly Phe Cys Arg Leu Trp Ile Pro Gly Phe Ala Glu Leu Ala
305                 310                 315                 320

Ala Pro Leu Tyr Ala Leu Thr Lys Glu Ser Thr Pro Phe Thr Trp Gln
            325                 330                 335

Thr Glu His Gln Leu Ala Phe Glu Ala Leu Lys Lys Ala Leu Leu Ser
        340                 345                 350

Ala Pro Ala Leu Gly Leu Pro Asp Thr Ser Lys Pro Phe Thr Leu Phe
    355                 360                 365

Leu Asp Glu Arg Gln Gly Ile Ala Lys Gly Val Leu Thr Gln Lys Leu
370                 375                 380

Gly Pro Trp Lys Arg Pro Val Ala Tyr Leu Ser Lys Lys Leu Asp Pro
385                 390                 395                 400

Val Ala Ala Gly Trp Pro Pro Cys Leu Arg Ile Met Ala Ala Thr Ala
            405                 410                 415

Met Leu Val Lys Asp Ser Ala Lys Leu Thr Leu Gly Gln Pro Leu Thr
        420                 425                 430

Val Ile Thr Pro His Thr Leu Glu Ala Ile Val Arg Gln Pro Pro Asp
    435                 440                 445

Arg Trp Ile Thr Asn Ala Arg Leu Thr His Tyr Gln Ala Leu Leu Leu
450                 455                 460

Asp Thr Asp Arg Val Gln Phe Gly Pro Pro Val Thr Leu Asn Pro Ala
465                 470                 475                 480

Thr Leu Leu Pro Val Pro Glu Asn Gln Pro Ser Pro His Asp Cys Arg
            485                 490                 495

Gln Val Leu Ala Glu Thr His Gly Thr Arg Glu Asp Leu Lys Asp Gln
        500                 505                 510

Glu Leu Pro Asp Ala Asp His Thr Trp Tyr Thr Asp Gly Ser Ser Tyr
    515                 520                 525

Leu Asp Ser Gly Thr Arg Arg Ala Gly Ala Ala Val Val Asp Gly His
530                 535                 540

Asn Thr Ile Trp Ala Gln Ser Leu Pro Pro Gly Thr Ser Ala Gln Lys
545                 550                 555                 560

Ala Glu Leu Ile Ala Leu Thr Lys Ala Leu Glu Leu Ser Lys Gly Lys
            565                 570                 575

Lys Ala Asn Ile Tyr Thr Asp Ser Arg Tyr Ala Phe Ala Thr Ala His
        580                 585                 590

Thr His Gly Ser Ile Tyr Glu Arg Arg Gly Leu Leu Thr Ser Glu Gly
    595                 600                 605

Lys Glu Ile Lys Asn Lys Ala Glu Ile Ile Ala Leu Leu Lys Ala Leu
610                 615                 620

Phe Leu Pro Gln Glu Val Ala Ile Ile His Cys Pro Gly His Gln Lys
625                 630                 635                 640

Gly Gln Asp Pro Val Ala Val Gly Asn Arg Gln Ala Asp Arg Val Ala
            645                 650                 655

Arg Gln Ala Ala Met Ala Glu Val Leu Thr Leu Ala Thr Glu Pro Asp
        660                 665                 670

Asn Thr Ser His Ile Thr
        675

<210> SEQ ID NO 18
<211> LENGTH: 674
<212> TYPE: PRT

<213> ORGANISM: Fowlpox virus

<400> SEQUENCE: 18

```
Met Thr Ala Pro Leu Glu Glu Glu Tyr Arg Leu Phe Leu Glu Ala Pro
1               5                   10                  15

Ile Gln Asn Val Thr Leu Leu Glu Gln Trp Lys Arg Glu Ile Pro Lys
            20                  25                  30

Val Trp Ala Glu Ile Asn Pro Pro Gly Leu Ala Ser Thr Gln Ala Pro
        35                  40                  45

Ile His Val Gln Leu Leu Ser Thr Ala Leu Pro Val Arg Val Arg Gln
    50                  55                  60

Tyr Pro Ile Thr Leu Glu Ala Lys Arg Ser Leu Arg Glu Thr Ile Arg
65                  70                  75                  80

Lys Phe Arg Ala Ala Gly Ile Leu Arg Pro Val His Ser Pro Trp Asn
                85                  90                  95

Thr Pro Leu Leu Pro Val Arg Lys Ser Gly Thr Ser Glu Tyr Arg Met
            100                 105                 110

Val Gln Asp Leu Arg Glu Val Asn Lys Arg Val Glu Thr Ile His Pro
        115                 120                 125

Thr Val Pro Asn Pro Tyr Thr Leu Leu Ser Leu Leu Pro Pro Asp Arg
    130                 135                 140

Ile Trp Tyr Ser Val Leu Asp Leu Lys Asp Ala Phe Phe Cys Ile Pro
145                 150                 155                 160

Leu Ala Pro Glu Ser Gln Leu Ile Phe Ala Phe Glu Trp Ala Asp Ala
                165                 170                 175

Glu Glu Gly Glu Ser Gly Gln Leu Thr Trp Thr Arg Leu Pro Gln Gly
            180                 185                 190

Phe Lys Asn Ser Pro Thr Leu Phe Asp Glu Ala Leu Asn Arg Asp Leu
        195                 200                 205

Gln Gly Phe Arg Leu Asp His Pro Phe Val Ser Leu Leu Gln Tyr Val
    210                 215                 220

Asp Asp Leu Leu Ile Ala Ala Asp Thr Gln Ala Ala Cys Leu Ser Ala
225                 230                 235                 240

Thr Arg Asp Leu Leu Met Thr Leu Ala Glu Leu Gly Tyr Arg Val Ser
                245                 250                 255

Gly Lys Lys Ala Gln Leu Cys Gln Glu Glu Val Thr Tyr Leu Gly Phe
            260                 265                 270

Lys Ile His Lys Gly Ser Arg Thr Leu Ser Asn Ser Arg Thr Gln Ala
        275                 280                 285

Ile Leu Gln Ile Pro Val Pro Lys Thr Lys Arg Gln Val Arg Glu Phe
    290                 295                 300

Leu Gly Thr Ile Gly Tyr Cys Arg Leu Trp Ile Pro Gly Phe Ala Glu
305                 310                 315                 320

Leu Ala Gln Pro Leu Tyr Ala Ala Thr Arg Gly Gly Asn Asp Pro Leu
                325                 330                 335

Val Trp Gly Glu Lys Glu Glu Glu Ala Phe Gln Ser Leu Lys Leu Ala
            340                 345                 350

Leu Thr Gln Pro Pro Ala Leu Ala Leu Pro Ser Leu Asp Lys Pro Phe
        355                 360                 365

Gln Leu Phe Val Glu Glu Thr Gly Gly Ala Ala Lys Gly Val Leu Thr
    370                 375                 380

Gln Ala Leu Gly Pro Trp Lys Arg Pro Val Ala Tyr Leu Ser Lys Arg
385                 390                 395                 400
```

Leu Asp Pro Val Ala Gly Trp Pro Arg Cys Leu Arg Ala Ile Ala
                405                 410                 415

Ala Ala Ala Leu Leu Thr Arg Glu Ala Ser Lys Leu Thr Phe Gly Gln
            420                 425                 430

Asp Ile Glu Ile Thr Ser Ser His Asn Leu Glu Ser Leu Leu Arg Ser
            435                 440                 445

Pro Pro Asp Arg Trp Leu Thr Asn Ala Arg Ile Thr Gln Tyr Gln Val
        450                 455                 460

Leu Leu Leu Asp Pro Pro Arg Val Arg Phe Lys Gln Thr Ala Ala Leu
465                 470                 475                 480

Asn Pro Ala Thr Leu Leu Pro Glu Thr Asp Asp Thr Leu Pro Ile His
                485                 490                 495

His Cys Leu Asp Thr Leu Asp Ser Leu Thr Ser Thr Arg Pro Asp Leu
            500                 505                 510

Thr Asp Gln Pro Leu Ala Gln Ala Glu Ala Thr Leu Phe Thr Asp Gly
        515                 520                 525

Ser Ser Tyr Ile Arg Asp Gly Lys Arg Tyr Thr Gly Ala Ala Val Val
        530                 535                 540

Thr Leu Asp Ser Val Ile Trp Ala Glu Pro Leu Pro Ile Gly Thr Ser
545                 550                 555                 560

Ala Gln Lys Ala Glu Leu Ile Ala Leu Thr Lys Ala Leu Glu Trp Ser
                565                 570                 575

Lys Asp Lys Ser Val Asn Ile Tyr Thr Asp Ser Arg Tyr Ala Phe Ala
            580                 585                 590

Thr Leu His Val His Gly Met Ile Tyr Arg Glu Arg Gly Leu Leu Thr
        595                 600                 605

Ala Gly Gly Lys Ala Ile Lys Asn Ala Pro Glu Ile Leu Ala Leu Leu
    610                 615                 620

Thr Ala Val Trp Leu Pro Lys Arg Val Ala Val Met His Cys Lys Gly
625                 630                 635                 640

His Gln Lys Asp Asp Ala Pro Thr Ser Thr Gly Asn Arg Arg Ala Asp
                645                 650                 655

Glu Val Ala Arg Glu Val Ala Ile Arg Pro Leu Ser Thr Gln Ala Thr
            660                 665                 670

Ile Ser

<210> SEQ ID NO 19
<211> LENGTH: 673
<212> TYPE: PRT
<213> ORGANISM: Phascolarctos cinereus

<400> SEQUENCE: 19

Met Val Leu Asn Leu Glu Glu Glu Tyr Arg Leu His Glu Lys Pro Val
1               5                   10                  15

Pro Pro Ser Ile Asp Pro Ser Trp Leu Gln Leu Phe Pro Met Val Trp
            20                  25                  30

Ala Glu Lys Ala Gly Met Gly Leu Ala Asn Gln Val Pro Pro Val Val
        35                  40                  45

Val Glu Leu Lys Ser Asp Ala Ser Pro Val Ala Val Arg Gln Tyr Pro
    50                  55                  60

Met Ser Lys Glu Ala Arg Glu Gly Ile Arg Pro His Ile Gln Arg Phe
65                  70                  75                  80

Leu Asp Leu Gly Ile Leu Val Pro Cys Gln Ser Pro Trp Asn Thr Pro
                85                  90                  95

```
Leu Leu Pro Val Lys Lys Pro Gly Thr Asn Asp Tyr Arg Pro Val Gln
            100                 105                 110

Asp Leu Arg Glu Val Asn Lys Arg Val Gln Asp Ile His Pro Thr Val
        115                 120                 125

Pro Asn Pro Tyr Asn Leu Leu Ser Ser Leu Pro Pro Ser His Thr Trp
    130                 135                 140

Tyr Ser Val Leu Asp Leu Lys Asp Ala Phe Phe Cys Leu Lys Leu His
145                 150                 155                 160

Pro Asn Ser Gln Pro Leu Phe Ala Phe Glu Trp Arg Asp Pro Glu Lys
                165                 170                 175

Gly Asn Thr Gly Gln Leu Thr Trp Thr Arg Leu Pro Gln Gly Phe Lys
            180                 185                 190

Asn Ser Pro Thr Leu Phe Asp Glu Ala Leu His Arg Asp Leu Ala Ser
        195                 200                 205

Phe Arg Ala Leu Asn Pro Gln Val Val Met Leu Gln Tyr Val Asp Asp
    210                 215                 220

Leu Leu Val Ala Ala Pro Thr Tyr Arg Asp Cys Lys Glu Gly Thr Arg
225                 230                 235                 240

Arg Leu Leu Gln Glu Leu Ser Lys Leu Gly Tyr Arg Val Ser Ala Lys
                245                 250                 255

Lys Ala Gln Leu Cys Arg Glu Val Thr Tyr Leu Gly Tyr Leu Leu
            260                 265                 270

Lys Gly Gly Lys Arg Trp Leu Thr Pro Ala Arg Lys Ala Thr Val Met
        275                 280                 285

Lys Ile Pro Thr Pro Thr Thr Pro Arg Gln Val Arg Glu Phe Leu Gly
    290                 295                 300

Thr Ala Gly Phe Cys Arg Leu Trp Ile Pro Gly Phe Ala Ser Leu Ala
305                 310                 315                 320

Ala Pro Leu Tyr Pro Leu Thr Arg Glu Lys Val Pro Phe Thr Trp Thr
                325                 330                 335

Glu Ala His Gln Glu Ala Phe Gly Arg Ile Lys Glu Ala Leu Leu Ser
            340                 345                 350

Ala Pro Ala Leu Ala Leu Pro Asp Leu Thr Lys Pro Phe Ala Leu Tyr
        355                 360                 365

Val Asp Glu Lys Glu Gly Val Ala Arg Gly Val Leu Thr Gln Thr Leu
    370                 375                 380

Gly Pro Trp Arg Arg Pro Val Ala Tyr Leu Ser Lys Lys Leu Asp Pro
385                 390                 395                 400

Val Ala Ser Gly Trp Pro Thr Cys Leu Lys Ala Ile Ala Ala Val Ala
                405                 410                 415

Leu Leu Leu Lys Asp Ala Asp Lys Leu Thr Leu Gly Gln Asn Val Leu
            420                 425                 430

Val Ile Ala Pro His Asn Leu Glu Ser Ile Val Arg Gln Pro Pro Asp
        435                 440                 445

Arg Trp Met Thr Asn Ala Arg Met Thr His Tyr Gln Ser Leu Leu Leu
    450                 455                 460

Asn Glu Arg Val Ser Phe Ala Pro Pro Ala Ile Leu Asn Pro Ala Thr
465                 470                 475                 480

Leu Leu Pro Val Glu Ser Asp Asp Thr Pro Ile His Ile Cys Ser Glu
                485                 490                 495

Ile Leu Ala Glu Glu Thr Gly Thr Arg Pro Asp Leu Arg Asp Gln Pro
            500                 505                 510

Leu Pro Gly Val Pro Ala Trp Tyr Thr Asp Gly Ser Ser Phe Ile Met
```

```
                    515                 520                 525
Asp Gly Arg Arg Gln Ala Gly Ala Ala Ile Val Asp Asn Thr Arg Thr
    530                 535                 540

Val Arg Ala Ser Asn Leu Pro Glu Gly Thr Ser Ala Gln Lys Ala Glu
545                 550                 555                 560

Leu Ile Ala Leu Thr Gln Ala Leu Arg Leu Ala Glu Gly Lys Ser Ile
                565                 570                 575

Asn Ile Tyr Thr Asp Ser Arg Tyr Ala Phe Ala Thr Ala His Val His
                580                 585                 590

Gly Ala Ile Tyr Lys Gln Arg Gly Leu Leu Thr Ser Ala Gly Lys Asp
                595                 600                 605

Ile Lys Asn Lys Glu Glu Ile Leu Ala Leu Leu Glu Ala Ile His Leu
                610                 615                 620

Pro Lys Arg Val Ala Ile Ile His Cys Pro Gly His Gln Arg Gly Thr
625                 630                 635                 640

Asp Pro Val Ala Thr Gly Asn Arg Lys Ala Asp Glu Ala Ala Lys Gln
                645                 650                 655

Ala Ala Gln Ser Thr Arg Ile Leu Thr Glu Thr Thr Lys Asn Gln Glu
                660                 665                 670

His

<210> SEQ ID NO 20
<211> LENGTH: 677
<212> TYPE: PRT
<213> ORGANISM: Sus scrofa

<400> SEQUENCE: 20

Met Thr Leu Gln Leu Asp Asp Glu Tyr Arg Leu Tyr Ser Pro Leu Val
1               5                   10                  15

Lys Pro Asp Gln Asn Ile Gln Phe Trp Leu Glu Gln Phe Pro Gln Ala
                20                  25                  30

Trp Ala Glu Thr Ala Gly Met Gly Leu Ala Lys Gln Val Pro Pro Gln
            35                  40                  45

Val Ile Gln Leu Lys Ala Ser Ala Thr Pro Val Ser Val Arg Gln Tyr
    50                  55                  60

Pro Leu Ser Lys Glu Ala Gln Glu Gly Ile Arg Pro His Val Gln Arg
65                  70                  75                  80

Leu Ile Gln Gln Gly Ile Leu Val Pro Val Gln Ser Pro Trp Asn Thr
                85                  90                  95

Pro Leu Leu Pro Val Arg Lys Pro Gly Thr Asn Asp Tyr Arg Pro Val
                100                 105                 110

Gln Asp Leu Arg Glu Val Asn Lys Arg Val Gln Asp Ile His Pro Thr
            115                 120                 125

Val Pro Asn Pro Tyr Asn Leu Leu Cys Ala Leu Pro Pro Gln Arg Ser
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Gly
                165                 170                 175

Thr Gly Arg Thr Gly Gln Leu Thr Trp Thr Arg Leu Pro Gln Gly Phe
                180                 185                 190

Lys Asn Ser Pro Thr Ile Phe Asp Glu Ala Leu His Arg Asp Leu Ala
            195                 200                 205

Asn Phe Arg Ile Gln His Pro Gln Val Thr Leu Leu Gln Tyr Val Asp
```

```
                210                 215                 220
Asp Leu Leu Leu Ala Gly Ala Thr Lys Gln Asp Cys Leu Glu Gly Thr
225                 230                 235                 240

Lys Ala Leu Leu Leu Glu Leu Ser Asp Leu Gly Tyr Arg Ala Ser Ala
                245                 250                 255

Lys Lys Ala Gln Ile Cys Arg Arg Glu Val Thr Tyr Leu Gly Tyr Ser
                260                 265                 270

Leu Arg Asp Gly Gln Arg Trp Leu Thr Glu Ala Arg Lys Lys Thr Val
            275                 280                 285

Val Gln Ile Pro Ala Pro Thr Thr Ala Lys Gln Met Arg Glu Phe Leu
        290                 295                 300

Gly Thr Ala Gly Phe Cys Arg Leu Trp Ile Pro Gly Phe Ala Thr Leu
305                 310                 315                 320

Ala Ala Pro Leu Tyr Pro Leu Thr Lys Glu Lys Gly Glu Phe Ser Trp
                325                 330                 335

Ala Pro Glu His Gln Lys Ala Phe Asp Ala Ile Lys Lys Ala Leu Leu
                340                 345                 350

Ser Ala Pro Ala Leu Ala Leu Pro Asp Val Thr Lys Pro Phe Thr Leu
            355                 360                 365

Tyr Val Asp Glu Arg Lys Gly Val Ala Arg Gly Val Leu Thr Gln Thr
        370                 375                 380

Leu Gly Pro Trp Arg Arg Pro Val Ala Tyr Leu Ser Lys Lys Leu Asp
385                 390                 395                 400

Pro Val Ala Ser Gly Trp Pro Ile Cys Leu Lys Ala Ile Ala Ala Val
                405                 410                 415

Ala Ile Leu Val Lys Asp Ala Asp Lys Leu Thr Leu Gly Gln Asn Ile
                420                 425                 430

Thr Val Ile Ala Pro His Ala Leu Glu Asn Ile Val Arg Gln Pro Pro
            435                 440                 445

Asp Arg Trp Met Thr Asn Ala Arg Met Thr His Tyr Gln Ser Leu Leu
        450                 455                 460

Leu Thr Glu Arg Val Thr Phe Ala Pro Pro Ala Ala Leu Asn Pro Ala
465                 470                 475                 480

Thr Leu Leu Pro Glu Glu Thr Asp Glu Pro Val Thr His Asp Cys His
                485                 490                 495

Gln Leu Leu Ile Glu Glu Thr Gly Val Arg Lys Asp Leu Thr Asp Ile
                500                 505                 510

Pro Leu Thr Gly Glu Val Leu Thr Trp Phe Thr Asp Gly Ser Ser Tyr
            515                 520                 525

Val Val Glu Gly Lys Arg Met Ala Gly Ala Ala Val Val Asp Gly Thr
        530                 535                 540

Arg Thr Ile Trp Ala Ser Ser Leu Pro Glu Gly Thr Ser Ala Gln Lys
545                 550                 555                 560

Ala Glu Leu Met Ala Leu Thr Gln Ala Leu Arg Leu Ala Glu Gly Lys
                565                 570                 575

Ser Ile Asn Ile Tyr Thr Asp Ser Arg Tyr Ala Phe Ala Thr Ala His
                580                 585                 590

Val His Gly Ala Ile Tyr Lys Gln Arg Gly Leu Leu Thr Ser Ala Gly
            595                 600                 605

Arg Glu Ile Lys Asn Lys Glu Lys Ile Leu Ser Leu Leu Glu Ala Val
        610                 615                 620

His Leu Pro Lys Arg Leu Ala Ile Ile His Cys Pro Gly His Gln Lys
625                 630                 635                 640
```

```
Ala Lys Asp Leu Ile Ser Arg Gly Asn Gln Met Ala Asp Arg Val Ala
                645                 650                 655

Lys Gln Ala Ala Gln Gly Val Asn Leu Leu Pro Ile Ile Glu Met Pro
            660                 665                 670

Lys Ala Pro Glu Pro
        675
```